(12) United States Patent
Sieg et al.

(10) Patent No.: US 7,563,862 B2
(45) Date of Patent: Jul. 21, 2009

(54) NEURAL REGENERATION PEPTIDES AND METHODS FOR THEIR USE IN TREATMENT OF BRAIN DAMAGE

(75) Inventors: Frank Sieg, Auckland (NZ); Paul Edmund Hughes, Auckland (NZ); Thorsten Gorba, Auckland (NZ)

(73) Assignee: Neuren Pharmaceuticals Limited, Auckland (NZ)

( * ) Notice: Subject to any disclaimer, the term of this patent is extended or adjusted under 35 U.S.C. 154(b) by 432 days.

(21) Appl. No.: 10/976,699

(22) Filed: Oct. 29, 2004

(65) Prior Publication Data

US 2005/0131212 A1 Jun. 16, 2005

Related U.S. Application Data

(63) Continuation-in-part of application No. 10/225,838, filed on Aug. 22, 2002.

(60) Provisional application No. 60/616,271, filed on Oct. 5, 2004, provisional application No. 60/585,041, filed on Jul. 2, 2004, provisional application No. 60/516,018, filed on Oct. 31, 2003, provisional application No. 60/314,952, filed on Aug. 24, 2001.

(51) Int. Cl.
| | |
|---|---|
| C07K 7/00 | (2006.01) |
| C07K 7/08 | (2006.01) |
| C07K 7/04 | (2006.01) |
| C12N 5/00 | (2006.01) |
| C12N 5/02 | (2006.01) |
| C12N 5/06 | (2006.01) |
| C12N 5/08 | (2006.01) |
| A61K 38/00 | (2006.01) |
| G01N 33/567 | (2006.01) |

(52) U.S. Cl. ............... 530/300; 435/368; 435/7.21; 435/1.1; 514/2

(58) Field of Classification Search .............. None
See application file for complete search history.

(56) References Cited

U.S. PATENT DOCUMENTS

| 5,834,192 A | 11/1998 | Akerblom et al. ........... 435/6 |
| 6,262,024 B1 | 7/2001 | Cunningham et al. ....... 514/12 |

FOREIGN PATENT DOCUMENTS

| WO | WO 97/38100 | 10/1997 |
| WO | WO 98/11136 | 3/1998 |

OTHER PUBLICATIONS

Blight Nat. Neurosci. 2002. 5: 1051-4.*
Schmidt et al. Annu. Rev. Biomed. Eng. 2003. 5: 293-347.*
Hoke et al. Nat. Clin. Pract. Neurol. 2006: 448-454.*
't Hart et al. Curr. Opin. Neurol. 2003. 16: 375-383.*
Burgess et al. J of Cell Bio. 1990, 111:2129-2138.*
Pawson et al. 2003, Science 300:445-452.*
Cunningham, et al. "Identification of a Survival-Promoting Peptide in Medium Conditioned by Oxidatively Stressed Cell Lines of Nervous System Origin," The Journal of Neuroscience, Sep. 15, 1998, vol. 18. No. 18, pp. 7047-7060.
Eagleson, "Rescue of Both Rapidly and Slowly Degenerating Neurons in the Dorsal Lateral Geniculate Nucleus of Adult Rats by a Cortically Derived Neuron Survival Factor", Exp. Neurol. May 1992; 116 (2) :156-162.
Springer, "Neurotrophic Factors as Therapeutic Agents", DN&P, Sep. 1991, pp. 394-399.
Eagleson, "Different Populations of Dorsal Lateral Geniculate Nucleus Neurons Have Concentration-Specific Requirements for a Cortically Derived Neuron Survival Factor", Exp Neurol. Dec. 1990; 110 (3) :284-290.
Barde, et al., "Purification of a new neurotophic factor from mammalian brain", EMBO Journal, vol. 1, No. 5, pp. 549-553, 1987.
Naharro G et al., "Gene Product of v-fgr onc: Hybrid Protein Containing a Portion of Actin and a Tyrosine-Specific Protein Kinase", Science, Jan. 1984; 223 (4631) :63-66.
Leibrock, et al, "Molecular cloning and expression of brain-derived neurotrophic factor", Nature, vol. 341, Sep. 14, 1989, pp. 149-152.
Port, et al., "A M, 70,000 Phosphoprotein of Sympathetic Neurons Regulated by Nerve Growth Factor and by Depolarization", The Journal of Biological Chemistry, vol. 259, No. 10, pp. 6526-6533.
ISR of PCT/US02/26782.

* cited by examiner

Primary Examiner—Christine J Saoud
Assistant Examiner—Chang-Yu Wang
(74) Attorney, Agent, or Firm—D. Benjamin Borson; Borson Law Group, PC

(57) ABSTRACT

The invention discloses a family of peptides termed NRP compounds or NRPs that can promote neuronal migration, neurite outgrowth, neuronal proliferation, neural differentiation and/or neuronal survival, and provides compositions and methods for the use of NRPs in the treatment of brain injury and neurodegenerative disease. NRP compounds can induce neurons and neuroblasts to proliferate and migrate into areas of damage caused by acute brain injury or chronic neurodegenerative disease, such as exposure to toxins, stroke, trauma, nervous system infections, demyelinating diseases, dementias, and metabolic disorders. NRP compounds may be administered directly to a subject or to a subject's cells by a variety of means including orally, intraperitoneally, intravascularly, and directly into the nervous system of a patient. NRP compounds can be formulated into pharmaceutically acceptable dose forms for therapeutic use. Methods for detecting neural regeneration, neural proliferation, neural differentiation, neurite outgrowth and neural survival can be used to develop other neurally active agents.

28 Claims, 68 Drawing Sheets
(16 of 68 Drawing Sheet(s) Filed in Color)

```
mouNRP1-105  MNRNPG  TPEPP  P  ISS  CC  RQPED ED  C GFI  GC A P CF PAFPL
cachexial-93 -M PMT  FLT--  IL  ALV  YD  ASAP-I-S  P -HE  AG EA ES GLARQ
consensus    m-R---vv---epA-AG---sA--P-c----dGe-Gg-Cg--s-A--r-q-C--P----- mouNRP1-105  L  AE  AGDSGPGS  RR  RGA  GSEPS  RRAP  H  UVVCAS  A
cachexial-93 A  K  RKQ-----  SS  KKG  DCAKK  VCGL  L  KDAVED  E       34.4%
consensus    -Pa-P---sgpgsR--LL---L-----A----Gr-G------L-s
```

FIGURE 29C

```
mouNRP27-66  ----------------------------  R  SDS  CC  PIS---- A  ---R
Pa2trefoil   MATMSNKVICALVLVSMLALGTLAEAQTS  TVA  I NC  FP  VTPSQCR  K  CFBD   52.5%
consensus    matmsnkvicalvlvsmlalgtlaeaqtstCt--PRd-e--C--G----sqcah-CCctdmouNRP27-66  R  ---  H  PF  H  AP  --
Pa2trefoil   TV  VP  E ID  P  ESP
consensus    d-RCvpwCPyP-a--1-P-E-aef
```

FIGURE 29D

```
mouNRP1-94   MNRNPG  PEEPAR  L  ASG  NQP  SEEGS  -  SHAG  RGCFPEA-F
mouSDP-alpha --MDAE  VLALVL  A D  DGF  LST----  P  PESHI  VRHLEILNT     32.6%
consensus    mn----VVt-------A-ls-s---P-c---RdgedggCpC-P-----GRAg--------R- mouNRP1-94   LLPA  PAGDSGP  P  RL  RGA  GSEP  -AR  E
mouSDP-alpha NCAL  IVARLES  R  VC  DPR  KWIQ  IL   L
consensus    P----g-------g-Rh--l---L----Ey--rA-gr
```

FIGURE 29E

4.7 kb
rRNA 1.9 kb
rRNA 1.2 kb 0.8 kb

FIGURE 34D

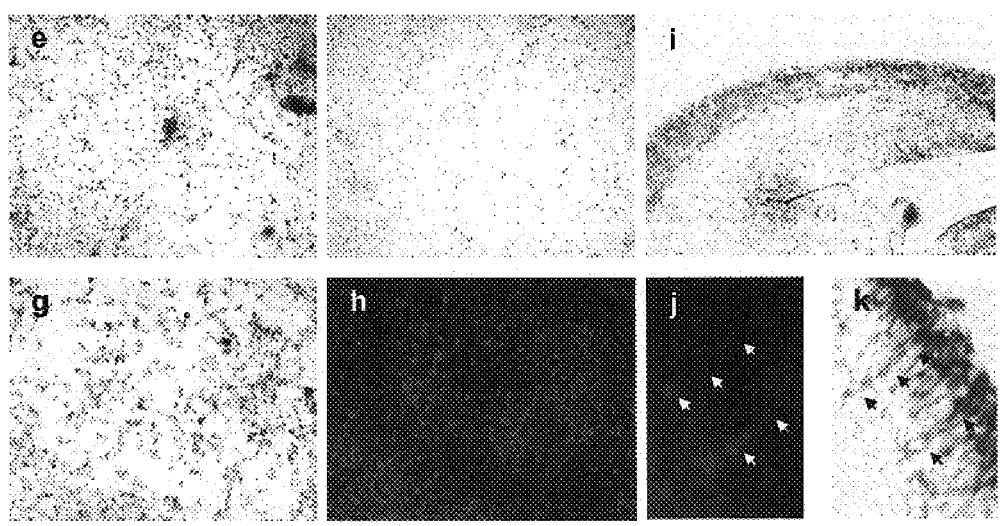
FIGURES 34E-K

NRP-4 segment PQ given i.c.v. 2 h after HI injury

Legend:
- Control (n = 10) 2/12 rats died
- 5 nM (n = 12) 0/12 rats died
- 50 nM (n = 12) 3/15 rats died
- 500 nM (n = 12) 0/12 rats died Y-axis: Tissue Damage Score
X-axis (Brain Region): Striatum, CA1/2, CA3, CA4, DG, Cortex

FIGURE 40A

Haptotactic migration assay using mouse NSCs and NRP-5 RG as chemoattractant

BSA control
NRP-5 RG

★★ $p<0.01$ (N=12)

100pg of NRP-5 segment RG coating leads to an increase in chemoattraction of 42.1%.

FIGURE 44

SEQUENCE LISTING

```
<160> NUMBER OF SEQ ID NOS: 49

<210> SEQ ID NO 1
<211> LENGTH: 48
<212> TYPE: DNA
<213> ORGANISM: RAT

<400> SEQUENCE: 1
tatgatccag aggccgcctc tgccccagga tcggggaacc cttgccat          48
```

```
<210> SEQ ID NO 2
<211> LENGTH: 16
<212> TYPE: PRT
<213> ORGANISM: RAT
<220> FEATURE:
<221> NAME/KEY: MOD_RES
<222> LOCATION: (16)..(16)
<223> OTHER INFORMATION: AMIDATION

<400> SEQUENCE: 2

Tyr Asp Pro Glu Ala Ala Ser Ala Pro Gly Ser Gly Asn Pro Cys His
1               5                   10                  15

<210> SEQ ID NO 3
<211> LENGTH: 48
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (3)..(6)
<223> OTHER INFORMATION: n=t/c
<220> FEATURE:
<221> NAME/KEY: misc_feature
<222> LOCATION: (9)..(9)
<223> OTHER INFORMATION: n=a/t/c/g
<220> FEATURE:
<221> NAME/KEY: misc_feature
<222> LOCATION: (12)..(12)
<223> OTHER INFORMATION: n=g/a
<220> FEATURE:
<221> NAME/KEY: misc_feature
<222> LOCATION: (15)..(36)
<223> OTHER INFORMATION: n=a/t/c/g
<220> FEATURE:
<221> NAME/KEY: misc_feature
<222> LOCATION: (39)..(39)
<223> OTHER INFORMATION: n=t/c
<220> FEATURE:
<221> NAME/KEY: misc_feature
<222> LOCATION: (42)..(42)
<223> OTHER INFORMATION: n=a/t/c/g
<220> FEATURE:
<221> NAME/KEY: misc_feature
<222> LOCATION: (45)..(48)
<223> OTHER INFORMATION: n=t/c

<400> SEQUENCE: 3
tanganccng angcngcntc ngcnccnggn tcnggnaanc cntgncan                  48

<210> SEQ ID NO 4
<211> LENGTH: 333
<212> TYPE: DNA
<213> ORGANISM: HUMAN

<400> SEQUENCE: 4
atgagagtca gagtacaact caagtctaat gtccaagttg gagcaggaca ctcagcaaag     60
gatccagagg caaggagagc acctggaagc ctacatccct gtctagcagc atcatgctca    120
gctgctggcc tgcacacaag ctcgtggaag aacctgtttt tgatagaagg actagtaagt    180
atttgcctag ggcacatagt tgtacaagag acggacgttt ttaggtcctt gcggtttctt    240
gcatttccag aaaacttgct tcaaatattt ttccagatgc aaaattcctt ggatccttgt    300
tttagaatga atctattaaa aacttcacat taa                                 333

<210> SEQ ID NO 5
<211> LENGTH: 110
<212> TYPE: PRT
```

<213> ORGANISM: HUMAN

<400> SEQUENCE: 5

```
Met Arg Val Arg Val Gln Leu Lys Ser Asn Val Gln Val Gly Ala Gly
1               5                   10                  15

His Ser Ala Lys Asp Pro Glu Ala Arg Arg Ala Pro Gly Ser Leu His
            20                  25                  30

Pro Cys Leu Ala Ala Ser Cys Ser Ala Ala Gly Leu His Thr Ser Ser
        35                  40                  45

Trp Lys Asn Leu Phe Trp Ile Glu Gly Leu Val Ser Ile Cys Leu Gly
    50                  55                  60

His Ile Val Val Gln Glu Thr Asp Val Phe Arg Ser Leu Arg Phe Leu
65                  70                  75                  80

Ala Phe Pro Glu Asn Leu Leu Gln Ile Phe Phe Gln Met Gln Asn Ser
                85                  90                  95

Leu Asp Pro Cys Phe Arg Met Asn Leu Leu Lys Thr Ser His
            100                 105                 110
```

<210> SEQ ID NO 6
<211> LENGTH: 336
<212> TYPE: DNA
<213> ORGANISM: HUMAN

<400> SEQUENCE: 6

```
atgaaaataa atgtattaat taaattaatg accaagtcag attcttttaa aagccaagcc      60
aggggccaag ttcccccatt tctagggggg gtggggtgcc cctggttttt tcaaacaagg     120
ttttggggcc atagttttgc agttaaactg gcctccaacc tttcccaggc agagaaattg     180
gtccttcagc aaacccttc ccaaaaaggc ctagacggga caaaaaaagc tgtgggggga     240
ctcggaaaac taggaaaaga tgcagtcgaa gatctagaaa gcgtgggtaa aggagccgtc     300
catgacgtta aagacgtcct tgactcagta ctatag                              336
```

<210> SEQ ID NO 7
<211> LENGTH: 111
<212> TYPE: PRT
<213> ORGANISM: HUMAN

<400> SEQUENCE: 7

```
Met Lys Ile Asn Val Leu Ile Lys Leu Met Thr Lys Ser Asp Ser Phe
1               5                   10                  15

Lys Ser Gln Ala Arg Gly Gln Val Pro Pro Phe Leu Gly Gly Val Gly
            20                  25                  30

Cys Pro Trp Phe Phe Gln Thr Arg Phe Trp Gly His Ser Phe Ala Val
        35                  40                  45

Lys Leu Ala Ser Asn Leu Ser Gln Ala Glu Lys Leu Val Leu Gln Gln
    50                  55                  60

Thr Leu Ser Gln Lys Gly Leu Asp Gly Ala Lys Lys Ala Val Gly Gly
65                  70                  75                  80

Leu Gly Lys Leu Gly Lys Asp Ala Val Glu Asp Leu Glu Ser Val Gly
                85                  90                  95

Lys Gly Ala Val His Asp Val Lys Asp Val Leu Asp Ser Val Leu
            100                 105                 110
```

<210> SEQ ID NO 8
<211> LENGTH: 438
<212> TYPE: DNA
<213> ORGANISM: HUMAN

```
<220> FEATURE:
<221> NAME/KEY: Unsure
<222> LOCATION: (353)..(354)
<223> OTHER INFORMATION: n=a/c/t/g
<220> FEATURE:
<221> NAME/KEY: misc_feature
<222> LOCATION: (353)..(354)
<223> OTHER INFORMATION: n is a, c, g, or t

<400> SEQUENCE: 8
atggctgttg tgttacttgc accatttggg gacatcagcc aggaaatcac aaaggttggg    60
acagggactc cagggagggc tgaggccggg ggccaggtgt ctccatgcct ggcggcgtcc   120
tgcagtcagg cctatggcgc catcttggct cactgcaacc tctgcctccc aggttcaatg   180
attaaaaaaa agaagaaatt tatagttgaa atagaaagtc aacctttaaa gtcttacagg   240
gaaaattcta cccatttttcc cagaccagtc ctaaatctta tgcgaaaaca ctgtggggaa   300 aaggggggaag aagggccttg tttctctccc aagcaaatgg gggagaggcg agnntgtggc   360
ggagggctag ggttggctcg cgagatcact aatttaacat ccgctcatct gttggtcttg   420
aatatcagca accagtga                                                  438

<210> SEQ ID NO 9
<211> LENGTH: 145
<212> TYPE: PRT
<213> ORGANISM: HUMAN
<220> FEATURE:
<221> NAME/KEY: UNSURE
<222> LOCATION: (118)..(118)
<223> OTHER INFORMATION: X=A/D/E/G/V

<400> SEQUENCE: 9

Met Ala Val Val Leu Leu Ala Pro Phe Gly Asp Ile Ser Gln Glu Ile
1               5                   10                  15

Thr Lys Val Gly Thr Gly Thr Pro Gly Arg Ala Glu Ala Gly Gly Gln
            20                  25                  30

Val Ser Pro Cys Leu Ala Ala Ser Cys Ser Gln Ala Tyr Gly Ala Ile
        35                  40                  45

Leu Ala His Cys Asn Leu Cys Leu Pro Gly Ser Met Ile Lys Lys Lys
    50                  55                  60

Lys Lys Phe Ile Val Glu Ile Glu Ser Gln Pro Leu Lys Ser Tyr Arg
65                  70                  75                  80

Glu Asn Ser Thr His Phe Pro Arg Gly Val Leu Asn Leu Met Arg Lys
                85                  90                  95

His Cys Gly Glu Lys Gly Glu Gly Pro Cys Phe Ser Pro Lys Gln
            100                 105                 110

Met Gly Glu Arg Arg Xaa Cys Gly Gly Leu Gly Leu Ala Arg Glu
        115                 120                 125

Ile Thr Asn Leu Thr Ser Ala His Leu Leu Val Leu Asn Ile Ser Asn
    130                 135                 140

Gln
145

<210> SEQ ID NO 10
<211> LENGTH: 801
<212> TYPE: DNA
<213> ORGANISM: HUMAN

<400> SEQUENCE: 10
atgctggacc cgtcttccag cgaagaggag tcggacgagg ggctggaaga ggaaagccgc   60
```

```
gatgtgctgg tggcagccgg cagctcgcag cgagctcctc cagccccgac tcgggaaggg    120
cggcgggacg cgccggggcg cgcgggcggc ggcggcgcgg ccagatctgt gagcccgagc    180
ccctctgtgc tcagcgaggg gcgagacgag ccccagcggc agctggacca tgagcaggag    240
cggaggatcc gcctgcagct ctacgtcttc gtcgtgaggt gcatcgcgta ccccttcaac    300
gccaagcagc ccaccgacat ggcccggagg cagcagaagc ttaacaaaca acagttgcag    360
ttactgaaag aacggttcca ggccttcctc aatggggaaa cccaaattgt agctgacgaa    420
gcattttgca acgcagttcg gagttattat gaggttttc taaagagtga ccgagtggcc    480
agaatggtac agagtggagg gtgttctgct aaggacttca gagaagtatt taagaaaaac    540
atagaaaaac gtgtgcggag tttgccagaa gtggatggct tgagcaaaga gacagtgttg    600
agctcatgga tagccaaata tgatgccatt tacagaggtg aagaggactt gtgcaaacag    660
ccaaatagaa tggcccctaag tgcagtgtct gaacttattc tgagcaagga caactctat     720 gaaatgtttc agcagattct gggtattaaa aaactggaac cagctcctt ttataatgca     780 tgtcaggtaa gtggtctctg a                                              801

<210> SEQ ID NO 11
<211> LENGTH: 266
<212> TYPE: PRT
<213> ORGANISM: HUMAN

<400> SEQUENCE: 11

Met Leu Asp Pro Ser Ser Glu Glu Glu Ser Asp Glu Gly Leu Glu
1               5                   10                  15

Glu Glu Ser Arg Asp Val Leu Ala Ala Gly Ser Ser Gln Arg Ala
                20                  25                  30

Pro Pro Ala Pro Thr Arg Glu Gly Arg Arg Asp Ala Pro Gly Arg Ala
            35                  40                  45

Gly Gly Gly Gly Ala Ala Arg Ser Val Ser Pro Ser Pro Ser Val Leu
        50                  55                  60

Ser Glu Gly Arg Asp Glu Pro Gln Arg Gln Leu Asp Asp Gln Glu
65                  70                  75                  80

Arg Arg Ile Arg Leu Gln Leu Tyr Val Phe Val Arg Cys Ile Ala
                85                  90                  95

Tyr Pro Phe Asn Ala Lys Gln Pro Thr Asp Met Ala Arg Arg Gln Gln
            100                 105                 110

Lys Leu Asn Lys Gln Gln Leu Gln Leu Leu Lys Glu Arg Phe Gln Ala
        115                 120                 125

Phe Leu Asn Gly Glu Thr Gln Ile Val Ala Asp Glu Ala Phe Cys Asn
    130                 135                 140

Ala Val Arg Ser Tyr Tyr Glu Val Phe Leu Lys Ser Asp Arg Val Ala
145                 150                 155                 160

Arg Met Val Gln Ser Gly Gly Cys Ser Ala Asn Asp Phe Arg Glu Val
                165                 170                 175

Phe Lys Lys Asn Ile Glu Lys Arg Val Arg Ser Leu Pro Glu Ile Asp
            180                 185                 190

Gly Leu Ser Lys Glu Thr Val Leu Ser Ser Trp Ile Ala Lys Tyr Asp
        195                 200                 205

Ala Ile Tyr Arg Gly Glu Glu Asp Leu Cys Lys Gln Pro Asn Arg Met
    210                 215                 220

Ala Leu Ser Ala Val Ser Glu Leu Ile Leu Ser Lys Glu Gln Leu Tyr
225                 230                 235                 240
```

Glu Met Phe Gln Gln Ile Leu Gly Ile Lys Lys Leu Glu His Gln Leu
            245                 250                 255

Leu Tyr Asn Ala Cys Gln Val Ser Gly Leu
            260                 265

<210> SEQ ID NO 12
<211> LENGTH: 237
<212> TYPE: DNA
<213> ORGANISM: HUMAN

<400> SEQUENCE: 12
atgagagaca acaacatct aaatgcaaga cataaaaagg aaaggaagga gagatcatat      60
agtacaacac tacaaggtgt tctcaacaaa aagtctttgt tagacttcaa taatactatt     120
tggtacttct atcagcaaat aggaagcatt ccaatactta ttagatcctc taccatcaga    180
cacagaaatt acctagaaaa cagaaatgta ttgccaaatc tcaaacaaga gggctga       237

<210> SEQ ID NO 13
<211> LENGTH: 78
<212> TYPE: PRT
<213> ORGANISM: HUMAN

<400> SEQUENCE: 13

Met Arg Asp Lys Gln His Leu Asn Ala Arg His Lys Lys Glu Arg Lys
1               5                   10                  15

Glu Arg Ser Tyr Ser Thr Thr Leu Gln Gly Val Leu Asn Lys Lys Ser
            20                  25                  30

Leu Leu Asp Phe Asn Asn Thr Ile Trp Tyr Phe Tyr Gln Gln Ile Gly
        35                  40                  45

Ser Ile Pro Ile Leu Ile Arg Ser Ser Thr Ile Arg His Arg Asn Tyr
    50                  55                  60

Leu Glu Asn Arg Asn Val Leu Pro Asn Leu Lys Gln Glu Gly
65                  70                  75

<210> SEQ ID NO 14
<211> LENGTH: 449
<212> TYPE: DNA
<213> ORGANISM: MOUSE

<400> SEQUENCE: 14
ggcagcctcg agatggggaa gatggcggct gctgtggctt cattagccac gctggctgca      60
gagcccagag aggatgcttt ccggaagctt ttccgcttct accggcagag ccggccgggg     120
acagcggacc tgggagccgt catcgacttc tcagaggcgc acttggctcg gagcccgaag     180
cccggcgtgc cccaggtagg aaaggaggag tagtgtgtgc cagcctagcg gccgactggg     240
ccacccgaga ctgggccgcc tccgcggctt tggagggaag cccctgctgg gcctgtccag     300
tgagctgtaa tgtcgagcga tgagcgacca gctgcctcgc tgtcccaacg ctctggccac     360
ggcttgtgcc ttgccgccat tcccccaac ccacgcgggc cacggcttgt gccctgccgc      420
catttccccc aacccacgcg accttgctc                                       449

<210> SEQ ID NO 15
<211> LENGTH: 66
<212> TYPE: PRT
<213> ORGANISM: MOUSE

<400> SEQUENCE: 15

Met Gly Lys Met Ala Ala Ala Val Ala Ser Leu Ala Thr Leu Ala Ala
1               5                   10                  15

```
Glu Pro Arg Glu Asp Ala Phe Arg Lys Leu Phe Arg Phe Tyr Arg Gln
            20                  25                  30

Ser Arg Pro Gly Thr Ala Asp Leu Gly Ala Val Ile Asp Phe Ser Glu
        35                  40                  45

Ala His Leu Ala Arg Ser Pro Lys Pro Gly Val Pro Gln Val Gly Lys
    50                  55                  60

Glu Glu
65
```

<210> SEQ ID NO 16
<211> LENGTH: 342
<212> TYPE: DNA
<213> ORGANISM: MOUSE

<400> SEQUENCE: 16

```
atgaatcgaa accctggagt ccctcgagat ggggaagatg gcggctgctg tggcttcatt      60
agccacgctg gctgcagagc ccagagagga tgctttccgg aagcttttcc gcttctaccg     120
gcagagccgg ccggggacag cggacctggg agccgtcatc gacttctcag aggcgcactt     180
ggctcggagc ccgaagcccg gcgtgcccca ggtaggaaag gaggagtagt gtgtgccagc     240
ctagcggccg actgggccac cgagactggg ccgcctccg gccggcttt ggagggaagc       300
ccctgctggg cctgtccagt gagctgtaat gtcgagcgat ga                        342
```

<210> SEQ ID NO 17
<211> LENGTH: 113
<212> TYPE: PRT
<213> ORGANISM: MOUSE

<400> SEQUENCE: 17

```
Met Asn Arg Asn Pro Gly Val Pro Arg Asp Gly Glu Asp Gly Gly Cys
1               5                  10                  15

Cys Gly Phe Ile Ser His Ala Gly Cys Arg Ala Gln Arg Gly Cys Phe
            20                  25                  30

Pro Glu Ala Phe Pro Leu Leu Pro Ala Glu Pro Ala Gly Asp Ser Gly
        35                  40                  45

Pro Gly Ser Arg His Arg Leu Leu Arg Gly Ala Leu Gly Ser Glu Pro
    50                  55                  60

Glu Ala Arg Arg Ala Pro Gly Arg Lys Gly Gly Val Val Cys Ala Ser
65                  70                  75                  80

Leu Ala Ala Asp Trp Ala Thr Arg Asp Trp Ala Ala Ser Gly Pro Ala
                85                  90                  95

Leu Glu Gly Ser Pro Cys Trp Ala Cys Pro Val Ser Cys Asn Val Glu
            100                 105                 110

Arg
```

<210> SEQ ID NO 18
<211> LENGTH: 24
<212> TYPE: PRT
<213> ORGANISM: HUMAN
<220> FEATURE:
<221> NAME/KEY: MOD_RES
<222> LOCATION: (24)..(24)
<223> OTHER INFORMATION: AMIDATION

<400> SEQUENCE: 18

```
Lys Asp Pro Glu Ala Arg Arg Ala Pro Gly Ser Leu His Pro Cys Leu
1               5                  10                  15
```

Ala Ala Ser Cys Ser Ala Ala Gly
            20

<210> SEQ ID NO 19
<211> LENGTH: 426
<212> TYPE: DNA
<213> ORGANISM: MOUSE

<400> SEQUENCE: 19
atgtgcactc tgcaggtatg gtcttcctcc ctcccttccc tcccccacct ctctgagggg      60 tcagggtca gcatttggat gctgctccca ccaggcccag ctttagaaat gaattcctcc     120
ggcctccttt atactcttga gacctcctgg ggaaccagga ccctcttggc tcctctggtg     180
acatacatgg gatctgatgc atctgaggtg gatgcaagaa gagcaaaaaa gagtctccac     240
tgcatcctgt ctgacaccag ccatccccgg ggccatgccc ggaatgagag gaggcttggc     300
cttggggttt ggaagaccga gctttgggtc cagaccctgc tatcactgat ggtgacatcc     360
tgggaagttt atgaaactcg ttcgtgcctc agtttcccca tcaggccttt agctcactgg     420
ggataa                                                               426

<210> SEQ ID NO 20
<211> LENGTH: 141
<212> TYPE: PRT
<213> ORGANISM: MOUSE

<400> SEQUENCE: 20

Met Cys Thr Leu Gln Val Trp Ser Ser Leu Pro Ser Leu Pro His
1               5                   10                  15

Leu Ser Glu Gly Ser Gly Val Ser Ile Trp Met Leu Leu Pro Pro Gly
            20                  25                  30

Pro Ala Leu Glu Met Asn Ser Ser Gly Leu Leu Tyr Thr Leu Glu Thr
        35                  40                  45

Ser Trp Gly Thr Arg Thr Leu Leu Ala Pro Leu Val Thr Tyr Met Gly
    50                  55                  60

Ser Asp Ala Ser Glu Val Asp Ala Arg Arg Ala Lys Lys Ser Leu His
65                  70                  75                  80

Cys Ile Leu Ser Asp Thr Ser His Pro Arg Gly His Ala Arg Asn Glu
                85                  90                  95

Arg Arg Leu Gly Leu Gly Val Trp Lys Thr Glu Leu Trp Val Gln Thr
            100                 105                 110

Leu Leu Ser Leu Met Val Thr Ser Trp Glu Val Tyr Glu Thr Arg Ser
        115                 120                 125

Cys Leu Ser Phe Pro Ile Arg Leu Leu Ala His Trp Gly
    130                 135                 140

<210> SEQ ID NO 21
<211> LENGTH: 498
<212> TYPE: PRT
<213> ORGANISM: Mycobacterium tuberculosis

<400> SEQUENCE: 21

Met Ser Phe Val Val Thr Ile Pro Glu Ala Leu Ala Ala Val Ala Thr
1               5                   10                  15

Asp Leu Ala Gly Ile Gly Ser Thr Ile Gly Thr Ala Asn Ala Ala Ala
            20                  25                  30

Ala Val Pro Thr Thr Thr Val Leu Ala Ala Ala Ala Asp Glu Val Ser
        35                  40                  45

```
Ala Ala Met Ala Ala Leu Phe Ser Gly His Ala Gln Ala Tyr Gln Ala
 50                  55                  60

Leu Ser Ala Gln Ala Ala Leu Phe His Glu Gln Phe Val Arg Ala Leu
 65                  70                  75                  80

Thr Ala Gly Ala Gly Ser Tyr Ala Ala Glu Ala Ala Ser Ala Ala
                 85                  90                  95

Pro Leu Glu Gly Val Leu Asp Val Ile Asn Ala Pro Ala Leu Ala Leu
            100                 105                 110

Leu Gly Arg Pro Leu Ile Gly Asn Gly Ala Asn Gly Ala Pro Gly Thr
            115                 120                 125

Gly Ala Asn Gly Gly Asp Gly Ile Leu Ile Gly Asn Gly Gly Ala
        130                 135                 140

Gly Gly Ser Gly Ala Ala Gly Met Pro Gly Gly Asn Gly Gly Ala Ala
145                 150                 155                 160

Gly Leu Phe Gly Asn Gly Gly Ala Gly Ala Gly Gly Asn Val Ala
                165                 170                 175

Ser Gly Thr Ala Gly Phe Gly Gly Ala Gly Gly Ala Gly Gly Leu Leu
            180                 185                 190

Tyr Gly Ala Gly Gly Ala Gly Gly Ala Gly Gly Arg Ala Gly Gly Gly
            195                 200                 205

Val Gly Gly Ile Gly Gly Ala Gly Gly Ala Gly Asn Gly Gly Leu
210                 215                 220

Leu Phe Gly Ala Gly Gly Ala Gly Gly Val Gly Gly Leu Ala Ala Asp
225                 230                 235                 240

Ala Gly Asp Gly Gly Ala Gly Gly Asp Gly Leu Phe Phe Gly Val
                245                 250                 255

Gly Gly Ala Gly Gly Ala Gly Gly Thr Gly Thr Asn Val Thr Gly Gly
            260                 265                 270

Ala Gly Gly Ala Gly Gly Asn Gly Gly Leu Leu Phe Gly Ala Gly Gly
            275                 280                 285

Val Gly Gly Val Gly Gly Asp Gly Val Ala Phe Leu Gly Thr Ala Pro
            290                 295                 300

Gly Gly Pro Gly Gly Ala Gly Gly Ala Gly Leu Phe Gly Val Gly
305                 310                 315                 320

Gly Ala Gly Gly Ala Gly Gly Ile Gly Leu Val Gly Asn Gly Gly Ala
                325                 330                 335

Gly Gly Ser Gly Gly Ser Ala Leu Leu Trp Gly Asp Gly Gly Ala Gly
            340                 345                 350

Gly Ala Gly Gly Val Gly Ser Thr Thr Gly Gly Ala Gly Gly Ala Gly
            355                 360                 365

Gly Asn Ala Gly Leu Leu Val Gly Ala Gly Gly Ala Gly Gly Ala Gly
            370                 375                 380

Ala Leu Gly Gly Ala Thr Gly Val Gly Gly Ala Gly Gly Asn Gly
385                 390                 395                 400

Gly Thr Ala Gly Leu Leu Phe Gly Ala Gly Gly Ala Gly Gly Phe Gly
                405                 410                 415

Phe Gly Gly Ala Gly Gly Ala Gly Gly Leu Gly Gly Lys Ala Gly Leu
            420                 425                 430

Ile Gly Asp Gly Gly Asp Gly Gly Ala Gly Gly Asn Gly Thr Gly Ala
            435                 440                 445

Lys Gly Gly Asp Gly Gly Ala Gly Gly Ala Ile Leu Val Gly Asn
450                 455                 460

Gly Gly Asn Gly Gly Asn Ala Gly Ser Gly Thr Pro Asn Gly Ser Ala
```

```
                    465                 470                 475                 480
Gly Thr Gly Gly Ala Gly Gly Leu Leu Gly Lys Asn Gly Met Asn Gly
                485                 490                 495

Leu Pro

<210> SEQ ID NO 22
<211> LENGTH: 641
<212> TYPE: PRT
<213> ORGANISM: Epstein Barr Virus

<400> SEQUENCE: 22

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
                20                  25                  30

Arg Arg Gly Gly Asp Asn His Gly Arg Gly Arg Gly Arg Gly Arg Gly
            35                  40                  45

Arg Gly Gly Gly Arg Pro Gly Ala Pro Gly Gly Ser Gly Ser Gly Pro
        50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Ala Gly Ala Gly Gly
                100                 105                 110

Gly Ala Gly Gly Ala Gly Gly Ala Gly Gly Ala Gly Ala Gly Gly Gly
            115                 120                 125

Gly Ala Gly Ala Gly Gly Ala Gly Ala Gly Gly Ala Gly Ala Gly Ala
        130                 135                 140

Gly Gly Ala Gly Ala Gly Gly Ala Gly Ala Gly Ala Gly Gly Ala Gly
145                 150                 155                 160

Gly Ala Gly Gly Ala Gly Ala Gly Ala Gly Gly Ala Gly Ala Gly Gly
                165                 170                 175

Ala Gly Gly Ala Gly Gly Ala Gly Ala Gly Gly Ala Gly Gly Ala Gly
                180                 185                 190

Ala Gly Gly Ala Gly Ala Gly Gly Ala Gly Ala Gly Gly Ala Gly Gly
            195                 200                 205

Gly Ala Gly Gly Ala Gly Ala Gly Gly Ala Gly Ala Gly Gly Gly Ala
        210                 215                 220

Gly Gly Ala Gly Gly Ala Gly Ala Gly Gly Ala Gly Ala Gly Gly Ala
225                 230                 235                 240

Gly Ala Gly Gly Ala Gly Ala Gly Gly Ala Gly Ala Gly Gly Ala Gly
                245                 250                 255

Gly Ala Gly Gly Ala Gly Ala Gly Gly Ala Gly Ala Gly Gly Ala Gly
                260                 265                 270

Gly Gly Ala Gly Gly Ala Gly Ala Gly Gly Ala Gly Gly Ala Gly Ala
            275                 280                 285

Ala Gly Gly Ala Gly Gly Ala Gly Ala Gly Gly Ala Gly Gly Ala Gly
        290                 295                 300

Ala Gly Gly Ala Gly Gly Ala Gly Ala Gly Gly Ala Gly Gly Ala Gly
305                 310                 315                 320

Gly Ala Gly Ala Gly Gly Gly Gly Arg Gly Arg Gly Gly Ser Gly Gly
                325                 330                 335

Arg Gly Arg Gly Gly Ser Gly Gly Arg Gly Arg Gly Gly Ser Gly Gly
```

-continued

```
                340                 345                 350
Arg Arg Gly Arg Gly Arg Glu Arg Ala Arg Gly Ser Arg Glu Arg
            355                 360                 365
Ala Arg Gly Arg Gly Arg Gly Arg Gly Glu Lys Arg Pro Arg Ser Pro
        370                 375                 380
Ser Ser Gln Ser Ser Ser Gly Ser Pro Pro Arg Arg Pro Pro Pro
385                 390                 395                 400
Gly Arg Arg Pro Phe Phe His Pro Val Gly Glu Ala Asp Tyr Phe Glu
                405                 410                 415
Tyr His Gln Glu Gly Gly Pro Asp Gly Glu Pro Asp Val Pro Pro Gly
            420                 425                 430
Ala Ile Glu Gln Gly Pro Ala Asp Asp Pro Gly Glu Gly Pro Ser Thr
        435                 440                 445
Gly Pro Arg Gly Gln Gly Asp Gly Gly Arg Arg Lys Lys Gly Gly Trp
450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
                485                 490                 495
Thr Thr Asp Glu Gly Thr Trp Val Ala Gly Val Phe Val Tyr Gly Gly
            500                 505                 510
Ser Lys Thr Ser Leu Tyr Asn Leu Arg Arg Gly Thr Ala Leu Ala Ile
        515                 520                 525
Pro Gln Cys Arg Leu Thr Pro Leu Ser Arg Leu Pro Phe Gly Met Ala
    530                 535                 540
Pro Gly Pro Gly Pro Gln Pro Gly Pro Leu Arg Glu Ser Ile Val Cys
545                 550                 555                 560
Tyr Phe Met Val Phe Leu Gln Thr His Ile Phe Ala Glu Val Leu Lys
                565                 570                 575
Asp Ala Ile Lys Asp Leu Val Met Thr Lys Pro Ala Pro Thr Cys Asn
            580                 585                 590
Ile Arg Val Thr Val Cys Ser Phe Asp Asp Gly Val Asp Leu Pro Pro
        595                 600                 605
Trp Phe Pro Pro Met Val Glu Gly Ala Ala Glu Gly Asp Asp Gly
    610                 615                 620
Asp Asp Gly Asp Glu Gly Gly Asp Gly Asp Glu Gly Glu Glu Gly Gln
625                 630                 635                 640
Glu

<210> SEQ ID NO 23
<211> LENGTH: 19
<212> TYPE: PRT
<213> ORGANISM: HUMAN
<220> FEATURE:
<221> NAME/KEY: MOD_RES
<222> LOCATION: (19)..(19)
<223> OTHER INFORMATION: AMIDATION

<400> SEQUENCE: 23

Lys Asp Pro Glu Ala Arg Arg Ala Pro Gly Ser Leu His Pro Cys Leu
1               5                   10                  15

Ala Ala Ser

<210> SEQ ID NO 24
<211> LENGTH: 24
<212> TYPE: PRT
```

```
<213> ORGANISM: MOUSE
<220> FEATURE:
<221> NAME/KEY: MOD_RES
<222> LOCATION: (24)..(24)
<223> OTHER INFORMATION: AMIDATION

<400> SEQUENCE: 24

Ser Glu Pro Glu Ala Arg Arg Ala Pro Gly Arg Lys Gly Gly Val Val
1               5                   10                  15

Cys Ala Ser Leu Ala Ala Asp Trp
            20

<210> SEQ ID NO 25
<211> LENGTH: 11
<212> TYPE: PRT
<213> ORGANISM: HUMAN
<220> FEATURE:
<221> NAME/KEY: MOD_RES
<222> LOCATION: (11)..(11)
<223> OTHER INFORMATION: AMIDATION

<400> SEQUENCE: 25

Ser Asp Ser Phe Lys Ser Gln Ala Arg Gly Gln
1               5                   10

<210> SEQ ID NO 26
<211> LENGTH: 11
<212> TYPE: PRT
<213> ORGANISM: HUMAN
<220> FEATURE:
<221> NAME/KEY: MOD_RES
<222> LOCATION: (11)..(11)
<223> OTHER INFORMATION: AMIDATION

<400> SEQUENCE: 26

Gly Thr Pro Gly Arg Ala Glu Ala Gly Gly Gln
1               5                   10

<210> SEQ ID NO 27
<211> LENGTH: 327
<212> TYPE: DNA
<213> ORGANISM: RAT

<400> SEQUENCE: 27
atgttaaaac tgaatgaacc aaagcctggg gtcgtgacct cggaagaact tacaggatcc    60
ggaatttgga gttctgcttc cgggccaaac tgttcgcaac atcgagatgg ggaagatggc   120
ggctgcggtc gtttcattaa cctcgctggc aacagaaccc aaagaggatg ctttccggaa   180
gcttttccgc ttctacaggc agagccggcg gagtacggcg gacctaggag cggtcatcga   240
cttctcagag gctcacgtgg ctcagagccc gaagcccggc gtgcccaagg tggtcagatt   300
ccctctgaac gtgtcctcag tgactga                                       327

<210> SEQ ID NO 28
<211> LENGTH: 108
<212> TYPE: PRT
<213> ORGANISM: RAT

<400> SEQUENCE: 28

Met Leu Lys Leu Asn Glu Pro Lys Pro Gly Val Val Thr Ser Glu Glu
1               5                   10                  15

Leu Thr Gly Ser Gly Ile Trp Ser Ser Ala Ser Gly Pro Asn Cys Ser
            20                  25                  30

Gln His Arg Asp Gly Glu Asp Gly Gly Cys Gly Arg Phe Ile Asn Leu
```

```
                35                  40                  45
Ala Gly Asn Arg Thr Gln Arg Gly Cys Phe Pro Glu Ala Phe Pro Leu
         50                  55                  60

Leu Gln Ala Glu Pro Ala Glu Tyr Gly Pro Arg Ser Gly His Arg
 65                  70                  75                  80

Leu Leu Arg Gly Ser Arg Gly Ser Glu Pro Glu Ala Arg Arg Ala Gln
                 85                  90                  95

Gly Gly Gln Ile Pro Ser Glu Arg Val Leu Ser Asp
                100                 105

<210> SEQ ID NO 29
<211> LENGTH: 25
<212> TYPE: PRT
<213> ORGANISM: HUMAN
<220> FEATURE:
<221> NAME/KEY: MOD_RES
<222> LOCATION: (25)..(25)
<223> OTHER INFORMATION: AMIDATION

<400> SEQUENCE: 29

Gly Thr Pro Gly Arg Ala Glu Ala Gly Gln Val Ser Pro Cys Leu
1               5                   10                  15

Ala Ala Ser Cys Ser Gln Ala Tyr Gly
            20                  25

<210> SEQ ID NO 30
<211> LENGTH: 13
<212> TYPE: PRT
<213> ORGANISM: HUMAN
<220> FEATURE:
<221> NAME/KEY: MOD_RES
<222> LOCATION: (13)..(13)
<223> OTHER INFORMATION: AMIDATION

<400> SEQUENCE: 30

Arg Glu Gly Arg Arg Asp Ala Pro Gly Arg Ala Gly Gly
1               5                   10

<210> SEQ ID NO 31
<211> LENGTH: 24
<212> TYPE: PRT
<213> ORGANISM: MOUSE
<220> FEATURE:
<221> NAME/KEY: MOD_RES
<222> LOCATION: (24)..(24)
<223> OTHER INFORMATION: AMIDATION

<400> SEQUENCE: 31

Ser Glu Val Asp Ala Arg Arg Ala Lys Lys Ser Leu His Cys Ile Leu
1               5                   10                  15

Ser Asp Thr Ser His Pro Arg Gly
                20

<210> SEQ ID NO 32
<211> LENGTH: 24
<212> TYPE: PRT
<213> ORGANISM: HUMAN
<220> FEATURE:
<221> NAME/KEY: MOD_RES
<222> LOCATION: (24)..(24)
<223> OTHER INFORMATION: AMIDATION

<400> SEQUENCE: 32

Ser Asp Ser Phe Lys Ser Gln Ala Arg Gly Gln Val Pro Pro Phe Leu
1               5                   10                  15
```

```
Gly Gly Val Gly Cys Pro Trp Phe
            20

<210> SEQ ID NO 33
<211> LENGTH: 8
<212> TYPE: PRT
<213> ORGANISM: HUMAN
<220> FEATURE:
<221> NAME/KEY: MOD_RES
<222> LOCATION: (8)..(8)
<223> OTHER INFORMATION: AMIDATION

<400> SEQUENCE: 33

Arg Glu Gly Arg Arg Asp Ala Pro
1               5

<210> SEQ ID NO 34
<211> LENGTH: 21
<212> TYPE: PRT
<213> ORGANISM: RAT
<220> FEATURE:
<221> NAME/KEY: MOD_RES
<222> LOCATION: (21)..(21)
<223> OTHER INFORMATION: AMIDATION

<400> SEQUENCE: 34

Ser Glu Pro Glu Ala Arg Arg Ala Gln Gly Gly Gln Ile Pro Ser Glu
1               5                   10                  15

Arg Val Leu Ser Asp
            20

<210> SEQ ID NO 35
<211> LENGTH: 408
<212> TYPE: DNA
<213> ORGANISM: MOUSE

<400> SEQUENCE: 35
atgaatcgaa accctggagt cgtgaccccg gaagaacctg ccagagccgg aatttcgagt      60
tctgcttccg ggccaaactg ttggcagcct cgagatgggg aagatggcgg ctgctgtggc     120
ttcattagcc acgctggctg cagagcccag agaggatgct tccggaagc ttttccgctt      180 ctaccggcag agccggccgg ggacagcgga cctgggagcc gtcatcgact ctcagaggc      240 gcacttggct cggagcccga agcccggcgt gccccaggta ggaaaggagg agtagtgtgt     300
gccagcctag cggccgactg ggccaccga gactgggccg cctccgggcc ggctttggag      360
ggaagcccct gctgggcctg tccagtgagc tgtaatgtcg agcgatga                   408

<210> SEQ ID NO 36
<211> LENGTH: 135
<212> TYPE: PRT
<213> ORGANISM: MOUSE

<400> SEQUENCE: 36

Met Asn Arg Asn Pro Gly Val Val Thr Pro Glu Glu Pro Ala Arg Ala
1               5                   10                  15

Gly Ile Ser Ser Ser Ala Ser Gly Pro Asn Cys Trp Gln Pro Arg Asp
            20                  25                  30

Gly Glu Asp Gly Gly Cys Cys Gly Phe Ile Ser His Ala Gly Cys Arg
        35                  40                  45

Ala Gln Arg Gly Cys Phe Pro Glu Ala Phe Pro Leu Leu Pro Ala Glu
    50                  55                  60
```

```
Pro Ala Gly Asp Ser Gly Pro Gly Ser Arg His Arg Leu Leu Arg Gly
65                  70                  75                  80

Ala Leu Gly Ser Glu Pro Glu Ala Arg Arg Ala Pro Gly Arg Lys Gly
                85                  90                  95

Gly Val Val Cys Ala Ser Leu Ala Ala Asp Trp Ala Thr Arg Asp Trp
            100                 105                 110

Ala Ala Ser Gly Pro Ala Leu Glu Gly Ser Pro Cys Trp Ala Cys Pro
        115                 120                 125

Val Ser Cys Asn Val Glu Arg
    130                 135
```

<210> SEQ ID NO 37
<211> LENGTH: 20
<212> TYPE: DNA
<213> ORGANISM: Artificial
<220> FEATURE:
<223> OTHER INFORMATION: synthetic

<400> SEQUENCE: 37
aacggaatga atcgaaaccc                                              20

<210> SEQ ID NO 38
<211> LENGTH: 19
<212> TYPE: DNA
<213> ORGANISM: Artificial
<220> FEATURE:
<223> OTHER INFORMATION: synthetic

<400> SEQUENCE: 38
cgctcgacat tacagctca                                               19

<210> SEQ ID NO 39
<211> LENGTH: 20
<212> TYPE: DNA
<213> ORGANISM: Artificial
<220> FEATURE:
<223> OTHER INFORMATION: synthetic

<400> SEQUENCE: 39
gaaagggtgt aaaacgcagc                                              20

<210> SEQ ID NO 40
<211> LENGTH: 20
<212> TYPE: DNA
<213> ORGANISM: Artificial
<220> FEATURE:
<223> OTHER INFORMATION: synthetic

<400> SEQUENCE: 40
ggtaccacca tgtacccagg                                              20

<210> SEQ ID NO 41
<211> LENGTH: 88
<212> TYPE: DNA
<213> ORGANISM: MOUSE

<400> SEQUENCE: 41
aattcggaat gaatcgaaac cctggagtcg tgaccccgga agaacctgcc agagccggaa    60
tttcgagttc tgcttccggg ccaaactg                                      88

<210> SEQ ID NO 42
<211> LENGTH: 88
<212> TYPE: DNA

```
<213> ORGANISM: Artificial
<220> FEATURE:
<223> OTHER INFORMATION: synthetic

<400> SEQUENCE: 42
gatccagttt ggcccggaag cagaactcga aattccggct ctggcaggtt cttccggggt    60
cacgactcca gggtttcgat tcattccg                                      88

<210> SEQ ID NO 43
<211> LENGTH: 9
<212> TYPE: PRT
<213> ORGANISM: HUMAN
<220> FEATURE:
<221> NAME/KEY: MOD_RES
<222> LOCATION: (9)..(9)
<223> OTHER INFORMATION: AMIDATION

<400> SEQUENCE: 43

Pro Gly Arg Ala Glu Ala Gly Gly Gln
1               5

<210> SEQ ID NO 44
<211> LENGTH: 13
<212> TYPE: PRT
<213> ORGANISM: HUMAN
<220> FEATURE:
<221> NAME/KEY: MOD_RES
<222> LOCATION: (13)..(13)
<223> OTHER INFORMATION: AMIDATION

<400> SEQUENCE: 44

Arg Glu Ala Ala Ala Asp Ala Pro Gly Arg Ala Gly Gly
1               5                   10

<210> SEQ ID NO 45
<211> LENGTH: 13
<212> TYPE: PRT
<213> ORGANISM: HUMAN
<220> FEATURE:
<221> NAME/KEY: MOD_RES
<222> LOCATION: (13)..(13)
<223> OTHER INFORMATION: AMIDATION

<400> SEQUENCE: 45

Ala Ala Ala Arg Arg Asp Ala Pro Gly Arg Ala Gly Gly
1               5                   10

<210> SEQ ID NO 46
<211> LENGTH: 13
<212> TYPE: PRT
<213> ORGANISM: HUMAN
<220> FEATURE:
<221> NAME/KEY: MOD_RES
<222> LOCATION: (13)..(13)
<223> OTHER INFORMATION: AMIDATION

<400> SEQUENCE: 46

Arg Glu Gly Arg Arg Asp Ala Pro Gly Arg Ala Ala Ala
1               5                   10

<210> SEQ ID NO 47
<211> LENGTH: 13
<212> TYPE: PRT
<213> ORGANISM: HUMAN
<220> FEATURE:
<221> NAME/KEY: MOD_RES
<222> LOCATION: (13)..(13)
<223> OTHER INFORMATION: AMIDATION
```

```
<400> SEQUENCE: 47

Arg Glu Gly Arg Arg Asp Ala Ala Ala Ala Gly Gly
1               5                   10

<210> SEQ ID NO 48
<211> LENGTH: 228
<212> TYPE: DNA
<213> ORGANISM: HUMAN

<400> SEQUENCE: 48
atggctgttg tgttacttgc accatttggg gacatcagcc aggaaatcac aaaggttggg      60
acagggactc cagggagggc tgaggccggg ggccaggtgt ctccatgcct ggcggcgtcc     120
tgcagtcagg cctatggcgc catcttggct cactgcaacc tctgcctccc aggttcaagt     180
gatctgcctg cctcagcctc ccaaagtgct aggttacagg ttgattaa                  228

<210> SEQ ID NO 49
<211> LENGTH: 75
<212> TYPE: PRT
<213> ORGANISM: HUMAN

<400> SEQUENCE: 49

Met Ala Val Val Leu Leu Ala Pro Trp Gly Asp Ile Ser Gln Glu Ile
1               5                   10                  15

Thr Lys Val Gly Thr Gly Thr Pro Gly Arg Ala Glu Ala Gly Gly Gln
                20                  25                  30

Val Ser Pro Cys Leu Ala Ala Ser Cys Ser Gln Ala Tyr Gly Ala Ile
            35                  40                  45

Leu Ala His Cys Asn Leu Cys Leu Pro Gly Ser Ser Asp Leu Pro Ala
        50                  55                  60

Ser Ala Ser Gln Ser Ala Arg Leu Gln Val Asp
65                  70                  75
```

NEURAL REGENERATION PEPTIDES AND METHODS FOR THEIR USE IN TREATMENT OF BRAIN DAMAGE

RELATED APPLICATIONS

This application is a continuation in part of U.S. patent application Ser. No. 10/225,838 titled "Neural Regeneration Peptides and Methods for Their Use in Treatment of Brain Damage," filed Aug. 22, 2002, Frank Sieg and Paul Hughes, inventors, which claims priority under 35 USC 119(e) to U.S. Provisional Application Ser. No. 60/314,952, filed Aug. 24, 2001, titled "Compositions and Methods for the Treatment of Brain Damage" Frank Sieg and Paul Hughes, inventors, now abandoned. This application also claims priority to U.S. Provisional Application Ser. No: 60/516,018, filed Oct. 31, 2003, titled "Neural Regeneration Peptides and Methods for Their Use," Frank Sieg and Thorsten Gorba, inventors, to U.S. Provisional Application Ser. No: 60/585,041, filed Jul. 2, 2004, titled "Neural Regeneration Peptides: A New Class of Chemoattractive and Neuronal Survival Promoting Peptides," Thorsten Gorba and Frank Sieg, inventors, and U.S. Provisional Application 60/616,271 titled: "Neural Regeneration Peptides and Methods for Their Use in Treatment of Brain Damage," Frank Sieg, Paul Edmond Hughes and Thorsten Gorba inventors, filed Oct. 5, 2004. All of the above applications are incorporated into this application fully by reference.

SEQUENCE LISTING

This application contains a sequence listing presented as (1) a printed copy of the Sequence Listing and (2) a diskette containing the Sequence Listing in computer readable form. The Sequence Listing is incorporated into this application fully by reference.

BACKGROUND

1. Field of the Invention

This invention is directed to compositions and methods for the use of oligonucleotides and peptides that promote neuronal migration, proliferation, survival, differentiation, and/or neurite outgrowth. More specifically, this invention is directed to the use of such peptides in the treatment of brain injury and neurodegenerative disease. This invention also includes new methods for detecting neural cell growth, migration, neurite outgrowth, survival and/or differentiation.

2. Related Art

Mild to severe traumatic brain injury (TBI), and focal or global ischemia can result in significant neuronal cell loss and loss of brain function within a short time period after the insult. There are no treatments currently available to prevent cell death that occurs in the brain as a consequence of head injury or damage caused by disease. To date, there is also no treatment available to restore neuronal function. Treatments available at present for chronic neurodegenerative diseases such as Alzheimer's disease, Parkinson's disease, Huntington's disease and Multiple Sclerosis only target symptoms. No drugs are currently available to intervene in the disease process or prevent cell death.

It is well known that cortical-subcortical non-thalamic lesions can lead to apoptosis within thalamic areas 3-7 days after an insult. Retrograde thalamic degeneration is accompanied by activation of astroglia and microglia in the thalamus (Hermann et al., 2000). Non-invasive techniques like MRI reveal smaller thalamic volumes and increased ventricle-to brain ratio values within TBI patients suffering from non-thalamic structural lesions (Anderson et al., 1996). These findings indicate the high vulnerability of thalamocortical excitatory projection neurons for retrograde-triggered neuronal cell death and therefore indicate the need for a rescue strategy of injured or insulted thalamic neurons.

Functioning of the inhibitory neuronal circuits within the thalamus is crucial for intrathalamic down regulation of neuronal activity within the thalamus as well as within the striatal system. It has been shown that animals with striatal lesions similar to those that occur in Huntington's disease show an improvement in behavioural outcome when GABA-releasing polymer matrices are implanted into the thalamus (Rozas et al., 1996). On a cellular level within the striatum it has been shown that calbindin immunoreactive ("calbindin-ir") inhibitory neurons can be rescued by administering activin A (Hughes et al., 1999).

Until now, only transplantation involving fetal striatal implants lead to an improvement or restoration of motor functions in Huntington's disease animal models (Nakao and Itakura, 2000). Restoring thalamic and striatal GABA-ergic systems that are impaired during Huntington's disease, can improve behavioural outcome (Beal et al., 1986).

A feature of the developing nervous system is the wide-ranging migration of precursor cells to their correct three-dimensional spatial position. These migrations promote differentiation of an array of phenotypes and the arrangement of immature neurons into the vertebrate brain. To achieve the correct wiring of approximately 100 billion neurons, construction of a cellular organisation like the formation of laminar structures in higher cortical regions is necessary (see Hatten and Heintz, 1999 for a review).

A cellular correlate for the direction of movement of a migrating neuron may be the frequency and amplitude of transient $Ca^{2+}$ changes within a single migrating cell (Gomez and Spitzer, 1999) although the triggering of initiation and/or commitment of neuronal cell migration by membrane-bound or diffusible molecules remains elusive.

Many of the cues that are involved in neurite outgrowth and neuronal migration, however, have been identified. Plasma membrane molecules belonging to the integrin receptor family interact with extracellular matrix ligands, like laminin, to initiate neuronal adhesion to the substratum (Liang and Crutcher, 1992; De Curtis and Reichardt, 1993). The control of integrin expression affects a wide range of developmental and cellular processes, including the regulation of gene expression, cell adhesion, neurite outgrowth and cell migration. Other ligands which promote cell migration are cell adhesion molecules (i.e. N-CAM; cadherins; TAG-1), the laminin-like molecule netrin-1, the neuron-glial adhesion ligand astrotactin and growth or neurotrophic factors such as EGF, TGF-α, platelet activating factor and BDNF (Dodd et al., 1988; Yamamoto et al, 1990; Ishii et al., 1992; Ferri and Levitt, 1995; Ganzler and Redies, 1995).

Recently, collapsin-1 (semaphorin3A) was discovered. Collapsin-1 has chemorepulsive activities in axonal guidance and migration patterns for primary sensory neurones (Pasterkamp et al., 2000). In contrast, collapsin-1 acts as a chemoattractant for guiding cortical apical dendrites in neocortical areas (Polleux et al., 2000). Similar chemorepulsive as well as chemoattractive effects on axonal guidance are displayed by slit-1, a diffusible protein (Brose et al., 2000).

Currently, the cascade leading to the initiation of neuronal movement, namely adhesion of the neuron followed by initiation of migration, the process of migration over long distances, including turns and the migration stop signal remains to be elucidated.

Midbrain lesions with simultaneously administered TGF-α lead to a massive proliferation of multipotential stem cells originating in the subventricular zone ("SVZ") and subsequent migration of these progenitor cells into the striatum (Fallon et al., 2000). It may be desirable, however, to activate neuronal proliferation and migration of neurons that are in close vicinity to the site of a lesion in order to prevent long-distance migration of neuronal precursors originating from the SVZ.

There is only one report featuring the chemokine stromal-derived factor (SDF-1) as a neuronal migration chemoattractant. The embryonic expression pattern of SDF-1 attracts cerebellar granule cells to migrate from the external germinal layer to the internal granular layer (Zhu et al., 2002). Nevertheless, this chemokine has no influence on postnatal tissue. There are no known migration-inducing factors that have direct chemoattractive effects on the migration behaviour of neuroblasts or neurons in adults after brain trauma or neurodegenerative disease.

SUMMARY OF THE INVENTION

It is therefore an object of embodiments of the present invention to provide new approaches to the treatment of brain injuries and diseases. Such embodiments include peptides that can induce one or more of neural migration, neural outgrowth, neural proliferation, neural differentiation and/or neural survival. These peptides are herein termed "neural regeneration peptides" or "NRPs." Other embodiments include administration of one or more NRPs following brain injury or during chronic neurodegenerative disease. The term "NRP" or "NRP compound" includes NRPs, NRP homologs, NRP paralogs, NRP orthologs and/or NRP analogs. An NRP can either be administered alone or in conjunction with one or more other NRPs or with other types of agents to promote neural outgrowth, neural migration, neural survival, neural differentiation and/or neural proliferation.

NRPs and related peptides generally have certain amino acid sequences (also termed "domains") present, which confer desirable biological properties on the molecule.

Some embodiments of NRP peptides with certain domains highlighted are shown in Table 1 below.

isoelectric point between about 6.5 and about 10.0, and having at least one biological property promoting an outcome selected from neuronal survival, neurite outgrowth, neuronal proliferation, neuronal differentiation and neuronal migration. Additionally, an NRP may have one or more domains, as indicated in bold in Table 1 above. In some embodiments, an NRP may have a [A]PG[R,S] domain in combination with a PE-domain (e.g., NRP-1 and NRP-2) or alternatively, without a PE-domain (e.g., NRP-5, NRP-7). The presence of a [A]PG [R,S] domain is desirable for NRP biological activity. Additionally a C-terminal GG domain can confer desirable neuroprotective properties on a NRP. Thus, in alternative embodiments, NRPs can have a first domain selected from the group consisting of a [A]PG[R,S] domain, an [A,G]RR domain and an ARG domain have desirable biological activity. In other embodiments, desirably, an NRP can have, in addition to a first domain as described above, a second domain different from the first domain. A second domain can be a PE domain an [A,G]RR domain or a C-terminal GG domain. In certain further embodiments, NRP s can have a third domain of those described above.

Thus, in certain embodiments, an NRP may have a [A]PG [R,S] domain alone, other NRP can have an ARG domain alone, still other NRPs can have an [G,A]RR domain alone. Still other NRPs can have a [A]PG[R,S] domain and a PE domain, and still other NRPs can have a [A]PG[R,S] domain and a [G,A]RR domain. Still other NRPs can have a [A]PG [R,S] domain, an [A,G]RR domain and a PE domain.

Genes of NRP family members contain at least one of a CAAT-Box and a TATA-Box, or both CAAT-Box and TATA-Boxes together in promoter regions. Oligonucleotides derived from NRP family members can be used to increase expression of NRP peptides in regions where such production is desired.

In another aspect, embodiments of this invention provide methods of treatment for damaged areas of the brain as a consequence of head injury or chronic neurodegenerative disease by administering one or more NRPs, NRP analogs (including peptides with structural similarities) and/or NRP prodrugs (including pro-NRP peptides) to promote neuronal or neuroblast migration, proliferation, survival and/or neurite

TABLE 1

Neural Regeneration Peptides*

```
NRP-1:    Y D P E A A S - A P G S G N P - - - - - - C H
NRP-2KG:  K D P E A R R - A P G S L H P - - - - - - C - - L A A - S C S A A G
NRP-3SF:  S D S F K S Q - A R G Q V P P F L G G V G C P W F
NRP-4GG:  G T P G R A E - A G G Q V S P - - - - - - C - - L A A - S C S Q A Y
          G
NRP-5RP2: R E - - G R R D A P G R A - - G G G G - - - - - - A A R S V S P S
          P
NRP-7SW:  S E P E A R R - A P G R K - - - - G G V V C A S L A A D W
NRP-8SG:  S E V D A R R - A K K S L H - - - - - - - C - I L S - D T S H P R G
NRP-9SD:  S E P E A R R A Q G G Q I P S E R V L S D
```

In some embodiments, NRPs generally comprise a chain length of between about 8 to about 25 amino acids and having molecular weights between about 0.8 and about 2.7 kDa. Additionally, in other embodiments, an NRP can have an outgrowth. This method of treatment may be particularly useful but in no way limited to, patients suffering from mild to severe traumatic brain injury (TBI) that involves neocortical damage as well as injuries to subcortical areas.

In one embodiment, NRP-2 (SEQ ID NO:5) is encoded by a nucleic acid sequence localised on human chromosome 13 within the genomic clone bA87G1 (Sanger Sequencing Centre) on the reverse strand between base pairs 77232-76768. This peptide has functions similar to those of rat NRP-1 and can promote neuronal survival, neuronal differentiation, neuronal proliferation, neuronal migration and neurite outgrowth.

In another embodiment, NRP-3 (SEQ ID NO:7) is encoded by a nucleic acid sequence localized on the reverse strand of chromosome 3 in the human genome, between base pairs 34764-33003 according to Double Twist annotation. This NRP also can promote neuronal survival, neuronal differentiation, neuronal proliferation, neuronal migration or neurite outgrowth.

In still another embodiment, NRP4 (SEQ ID NO:9) is encoded by a nucleic acid sequence located between base pairs 21970003-21972239 on the forward strand of human chromosome 15, according to the NCBI human genome annotation project. Peptides translated from that nucleic acid sequence also belong to the human family of NRPs. Peptides encoded by this sequence can promote neuronal survival, neuronal differentiation, neuronal proliferation, neuronal migration or neurite outgrowth.

A still further embodiment, NRP-5 (SEQ ID NO:11), is encoded by a nucleic acid sequence localized on the reverse strand of human chromosome 7, in the region between base pairs 15047153-14824042, as denoted by the NCBI annotation. Peptides encoded by this sequence can promote neuronal survival, neuronal differentiation, neuronal proliferation, neuronal migration or neurite outgrowth.

Another embodiment of an NRP has been annotated, with a DNA sequence from the human genome located in the region 116668725-116667697 on the reverse strand of chromosome 6 (region according to NCBI human genome annotation project). The resulting peptide, NRP-6 (SEQ ID NO:13), can promote neuronal survival, neuronal differentiation, neuronal proliferation, neuronal migration or neurite outgrowth.

Yet further embodiments of NRPs are found in rodents. A mouse NRP is encoded by a nucleic acid sequence located within the arachne contig_191157 of NCBI consisting of 339 nucleic acids using reading frame 1. Within an overlapping region, there is a second ORF of 198 nucleic acids starting at position 29 of an annotated NRP using frame 3. This ORF codes for a protein with high identity to a truncated human DNA repair protein. The resulting peptide, NRP-7 (SEQ ID NO:17 can promote neuronal survival, neuronal differentiation, neuronal proliferation, neuronal migration or neurite outgrowth.

A still further embodiment is NRP-8 (SEQ ID NO:20), which is also a mouse peptide encoded by a nucleic acid sequence located within the genomic clone bM344E9 of the mouse Sanger database on the reverse strand. The protein coding sequence has been annotated and is located between base pairs 5609-4052. NRP-8 can promote neuronal survival, neuronal differentiation, neuronal proliferation, neuronal migration or neurite outgrowth.

A still further embodiment is NRP-9 (SEQ ID NO:28) is a rat orthologue NRP of the mouse NRP-7 (SEQ ID NO:17) and is encoded by a nucleic acid sequence located on the reverse strand of rat chromosome 6 in the following exons: exon 1 located in position 7022614-7022326 and exon 2 located in position 7018685-7018651 (NCBI database). NRP-9 can promote neuronal survival, neuronal differentiation, neuronal proliferation, neuronal migration or neurite outgrowth.

In another aspect, the invention includes embodiments for in vitro bioassays for evaluating proliferative and migration-inducing activity. Until recently, there were few in vitro neuronal migration assays available that could detect migrating untagged neurons over a prolonged time-period. One of these bioassays monitors olfactory peripheral placode cells organized as organotypic tissue cultures ("OTCs") during a 5-day time course (Fueshko and Wray, 1994). In certain embodiments of this invention, by using in vitro bioassay using adult thalamocortical OTCs," NRPs can be evaluated for their ability to induce neuronal migration, neuronal proliferation, neuronal differentiation, neuronal survival and/or neurite outgrowth. These embodiments can be particularly useful because 1) under control conditions, formation of a cell-bridge between both cultivated organs (e.g., thalamus and cortex) can be avoided by physically separating the two organs sufficiently far from each other (about 3 to about 5 mm) on a tissue culture substrate and 2) because after birth, intrathalamic neuronal migration has been substantially completed due to the time course of thalamic ontogenesis. These bioassays can therefore be well suited for broad screening and identification of neuronal migration-inducing factors.

In certain embodiments of an in vitro thalamocortical OTC assay includes the advantages of revealing both radial migration within the cortex and induced tangential migration within the thalamus. Under in vitro control conditions, only intrinsic cortical radial migration can be observed because of the normal time course of ontogenetic development of the neocortex.

In other embodiments, in vitro bioassays are provided that involve cerebellar microexplants adhered to substrates. These embodiments can be used to provide data regarding patterns of neuronal migration, including quantifying the numbers of migrating neurons and the distance of migration in respect of the microexplant.

A developing migration-chain consisting of small neurons (such as inhibitory granule cells) as well as an overall enhancement of cell migration can be observed after as little as 2-3 days of cultivation. This assay result resembles the cell chain induction within thalamocortical OTCs.

Embodiments of another aspect of the invention include the use of NRPs to treat or or prevent neurodegenerative diseases and brain injuries. In particular, NRPs are particularly suitable for use in brain regions lacking quiescent neuronal stem cells near the area of injury or disease.

Use of NRPs as preventative agents can find use in elective surgeries, such as coronary artery bypass graft (CABG) procedures or other procedures involving a compromise of oxygen delivery to the brain. Moreover, NRPs can be useful in treating acute brain injuries caused by, for example, stroke, trauma or other injury that compromises oxygenation of the brain or spinal cord. Additionally, prophylactic treatment can be carried out before radiotherapy or chemotherapy.

NRP compounds are capable of initiating neuronal proliferation, neuronal migration, neuronal survival and/or neurite outgrowth within postnatally differentiated neural tissue. These properties can be exploited in treatment strategies aimed at improving or repairing neuronal circuits within impaired areas of patients with mild to severe traumatic brain injury ("TBI"), including diffuse axonal injury, hypoxic-ischemic encephalopathy and other forms of craniocerebral trauma. NRP compounds can be used to treat infections of the nervous system, such as common bacterial meningitis, and to treat strokes including those caused by ischemic infarction, embolism and haemorrhage such as hypotensive haemorrhage or other causes. Moreover, NRP compounds can be useful for the treatment of neurodegenerative diseases including Alzheimer's disease, Lewy Body dementia, Parkinson's disease (PD), Huntington's disease (HD), multiple sclerosis, motor neuron disease, muscular dystrophy, peripheral neuropathies, metabolic disorders of the nervous system including glycogen storage diseases, and other conditions where neurons are damaged or destroyed.

In certain embodiments of this invention, we found that members of the NRP gene family are expressed in mammalian stem cells, both in immortalized stem cells and in primary cultures of stem cells.

In other embodiments, we found that NRPs can promote differentiation of stem cells into neural progenitor cells (neuroblasts). In still other embodiments, NRPs can stimulate migration of stem cells in response to chemoattractants, can promote differentiation of neuroblasts into cells having morphology of mature neurons (e.g., axons), and can promote the growth of neurites (e.g., axons and dendrites) from differentiated neuroblasts.

Embodiments of other aspects of the invention include use of NRPs to increase proliferation of olfactory cells.

Thus, NPRs can be important therapeutic tools to repair injured nerve cells, to cause repopulation of neural tissue, to aid in differentiation of neurons or to aid in processes necessary to promote synaptogenesis (e.g., neurite outgrowth and/or neural differentiation).

In other embodiments, surgical implantation of stem cells in combination with an NRP can be used to repopulate neural tissues. The combination of stem cells or alternatively, neuroblast cells, along with an NRP can promote the regrowth of neural tissue. Such procedures can lead to reformation of mature neural tissues, and therefore can be used to treat neurodegenerative conditions. Such conditions including hypoxia/ischemia, stroke, cardiac graft bypass surgery, Alzhemier's disease, Parkinson's disease, Huntington's disease, amyotrophic lateral sclerosis, multiple sclerosis, and other disorders involving death or degeneration of neural cells.

BRIEF DESCRIPTION OF THE FIGURES

The patent or application file contains at least one drawing executed in color. Copies of this patent or patent application publication with color drawing(s) will be provided by the office upon request and payment of the necessary fee. This invention will be described by way of description of particular embodiments thereof. Other objects, features and advantages of embodiments of this invention will become apparent from the specification and the figures, in which:

FIG. 3A shows an overview of two migrating cell chains. The upper neuronal cell chain had completed its way to the cortex while the lower one had reached half way to the cortical tissue. The neuronal origin of the cell chain was verified by the MAP-2 expression pattern of the migrating cells, as shown in FIGS. 3B to 3D. Double arrows in FIGS. 3A and 3B indicate the same locations in the OTC. In FIGS. 3C and 3D, the micrograph of the migrating cell chain was taken near the cortical tissue. Bars: 500 μm (FIG. 3A); 100 μm (FIGS. 3B to 3D).

In FIG. 4D the onset of migration of thalamic cells is shown (lower right panel). Black arrows indicate nuclei while the white arrows point to the leading process of the migrating cells. Bars: 500 μm (FIGS. 4A and 4B); 100 μm (FIG. 4C); 80 μm (FIG. 4D).

FIG. 7A (upper left panel) shows that two thalamocortical connections (arrows) have been established revealing MAP2-positive cells. The white square in FIG. 7A indicates the area of a cell stream shown in FIG. 7B shown at greater magnification. FIG. 7B (upper right panel) shows the cell stream having bipolar-shaped parvalbumin-positive neurons migrating in a track-like arrangement. FIG. 7C (middle left panel) shows MAP2-positive neurons close to the origin of the thalamic cell stream. The cell stream has ordered positioning of the neuronal soma. The primary neurites project to the axonal layer in the middle of the cell-bridge (small arrows). FIG. 7D (middle right panel) shows BrdU-positive proliferating cells (arrows) located in the habenula, the generated thalamocortical cell bridge, and within cortical layers. The white ovals indicate regions of high proliferation. FIG. 7E (lower left panel) shows BrdU-positive cells within the cell-bridge. A subpopulation (arrows) is co-localised with parvalbumin as shown in FIG.

7F (lower right panel; arrows in FIG. 7F). Bars: 500 μm (FIGS. 7A and 7D); 100 μm (FIGS. 7B, 7E and 7F); 50 μm (FIG. 7C).

Figure 8:
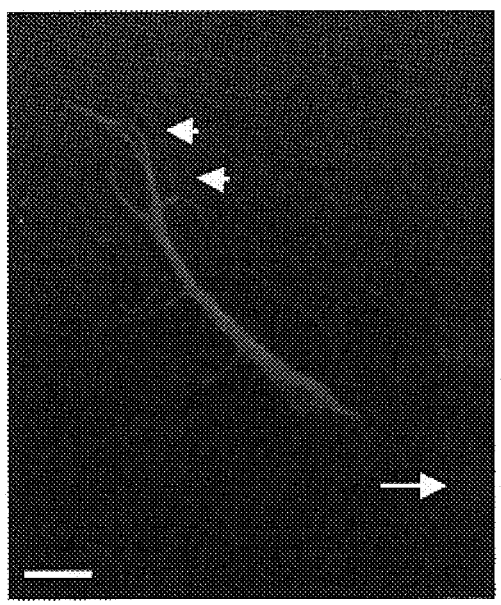

FIG. 8 is a photomicrograph showing enhancement of cellular expression of MAP-2 and correlation to the migration process. MAP-2 expression was observed within the apical neurite of the migrated cortical neuron, which was the leading process at the initiation of migration. The white arrow at the lower right portion of FIG. 8 indicates the location of cortical layer I about 500 μm away. Note the existence of secondary and tertiary dendrites (white arrowheads at upper left of FIG. 8). Bar: 40 μm.

Figure 9:
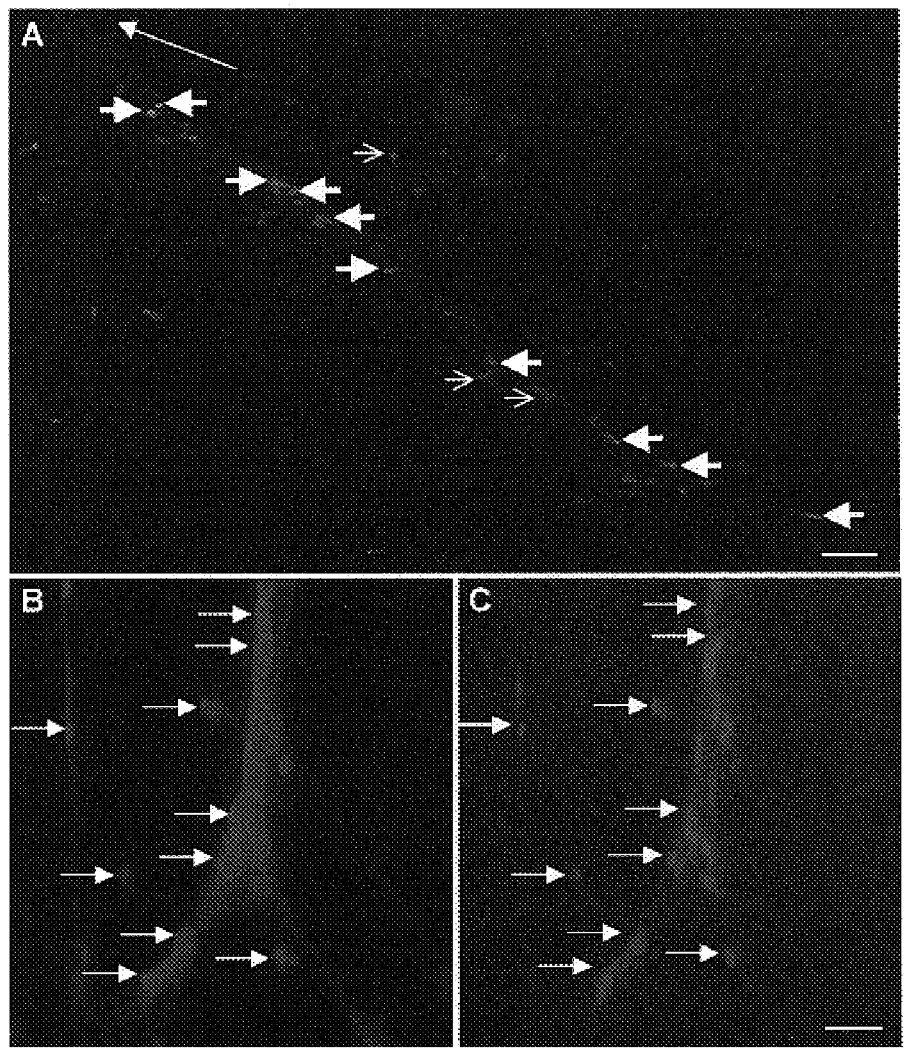

FIG. 9 is a series of photomicrographs showing proliferation and migration of parvalbumin-ir thalamic neurons between the thalamic and cortical tissue of the thalamocortical co-cultures. Thalamocortical OTCs were supplemented with 3 nM of highly purified NRP-1 (SEQ ID NO: 2) and BrdU for 24 hours and fixed following 4 days in vitro ("DIV"). FIG. 9A shows a confocal image revealing that the migrating cell stream contained proliferating neuronal cells positive for parvalbumin and BrdU (indicated by thick white arrows). Some neurons were only positive for parvalbumin (thin arrows). The long white arrow points to the location of the thalamic tissue. FIGS. 9B and 9C show that most of parvalburnin-ir cells (FIG. 9B) within the migrating stream were proliferating (FIG. 9C; arrows). Note the immunoreactivity of the fibres once again confirmed that the neurons "travelled" along neuronal fibres. Bars: 100 μm (FIG. 9A); 50 μm (FIGS. 9B and 9C).

Figure 10:
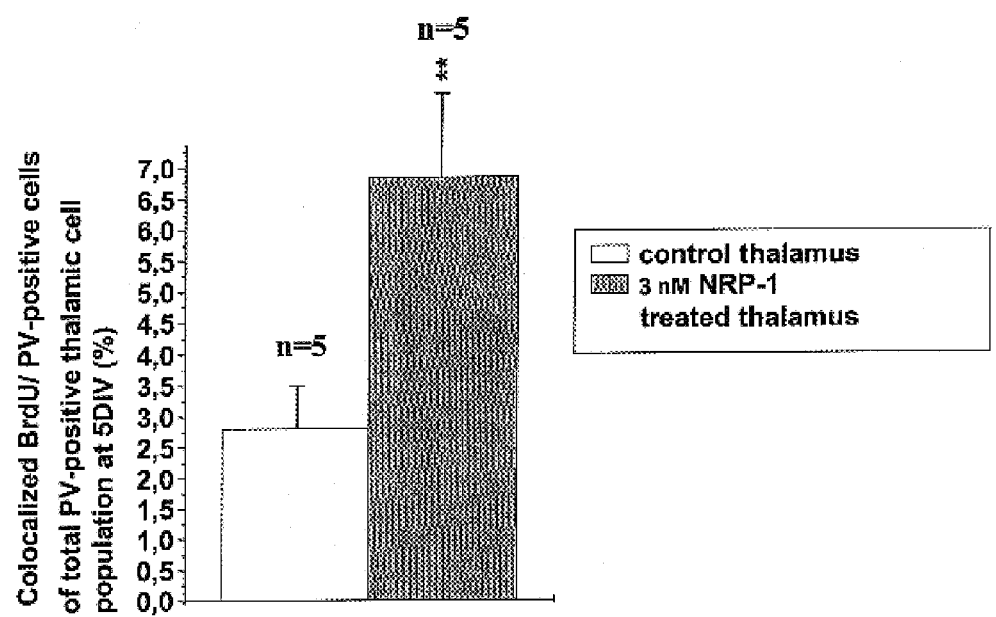

FIG. 10 depicts a graph showing quantitative analysis of proliferation initiation within thalamic parvalbumin-ir neurons. BrdU and 3 nM NRP-1 (SEQ ID NO: 2) were administered at the start of co-culturing. The medium was changed after 24 hours. Co-localisation of parvalbumin and BrdU was determined after 5 days in vitro within the thalamic tissue, which included the habenula nucleus, the lateral geniculate nucleus, the nucleus reticularis thalami and thalamic midline nuclei. 6.8% of the total parvalbumin-ir thalamic population was of proliferative character. NRP-1 (SEQ ID NO: 2) induced statistically significant induction of proliferation compared to the control thalamus treated with vehicle without NRP-1. N represents the number of assessed thalamic tissues.

Figure 11:
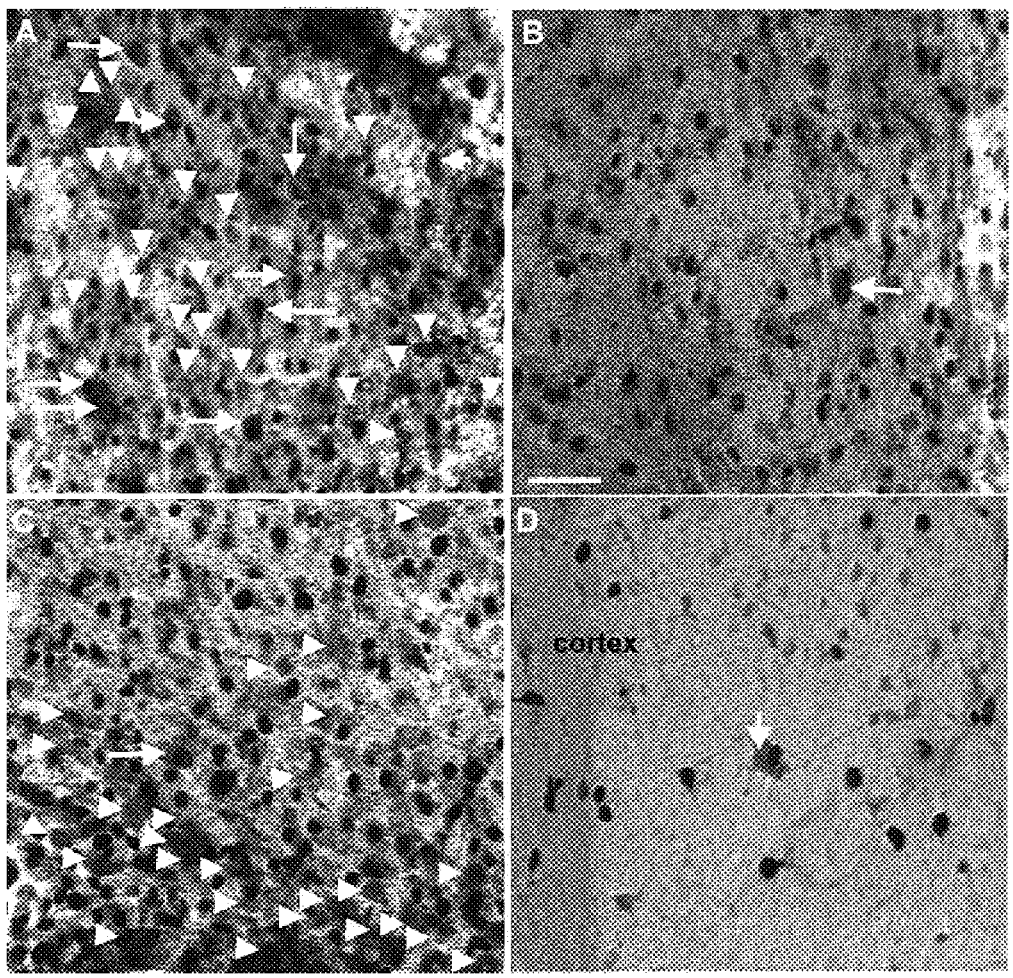

FIG. 11 depicts proliferated parvalbumin-ir cells within thalamic tissue. 5 days after NRP-1 (SEQ ID NO: 2) administration, there was a distinct induction of proliferation of parvalbumin-ir cells (white arrows) within central areas of the thalamus. The majority of parvalbumin expressing cells remained non-proliferative (arrow heads in FIG. 11A). Inside the habenula nucleus, only a minority of parvalbumin expressing cells are double labelled with BrdU (FIG. 11B). In vehicle treated cultures double-labelled with BrdU and parvalbumin, cells expressing both markers were found very rarely (arrow in FIG. 11C). FIG. 11D indicates a migrated calretinin/BrdU-positive cell near cortical layer VI. Bar: 50 μm.

Figure 12:
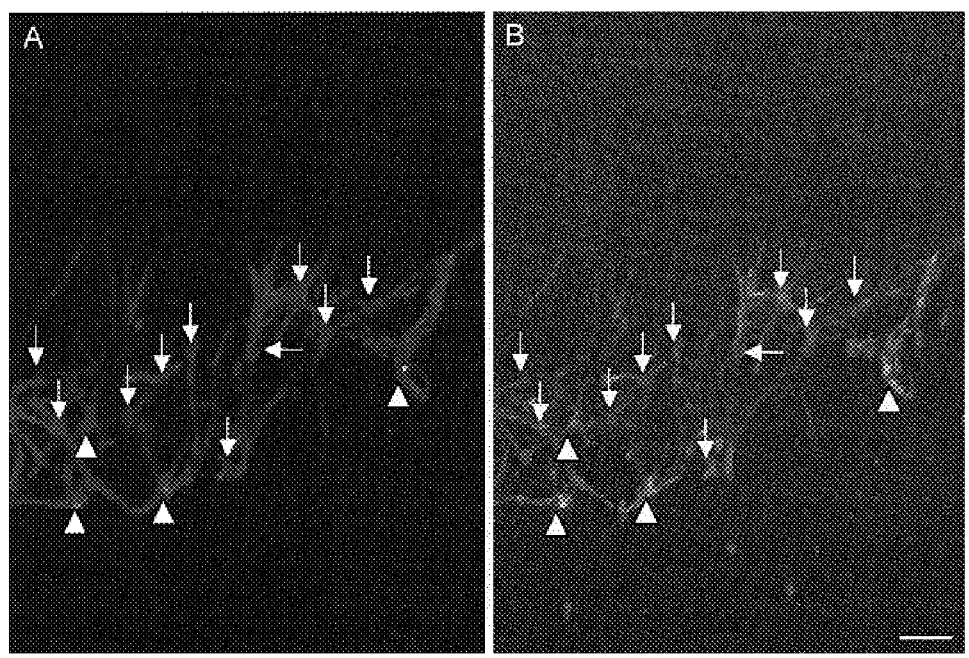

FIG. 12 depicts the specificity of the proliferation induced by NRP-1 (SEQ ID NO: 2). We tested the proliferation status of astroglia by monitoring the expression patterns for GFAP and BrdU-incorporation. Thalamocortical OTCs were supplemented with 3 nM highly purified migration-inducing factor and fixed following 4 days in vitro. FIG. 12A (left panel) depicts non-proliferative GFAP-positive astrocytes (white arrows) accompanying the neuronal migration stream, with a subpopulation of astrocytes of proliferative character (FIG. 12B, right panel; white arrow heads). Approximately 30% of the astrocytes in close vicinity to the neuronal migration stream were of proliferative character. Bar: 50 μm.

Figure 13:
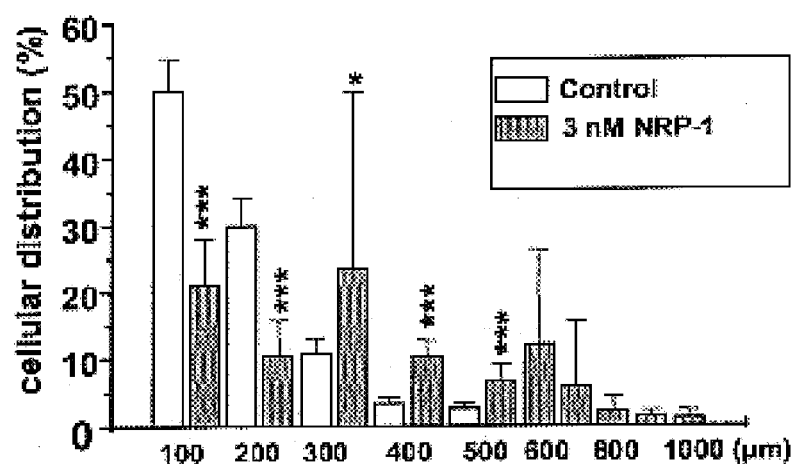

FIG. 13 depicts quantification of induction of cerebellar migration. Two days after NRP-1 (SEQ ID NO:2) administration, there was an induction in cerebellar cell migration. Most of the cells were distributed between 200-300 μm from the cerebellar margin. A significant population of cells was distributed about 500-600 μm away from the margin. Cells from vehicle-treated cultures revealed a maximal distribution of 300 μm. The experimental data was derived from nine evaluated microexplants originating from three different cultures.

Figure 14:
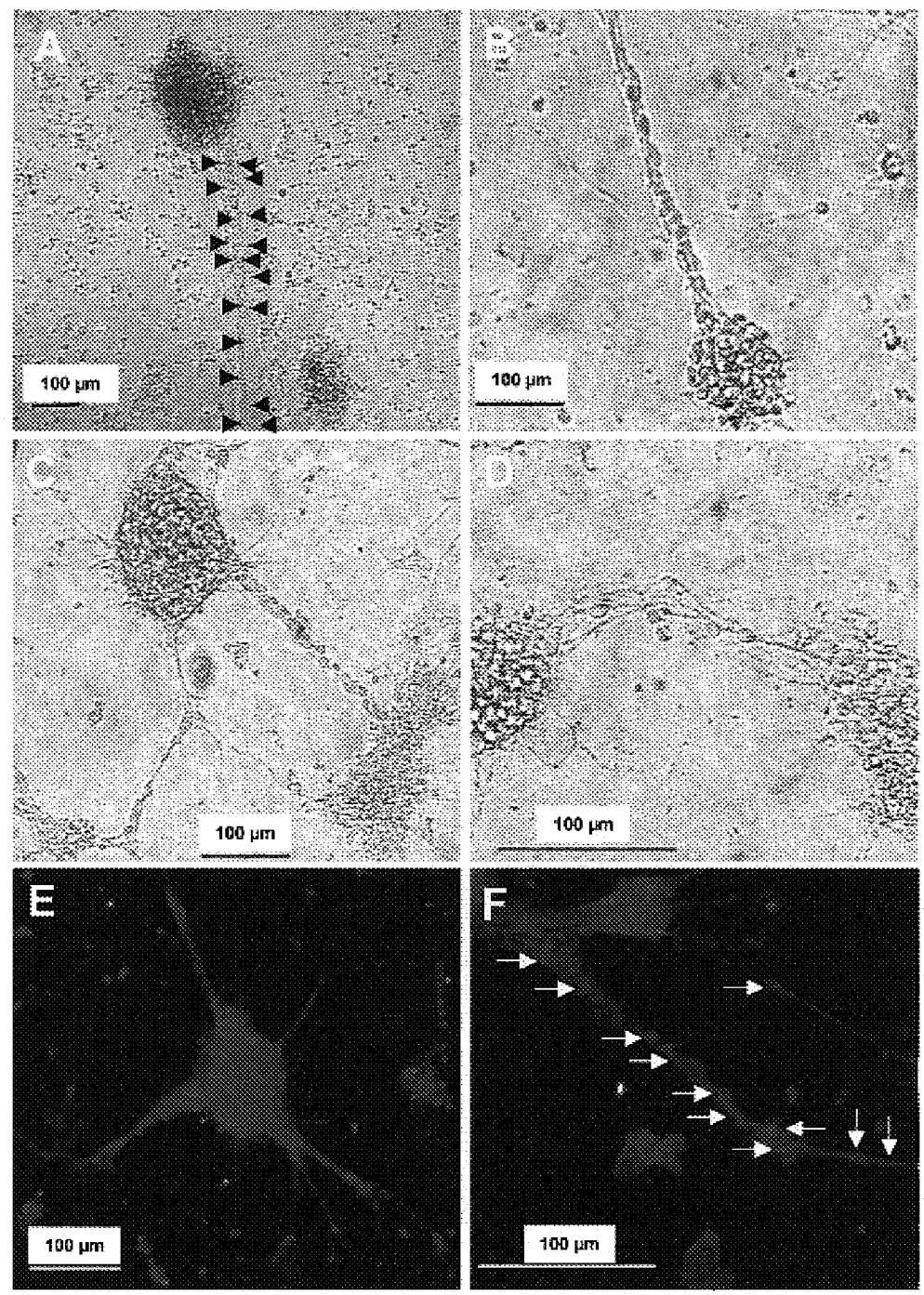

FIG. 14 depicts neuronal migration within cerebellar microexplants. The microexplants were supplemented with 75 nM purified NRP-1 (SEQ ID NO:2) within the first 3 h settling time on cover slips. At start of co-culturing (addition of cell medium) NRP-1 was added to produce to a final concentration of 3 nM. FIG. 14A shows that there was migration of mostly small cells (10-15 μm in diameter) and an enhanced neurite outgrowth originating from the microexplant. Migrating cells having diameters greater than 15 μm are indicated by arrowheads. Small inhibitory neurons migrated as a migrating cell stream (FIGS. 14A, 14B and 14C) in a more or less loosely arranged on a neuritic network (FIG. 14D) interconnecting microexplants. FIGS. 14E and 14F depict expression of MAP-2. Arrows in FIG. 14F indicate migrating neurons.

Figure 15:
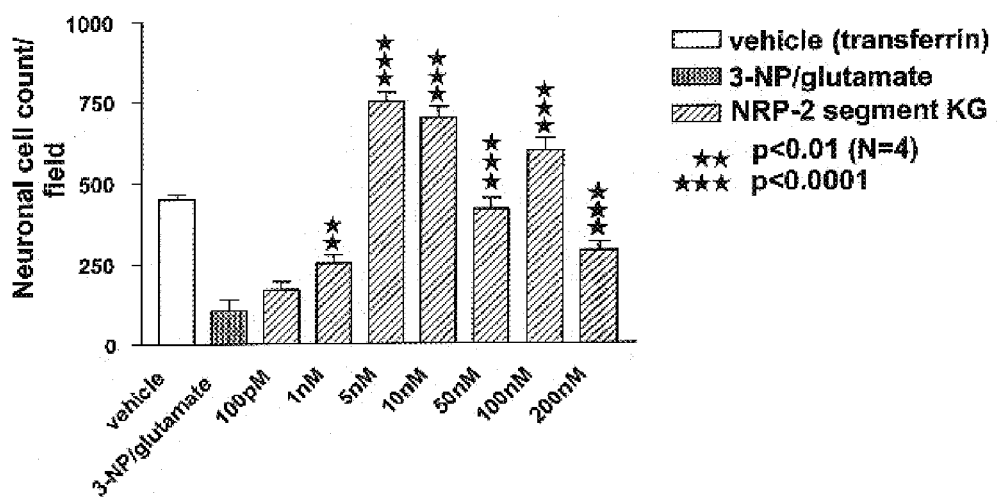

FIG. 15 depicts results of a survival assay with NRP-2 segment KG (SEQ ID NO: 18) using a pre-incubation method. Cerebellar microexplants were pre-incubated for 15 hrs with NRP-2 segment KG (SEQ ID NO: 18) and subsequently were injured by exposure to 3-NP/glutamate for 9hrs. After 72 hours, neuronal survival was evaluated by counting cells displaying neurite outgrowth. At each concentration studied, NRP-2 KG at least partially reversed the effects of 3-NP/glutamate, with statistically significant effects observed a all concentrations above 1 nM. Concentrations of NRP-2 segment KG of 5 nM to 100 nM fully reversed the effect of the injury. At concentrations of 5 nM, 10 nM and 100 nM, NRP-2 segment KG induced proliferation of the cultured neurons in the presence of 3-NP/glutamate to an extent greater than vehicle in the absence of 3-NP/glutamate.

Figure 16:
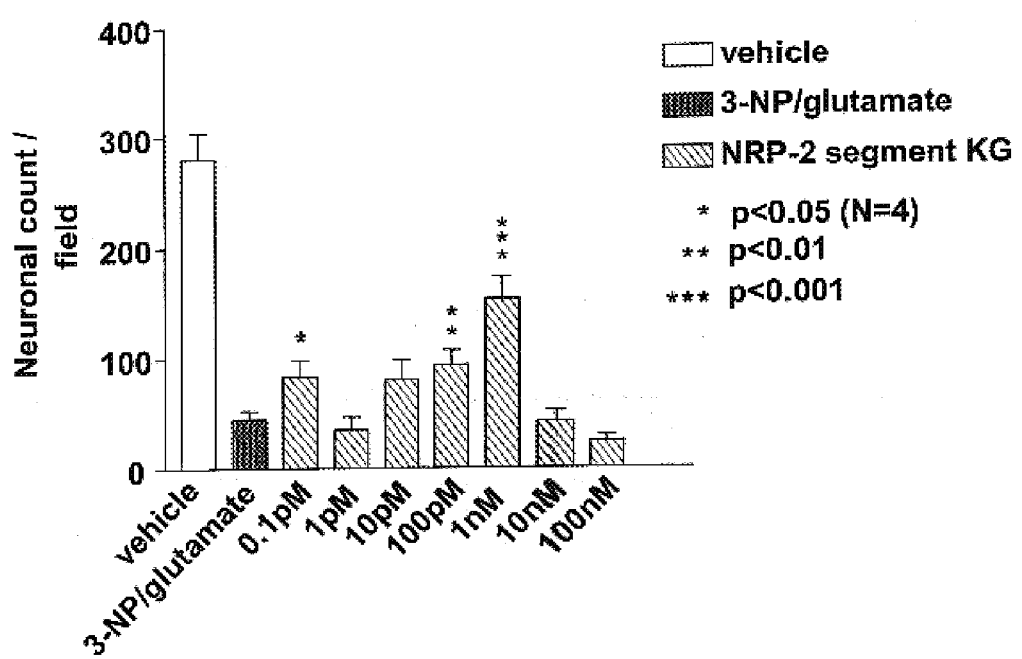

FIG. 16 depicts results of a survival assay with NRP-2 segment KG (SEQ ID NO: 18). Cerebellar microexplants were injured using 3-NP/glutamate and were rescued by simultaneously added NRP-2 segment KG (SEQ ID NO: 18). After 48 hrs, neuronal survival was evaluated by counting cells displaying neurite outgrowth. The maximal biological activity for survival of NRP-2 segment KG (SEQ ID NO: 18) was found to be at concentrations between 100 μM and 1 nM.

Figure 17:
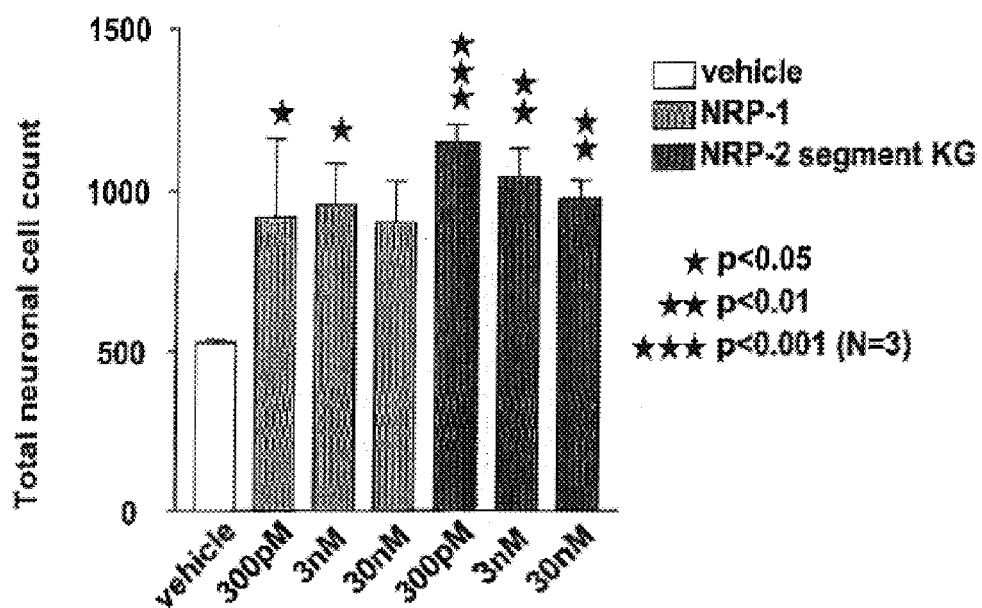

FIG. 17 depicts results of proliferation induction without injury using NRP-2 segment KG (SEQ ID NO: 18) and rat NRP-1 (SEQ ID NO: 2). Peptides were administered 24hrs after start of cultivation to decrease interference in the assay due to initial neuronal survival or adherence effects. The cultures were fixed after 3 days in vitro. There was neuronal proliferation seen at 300 μM of NRP-2 segment KG (SEQ ID NO: 18).

Figure 18:
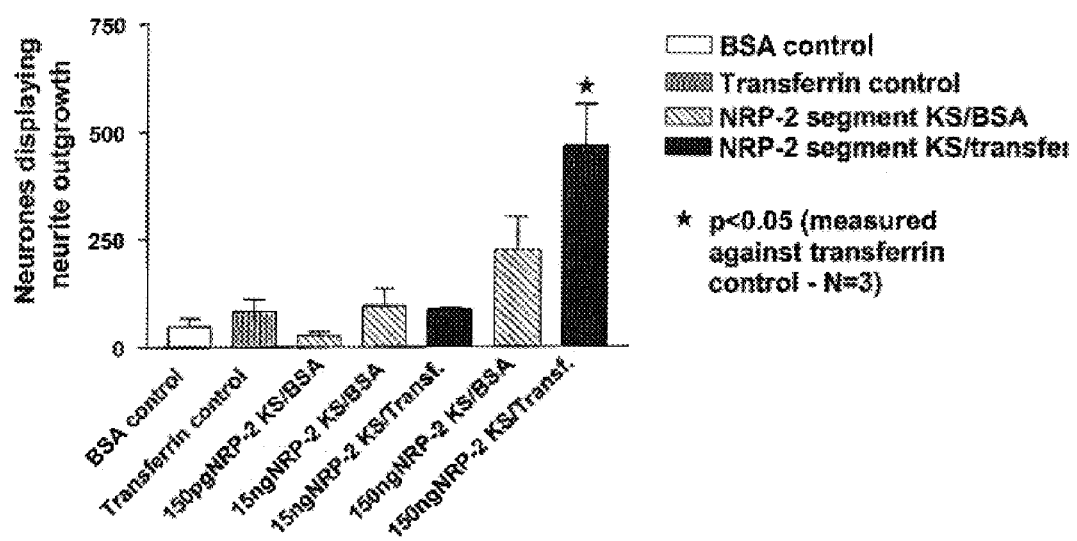

FIG. 18 depicts results of a haptotactic migration assay using NRP-2 segment KS (SEQ ID NO: 23). The NRP-2 segment KS (0.01 μg/ml and 0.1 μg/ml) was diluted in 10 μg/ml BSA or 10 μg/ml human transferrin, respectively. Culture plates were coated with NRP-2 segment KS (SEQ ID NO: 23) was subsequently followed by 100 μg/ml PDL coating. Striatal cells were seeded into PDL-coated inserts and migration behaviour was measured after 48 hrs. There was substantial migration induction of striatal neurons when culture dishes were coated with 150 ng of NRP-2 segment KS (SEQ ID NO: 23).

Figure 19:
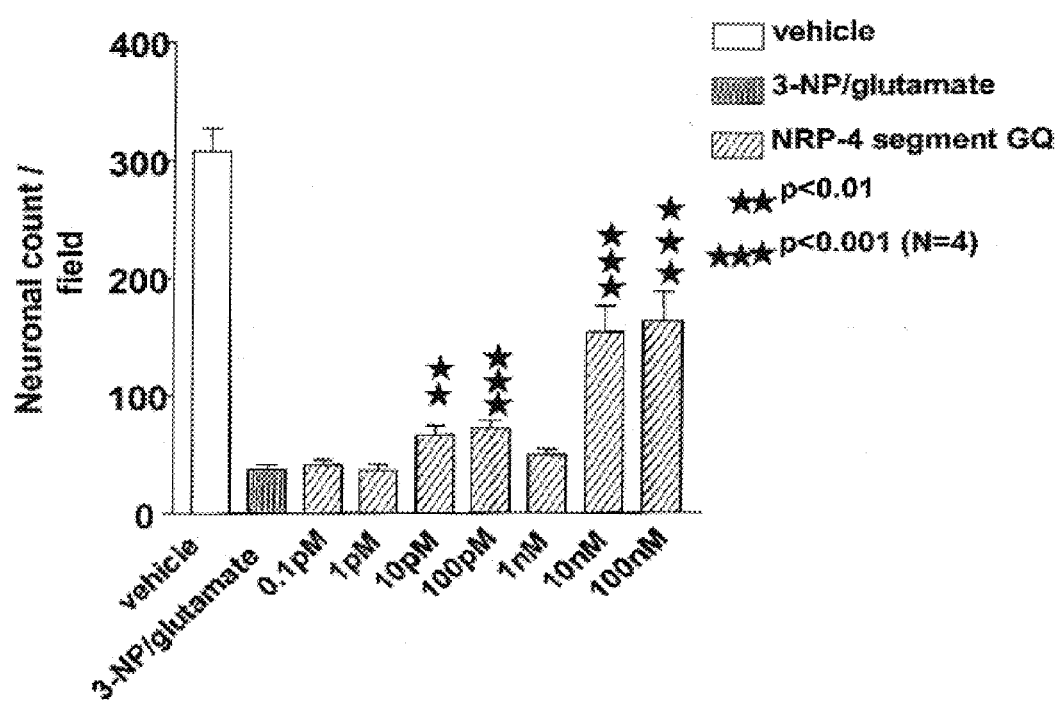

FIG. 19 depicts results of a survival study with human NRP4 segment GQ (SEQ ID NO: 26). Cerebellar microexplants were injured by 3-NP/glutamate and rescued by simultaneous addition of NRP-4 segment GQ (SEQ ID NO: 26). After 48 hrs, neuronal survival was evaluated by counting cells displaying neurite outgrowth. The maximal biological activity of NRP-4 segment GQ was observed to be between 10 nM and 100 nM, although statistically significant effects were observed at concentrations of 10 pM, 100 pM, 10 nM and 100 nM.

Figure 20:
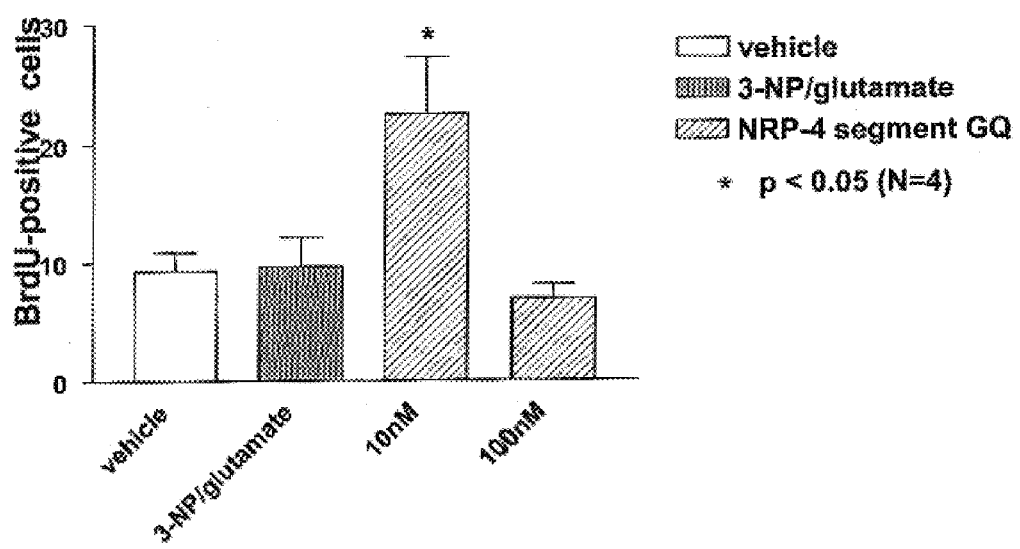

FIG. 20 depicts results of studies on proliferation induction under injury conditions using NRP-4 segment GQ. Cerebellar microexplants were injured by 3-NP/glutamate. NRP-4 segment GQ (SEQ ID NO: 26) and BrdU were administered simultaneously for 24 hrs. After 72 hrs, BrdU-positive nuclei were counted in four microscopic fields for each culture. Proliferation induction was observed at a 10 nM concentration of the peptide.

Figure 21:
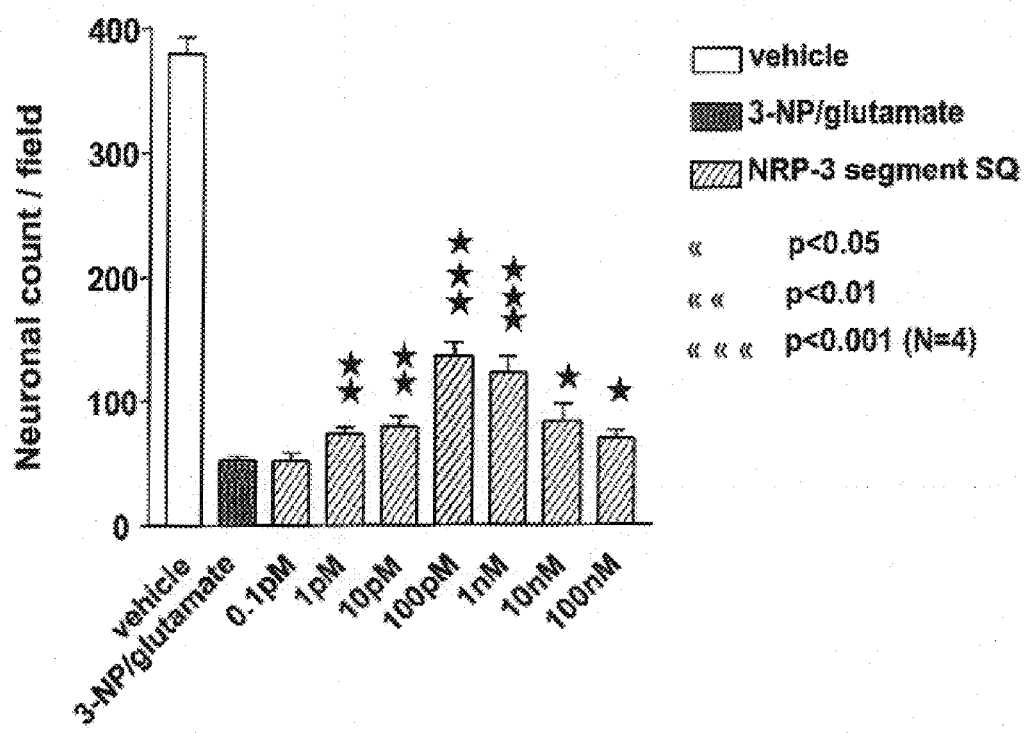

FIG. 21 depicts results of a survival assay with NRP-3 segment SQ (SEQ ID NO: 25). Cerebellar microexplants were injured by 3-NP/glutamate and simultaneously rescued by NRP-3 segment SQ (SEQ ID NO: 25). After 48 hrs, neuronal survival was evaluated by counting cells displaying neurite outgrowth. Maximal biological activity of NRP-3 for survival was between 100 µM and 1 nM.

Figure 22:
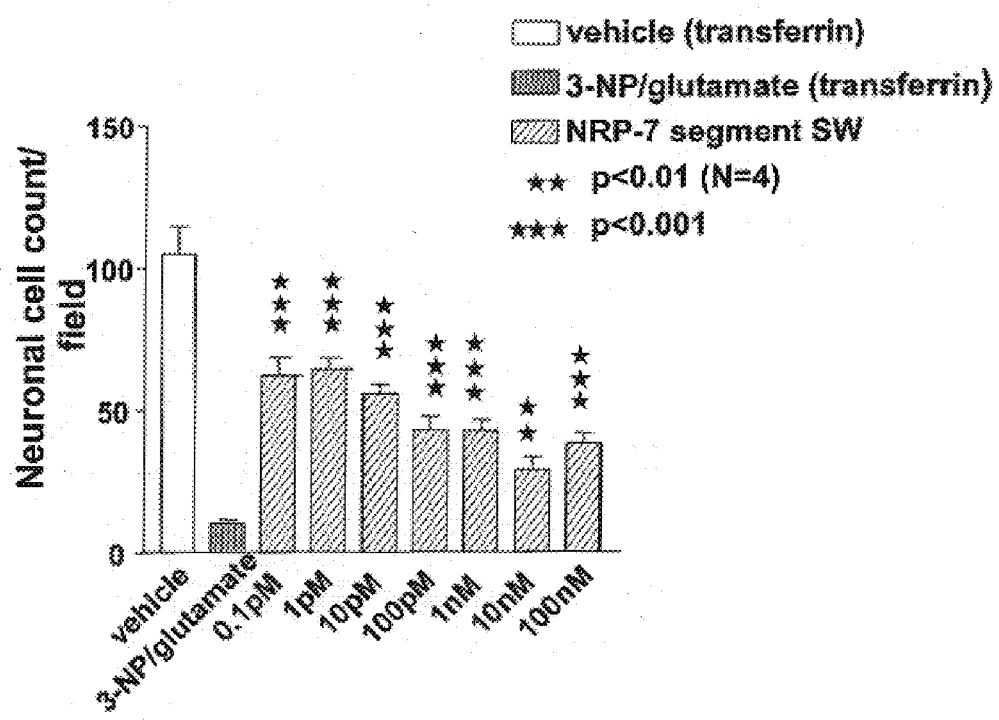

FIG. 22 depicts results of a survival assay with mouse NRP-7 segment SW (SEQ ID NO: 24). Cerebellar microexplants are injured by 3-NP/glutamate and simultaneously rescued by mouse NRP-7 in the presence of human transferrin. After 48 hrs neuronal survival was evaluated by counting cells displaying neurite outgrowth. Maximal biological activity of NRP-7 segment SW (SEQ ID NO: 24) for survival was observed to be between 0.1 pM and 1 pM.

Figure 23A:
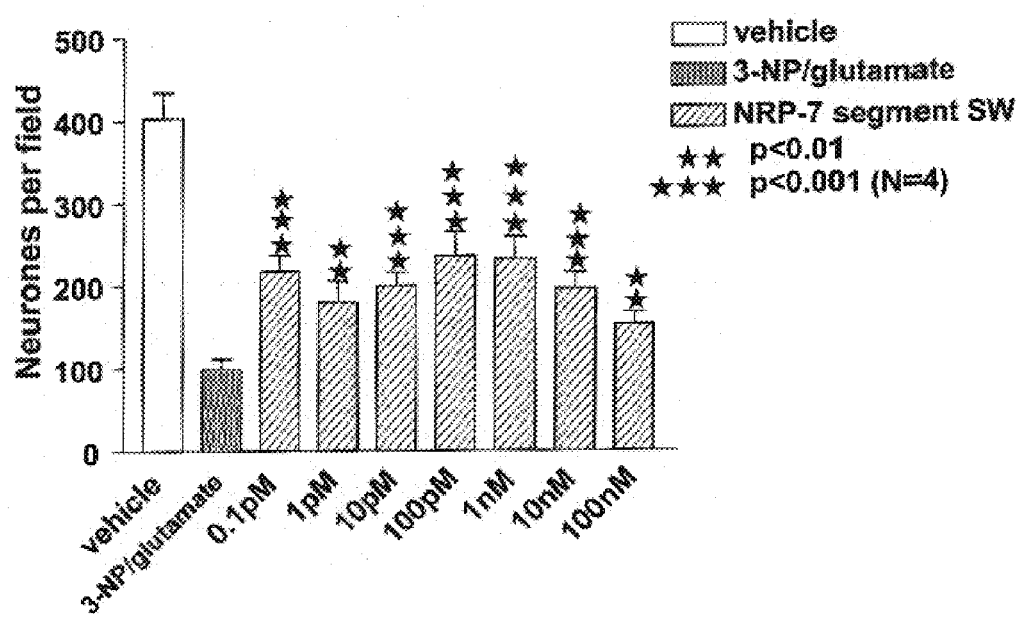

FIG. 23A depicts results of a survival assay with mouse NRP-7 segment SW (SEQ ID NO:24). Cerebellar microexplants were injured by 3-NP/glutamate and simultaneously rescued by NRP-7 segment SW (SEQ ID NO: 24) without transferrin. After 48 hrs neuronal survival was evaluated by counting cells displaying neurite outgrowth. Maximal biological activity of NRP-7 segment SW (SEQ ID NO:24) for survival was between 100 pM and 1 nM.

Figure 23B:
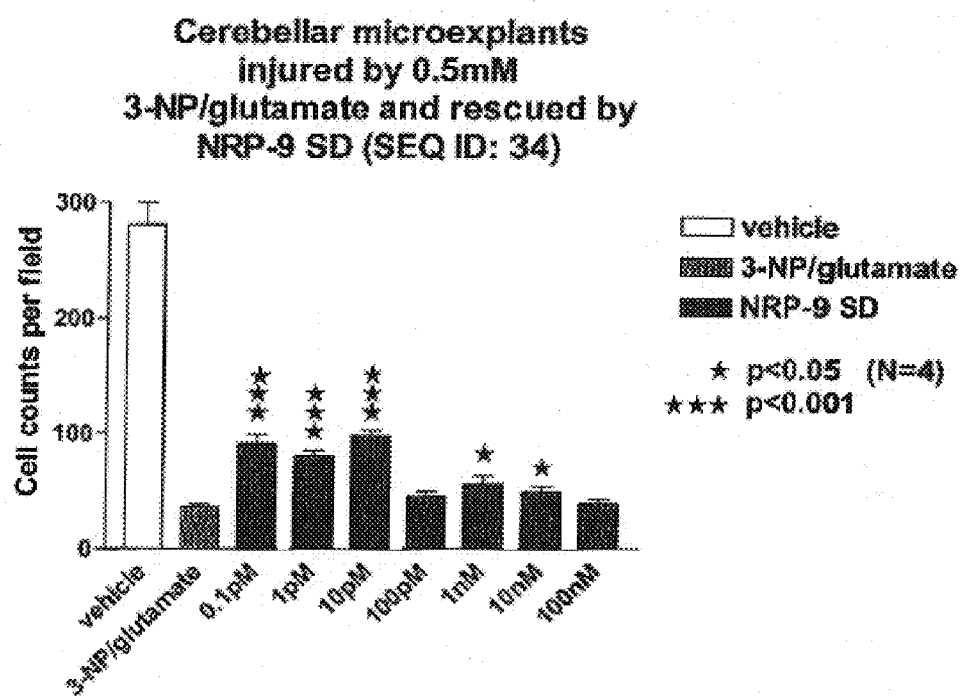

FIG. 23B depicts results of a survival assay with rat NRP-9 segment SD (SEQ ID NO:34). Cerebellar microexplants were injured by 0.5 mM 3-NP/glutamate and rescued by NRP-9 SD (SEQ ID NO:34) without transferrin. After 48 hrs neuronal survival was evaluated be counting cells displaying neurite outgrowth. Maximal biological activity for survival of NRP-9 segment SD (SEQ ID NO:34) was observed at concentrations between 0.1 pM and 10 pM.

Figure 24:
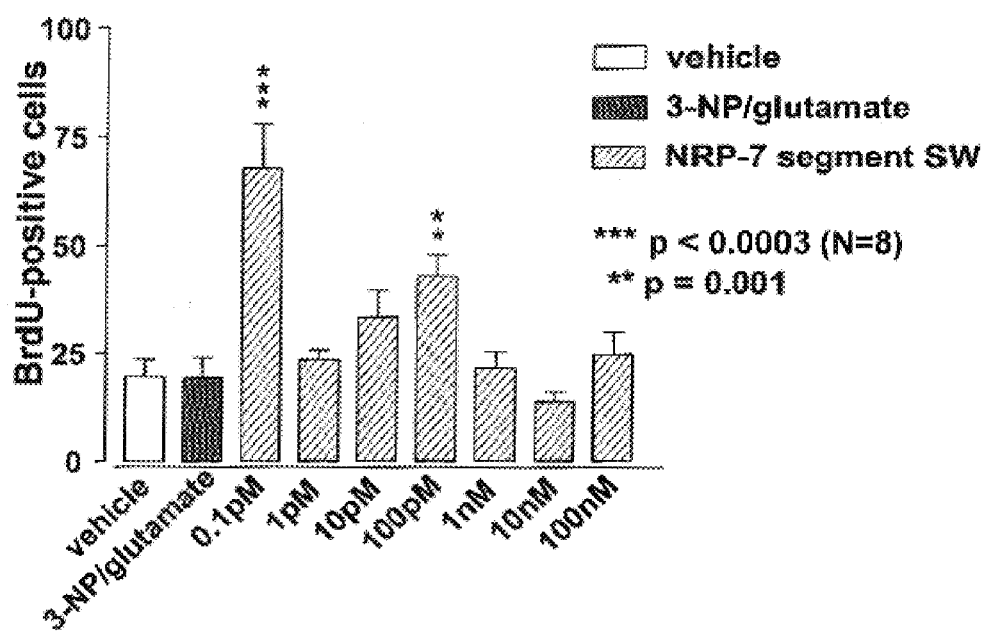

FIG. 24 depicts results of studies of proliferation induction under injury conditions using the mouse peptide, NRP-7 segment SW (SEQ ID NO:24). Cerebellar microexplants were injured by 3-NP/glutamate. NRP and BrdU were administered simultaneously for 24 hrs. After 72 hrs, BrdU-positive nuclei were counted within four microscopic fields for each culture. There was substantial proliferation induction by 0.1 pM and 100 pM of NRP-7 segment SW (SEQ ID NO: 24). No proliferation differences between injured and non-injured cerebellar cells were observed. This indirectly indicates very low numbers of injury-induced proliferative astrocytes within the cerebellar microexplant system.

Figure 25:
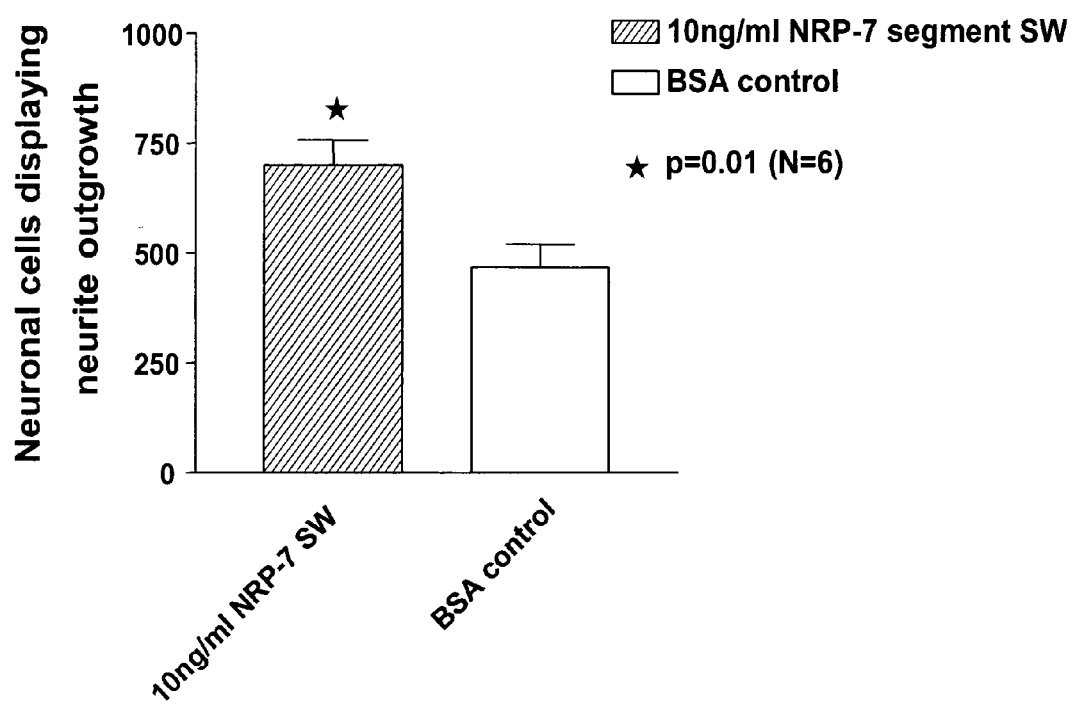

FIG. 25 depicts results of studies of the haptotactic migration assay using culture plates coated with NRP-7 segment SW (SEQ ID NO: 24). NRP-7 (0.1 µg/ml and 1 µg/ml) was diluted in 10 µg/ml BSA. The plates were then coated using 50 µg/ml poly-D-lysine (PDL) coating. Cortical cells were seeded into PDL-coated inserts and 1 pg/ml 24 mer peptide was added in solution. Cell counting was done after 1 day in vitro. NRP-7 segment SW significantly increased the number of cells with neurite outgrowth.

Figure 26:
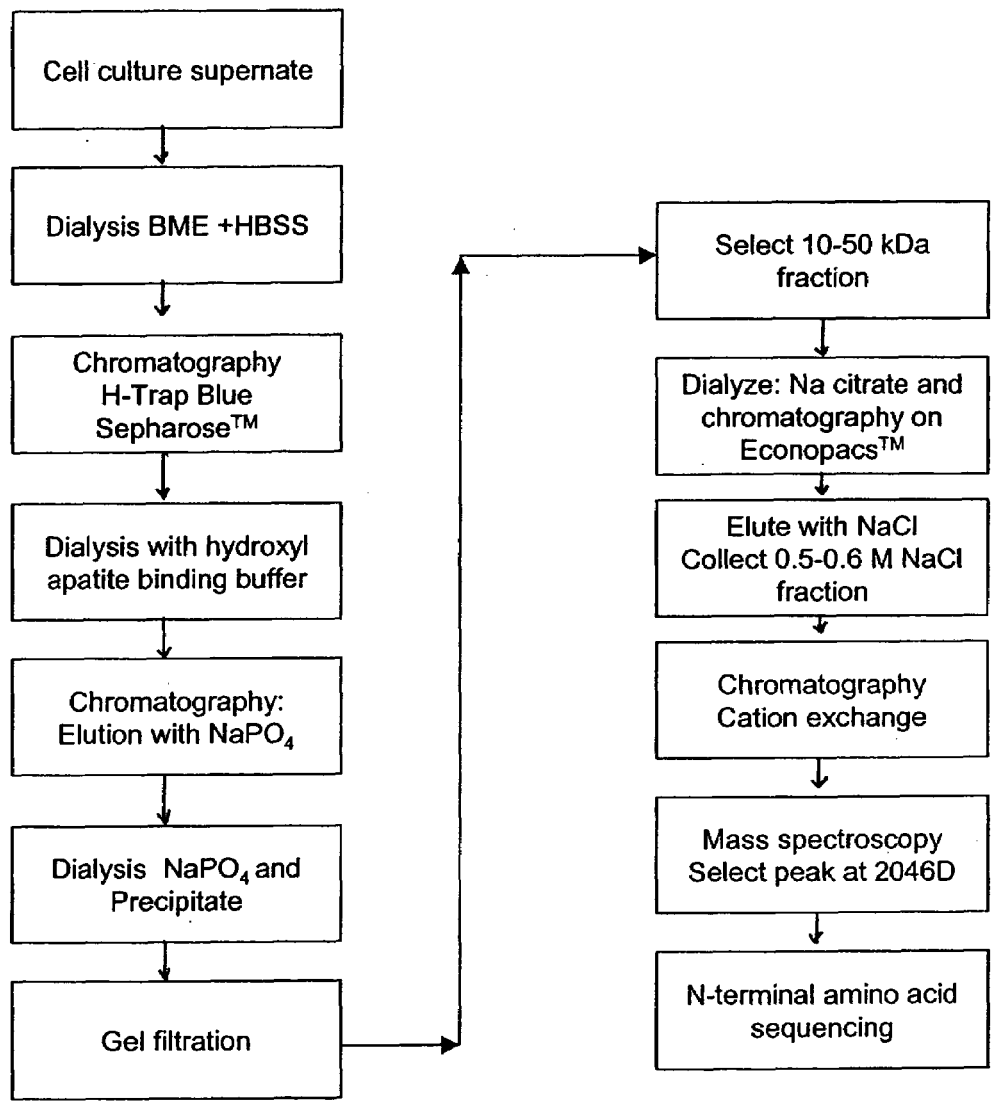

FIG. 26 depicts a flow chart of steps used to purify NRP-1 (SEQ ID NO: 2).

Figure 27:
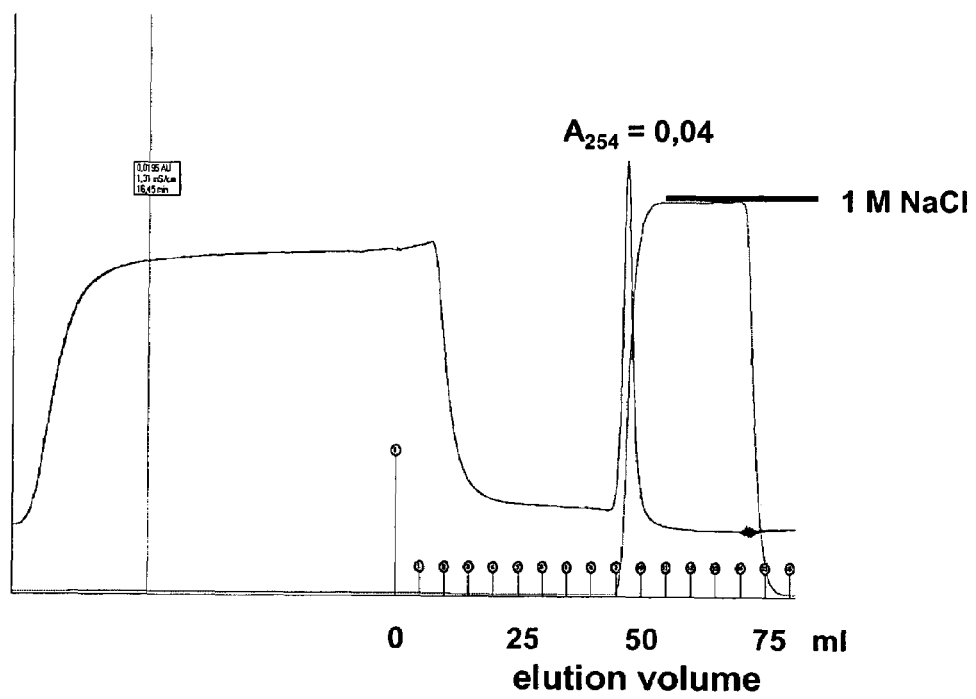

FIG. 27 depicts results of a cation exchange purification step to obtain homogenously purified NRP-1 (SEQ ID NO: 2). Purification was carried out on High S (BioRad) cation exchanger using a low-pressure chromatography unit from BioRad. An 80% acetone-precipitated bioactive peak from gel filtration chromatography was extensively desalted against 10 mM citrate (pH 4), was chromatographed (1 ml/min) in 0.01 M citrate (pH 4). The column was eluted using 1M NaCl in 0.01 M citrate (pH 4.5). Migration-promoting activity eluted between 43-53 ml elution volume. Absorbance was measured at a wavelength of 254 nm. Purity of the resulting NRP was verified by N-terminal amino acid sequencing, which produced unambiguous results.

Figure 28:
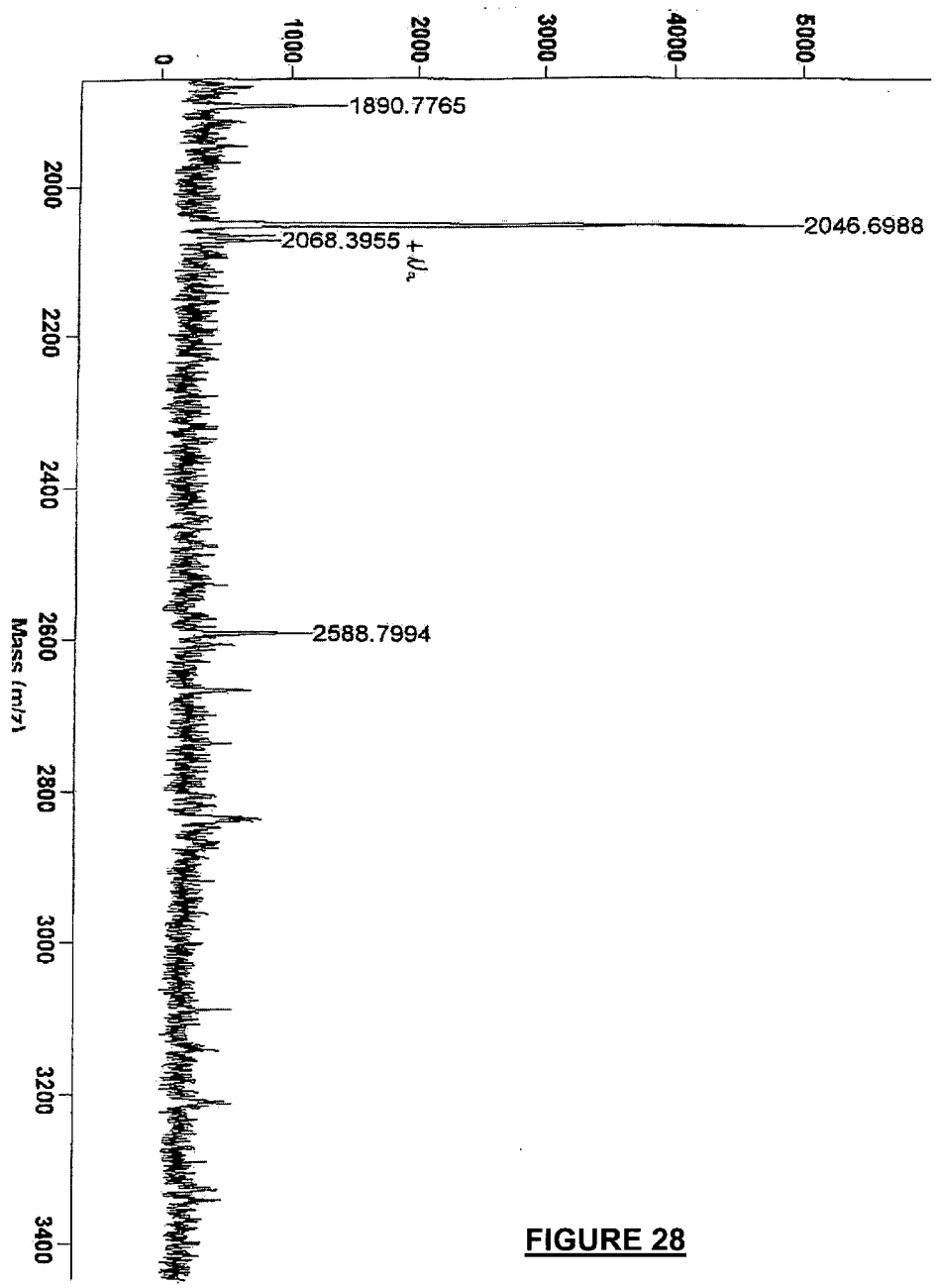

FIG. 28 depicts results of an analysis of NRP-1 (SEQ ID NO:2) by MALDI-TOF mass spectrometry. Purity and mass $(M+H^+)$ of the major peptide from the cation exchange purification was confirmed by MALDI-TOF MS. The single charged peptide NRP-1 (SEQ ID NO: 2) that represents the major peak has a molecular mass of 2046.

Figures 29A, 29B:
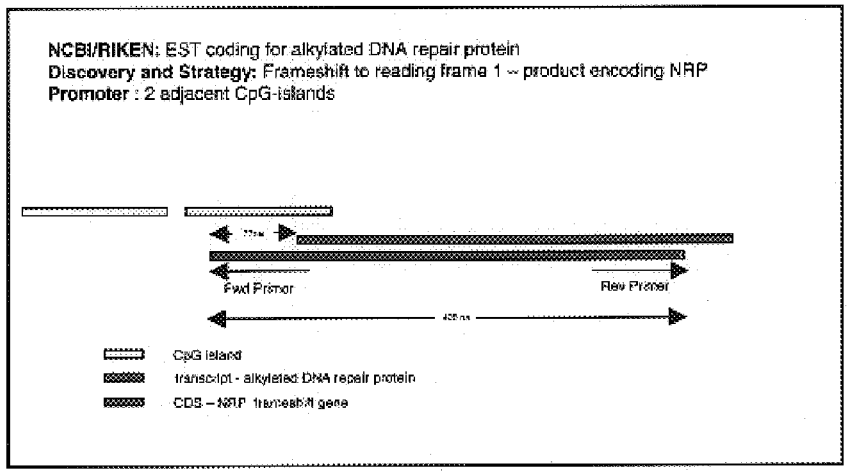

FIG. 29A depicts the structure of the gene encoding NRP-7 with an intron (SEQ ID NO:35), highlighting the promoter region containing two CpG islands (one predicted for NRP, the downstream one predicted for DNA-repair protein), as well as the existence of the NRP gene as a 2 bp frameshift of a known gene encoding a DNA repair protein. The primer positions for obtaining the NRP-7 (SEQ ID NO:35) gene product are indicated.

FIG. 29B shows 72.2% homology between the mouse (NRP-7 long) and the rat NRP (NRP-9) orthologues, the red number indicates the homology compared within the biological active NRP domains while the blue lines depict putative N-glycosylation sites.

FIG. 29C shows the alignment of human cachexia-related protein with mouse NRP (NRP-7 long). Note the conservation of leucine, glycine and proline amino acid residues throughout both sequences. The overall homology is 34.4%. While the biological active domain of the cachexia-related protein is located directly after the signal peptide at position 20, the active domain of mouse NRP (NRP-7 long) is starting at amino acid position 83.

FIG. 29D shows 52.5% overall homology between mouse NRP fragment and the human trefoil protein Ps2. Nine of fifteen amino acid residues that define the trefoil factor family (TFF) consensus sequence are present in NRPs, thereby confirming the occurrence of a trefoil factor domain in NRP.

FIG. 29E shows the alignment between mouse SDF-1α and mouse NRP (NRP-7 long) protein sequences. There is a moderate homology of 32.6% amongst both neuronal chemoattractive molecules.

Figure 30:
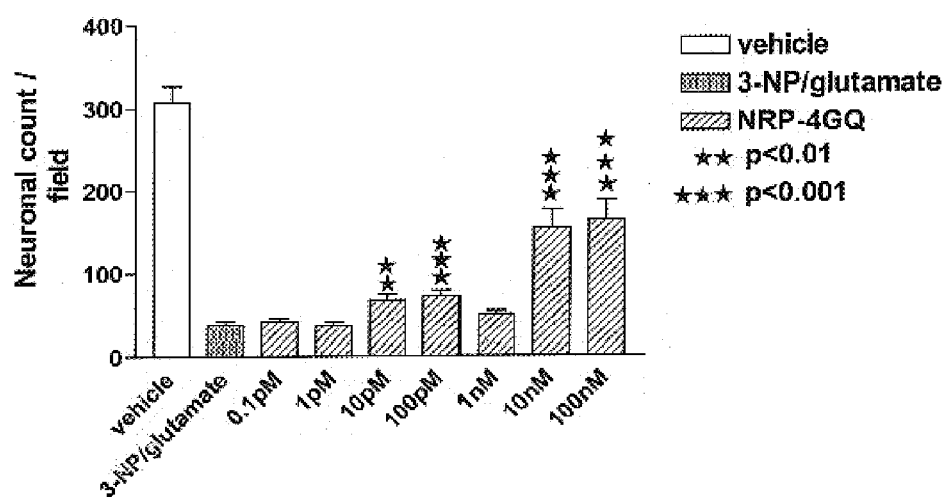

FIG. 30 depicts survival induction by NRP-4 segment GQ (SEQ ID NO: 26) after excitotoxic/oxidative injury using 3-NP/glutamate.

Figure 31:
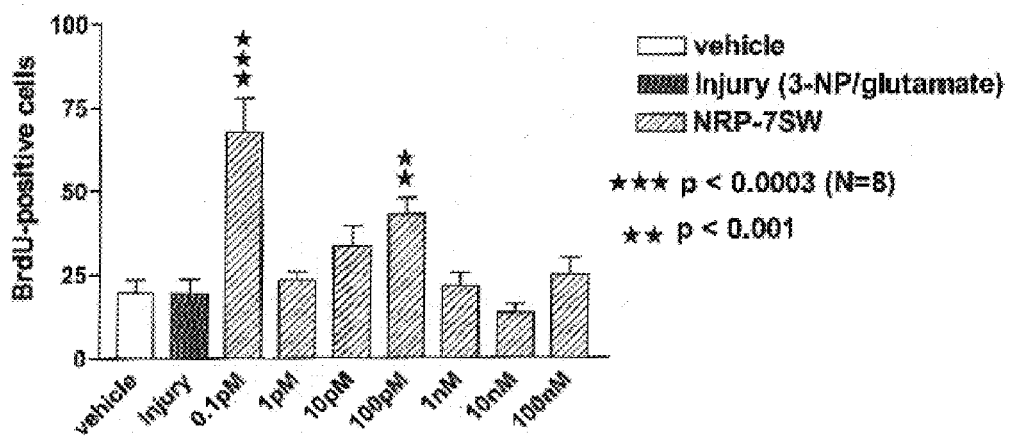

FIG. 31 depicts proliferation induction with NRP-7 segment SW (SEQ ID NO: 24) in neurons injured using 3-NP/glutamate.

Figure 32A:
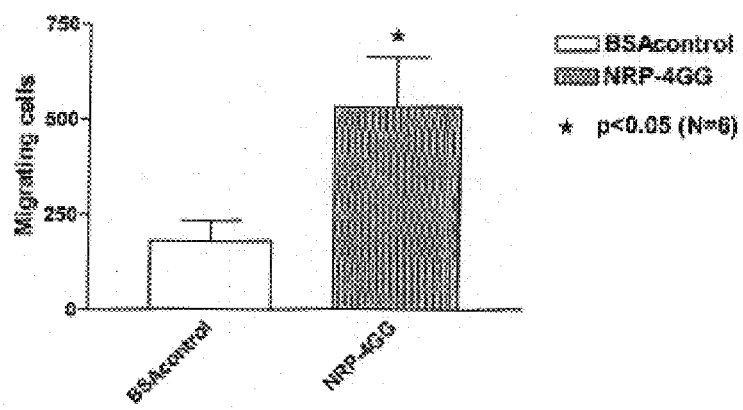
Figure 32B:
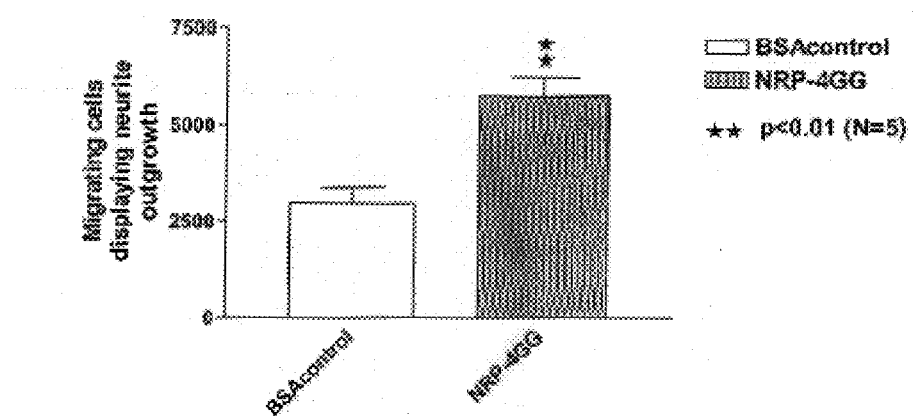
Figure 32C:
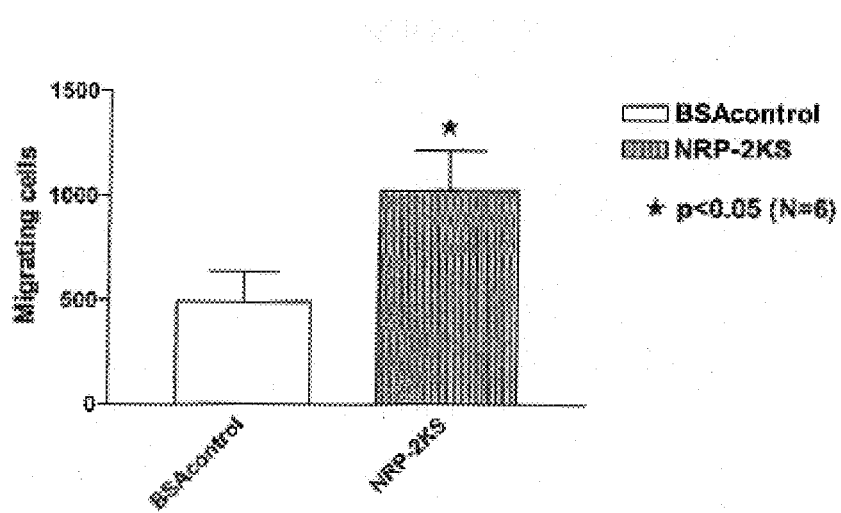
Figure 32D:
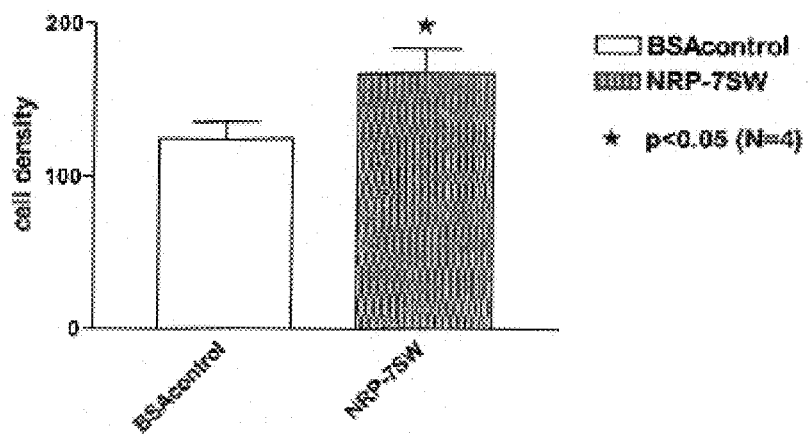
Figure 32E:
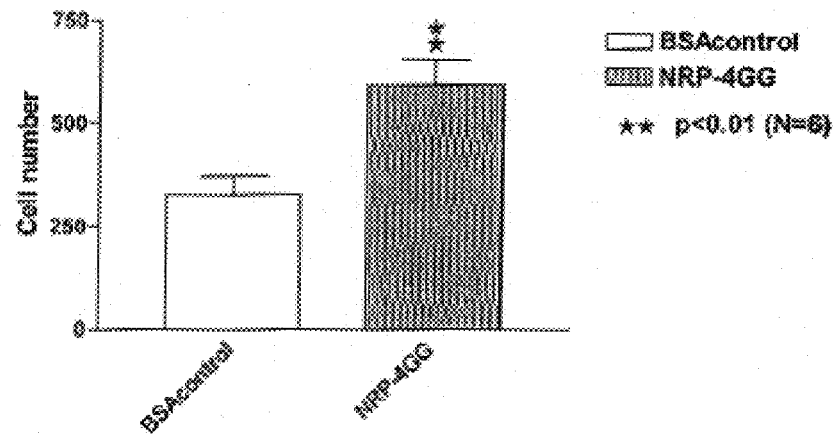
Figure 32F:
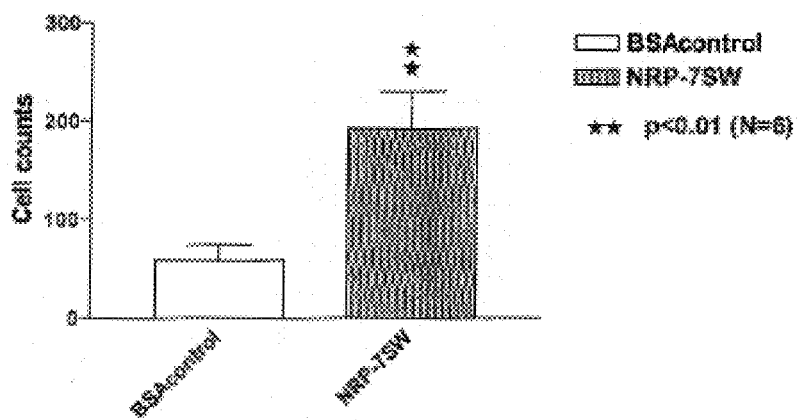

FIG. 32A depicts a haptotactic migration assay with mouse MEB-5 cells using 10 ng/ml of NRP-4 GG (SEQ ID NO:29) peptide for coating, with 200,000 MEB-5 cells. FIG. 32B depicts results of a migration assay with primary mouse stem cells (E14) using 10 ng/ml of NRP-4 GG (SEQ ID NO:29) peptide for coating, with 200,000 cells seeded. FIG. 32C depicts results of a migration assay with mouse MEB-5 cells using 1 ng/ml of NRP-2 KS (SEQ ID NO:23) peptide coating, with 200,000 cells seeded. FIG. 32D depicts a migration assay with primary mouse stem cells using 10 ng/ml of NRP-7 SW (SEQ ID NO:24) coating, with 400,000 cells seeded. FIG. 32E depicts migration assay with wild-type PC-12 cells using 50 ng/ml of NRP-4 GG (SEQ ID NO: 29) coating, 200,000 cells per well. FIG. 32F depicts a migration assay with wild type PC-12 cells and 1 ng/ml NRP-7 SW (SEQ ID NO:24) coating followed by matrigel/PDL coating, with 100,000 cells seeded. In each case, the NRP promoted neuronal migration.

Figure 33A:
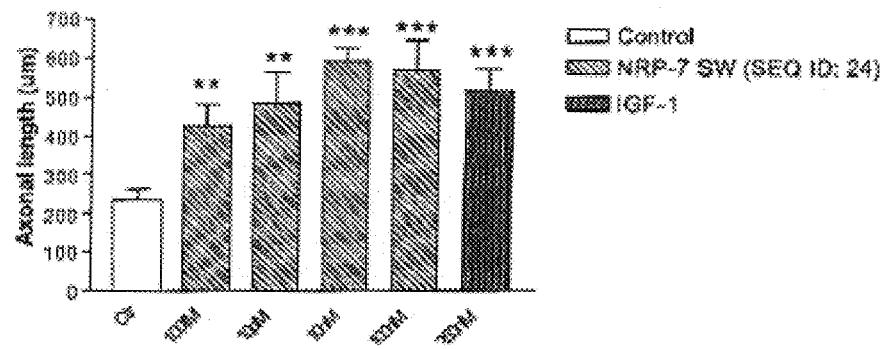
Figure 33B:
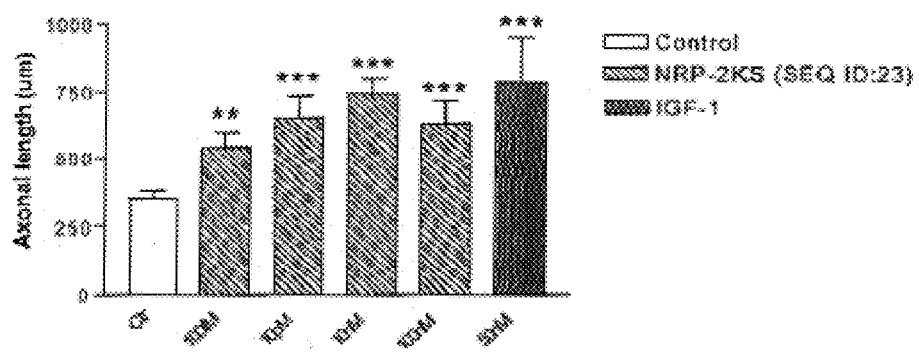
Figure 33C:
Figure 33D:
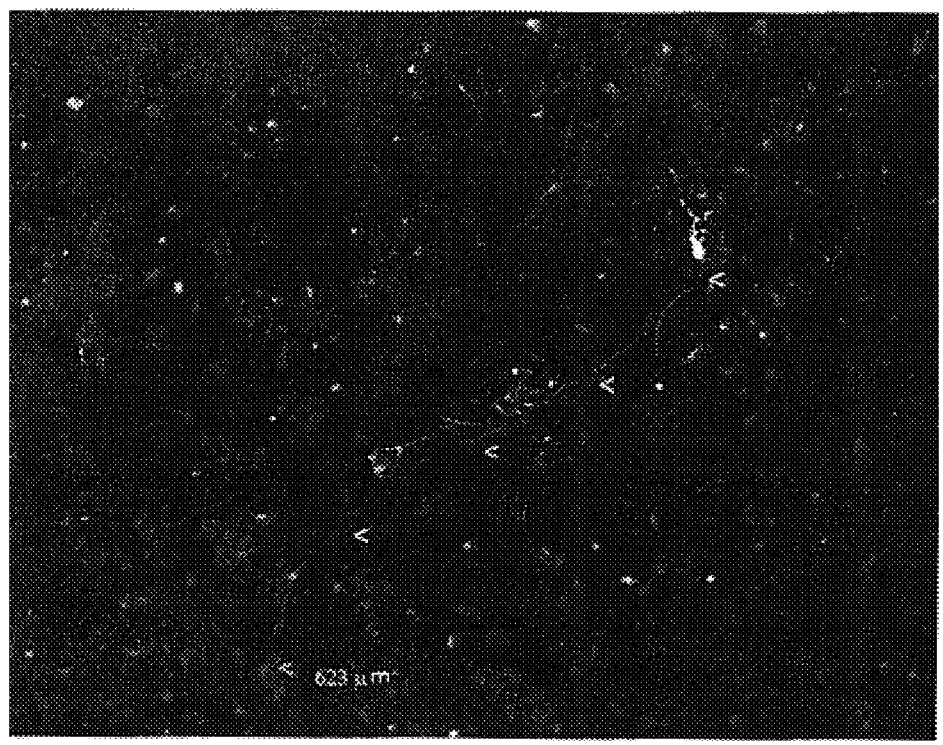
Figure 33E:
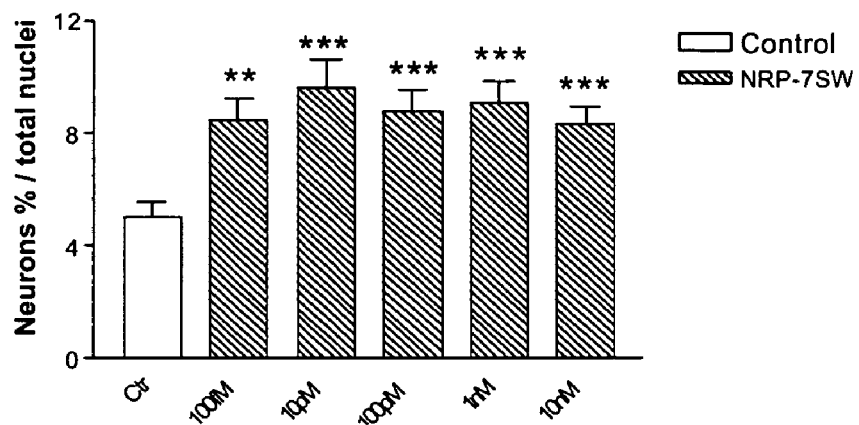
Figure 33F:
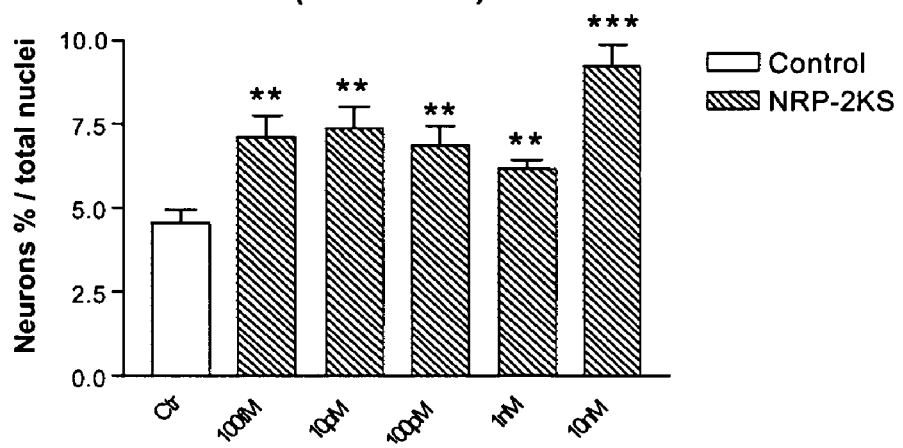
Figure 33G:
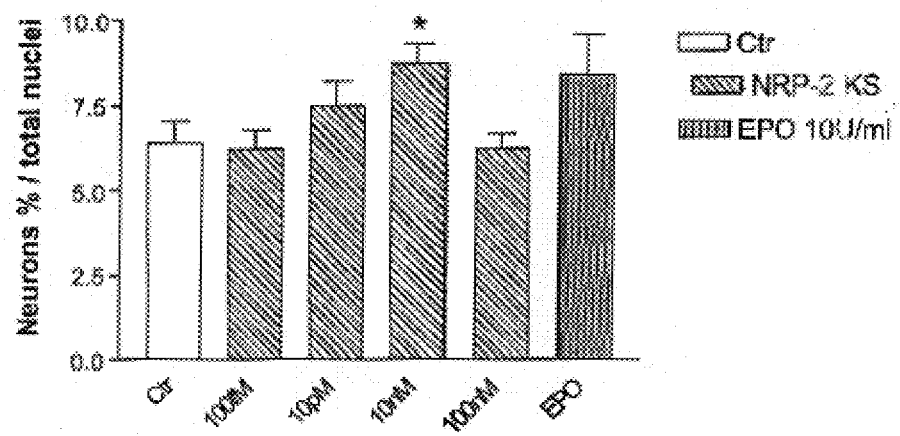
Figure 33H:
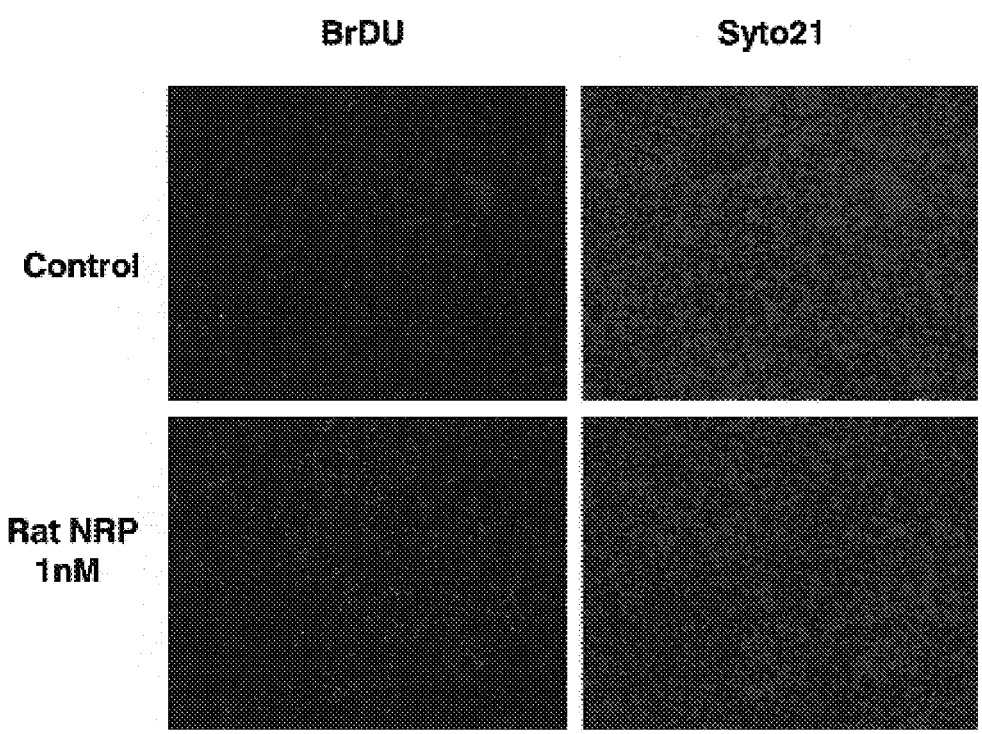

FIGS. 33A and 33B depict graphs showing the medium length of the five longest axons per culture well of neural stem cells differentiated for 7 days in the presence of the NRPs. FIG. 33A depicts effects of NRP-7 SW (SEQ ID NO:24) and IGF-1. FIG. 33B depicts effects of NRP-2KS (SEQ ID NO:23), IGF-1 or differentiation medium alone. Significant differences from control medium were observed as determined by two-tailed Students t-test.  p<0.01; * p<0.001. FIGS. 33C and 33D depict representative examples of longest axonal outgrowth in differentiation medium alone. FIG. 33D depicts the longest axonal outgrowth in the presence of 10 nM NRP-7 SW (SEQ ID NO:24), whereas FIG. 33D depicts the control condition. FIGS. 33E and 33F depict graphs showing the effects of NRP-7 SW (SEQ ID NO:24) and NRP-2KS (SEQ ID NO:23) on the increase in the of NSC cells that had undergone neuronal differentiation. FIG. 33G indicates that nanomolar concentrations of NRP-2KS (SEQ ID NO:23) promoted the production of neuronal progenitors at the expense of multipotent stem cells from mouse forebrain neural stem cells. FIG. 33H shows NRP-9 segment SD (SEQ ID NO:34) administration to undifferentiated NSCs before the onset of the differentiation experimental scheme. The upregulation of BrdU-positive cells under NRP treatment occurs while there is no obvious change in the overall cell number.

Figure 34A:
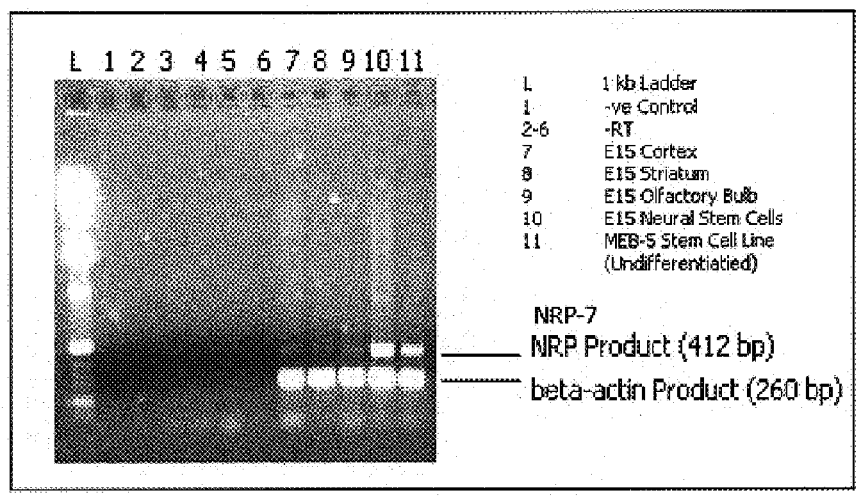

FIGS. 34A-K depicts gene expression of NRP within NSCs and in embryonic mouse tissues. (FIGS. 34A-C) Expression levels of mouse NRP (upper band, 412 bp) were semi-quantitatively compared to β-actin expression (lower band, 260 bp) in multiplex PCR. (FIG. 34A) mouse NRP expression was detected in embryonic brain tissue from E15 mice in the cortex (Ctx), striatum (Str) and the olfactory bulb (OB). Albeit, the level was much lower compared to acutely isolated and immortalized mouse neural stem cells. (FIG. 34B) Differentiation of neural stem cells towards astrocytes with CNTF, markedly increases NRP MRNA expression, compared to undifferentiated stem cells, or neuronal differentiation with BDNF, (FIG. 34C) Analysis of a variety of E19 embryonic mouse tissues shows that, except for the lung, expression of mouse NRP is lower, or absent in non nervous system tissues, compared with embryonic cortex, astrocytic differentiated NSC and astrocyte cultures from the perinatal forebrain. (FIG. 34D) Northern blot hybridization with a 88 bp probe, non-overlapping with the DNA repair protein sequence, detects two alternative mRNA approximately sized 0.8 and 1.2 kb in RNA from perinatal astrocyte cultures. In situ hybridization with the mouse NRP antisense probe strongly labels NSC (FIG. 34E), while there is no specific signal in the sense control (FIG. 34F). NRP mRNA expression in NSC (FIG. 34G) is confirmed by double-labelling with nestin (FIG. 34H). In situ hybridization of coronal E15 mouse forebrain slice display, besides the ventricular zone, a strong signal in the cortical anlage, especially in the subplate and marginal zones and less intense in the cortical plate (FIG. 34I). Nestin positive cells spanning the length from the subplate to the marginal zone (FIG. 34J) co-express the mouse NRP message (FIG. 34K).

FIG. 34 L depicts expression of the NRP-2 (SEQ ID NO:4) gene product in NT-2 cells in the absence of injury and 6 hrs post-injury caused by the mitochondrial toxin 3-nitropropionic acid. Gene expression was substantially decreased when the cells were treated with 3-NP for more than 1 hr.

Figure 35A:
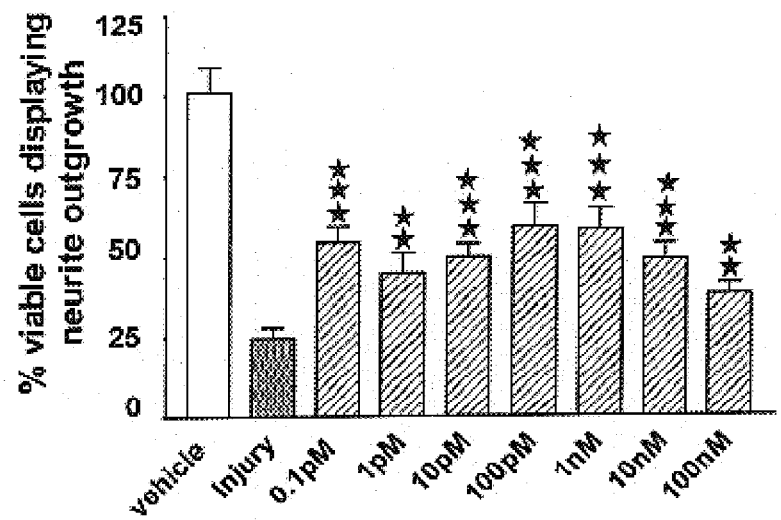
Figure 35B:
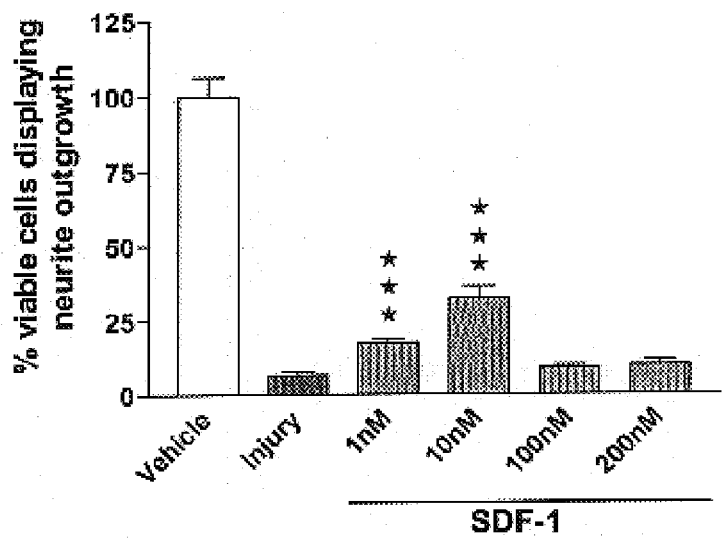

FIG. 35 depicts neuronal survival and proliferation induction by NRP-7 Segment SW. FIG. 35A shows the effects of NRP-7SW (SEQ ID NO: 24) on neuroprotective activity over a broad dosage range of from 0.1 μM to 100 nM, while FIG. 35B shows that SDF-1 had only a limited neuroprotective effect compared to NRP.

Figure 36A:
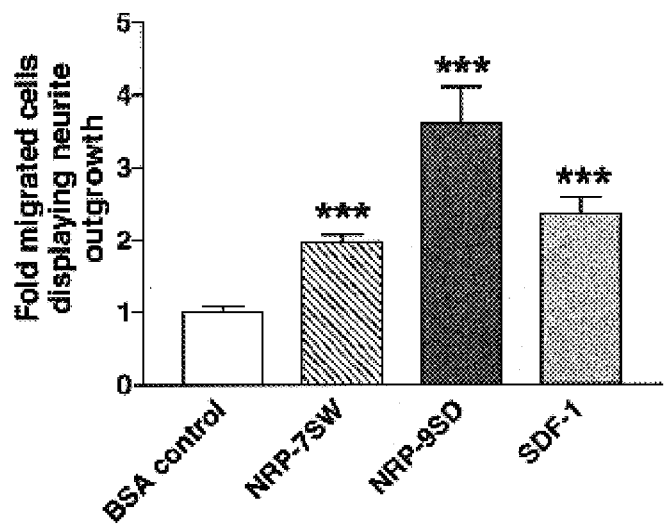
Figure 36B:
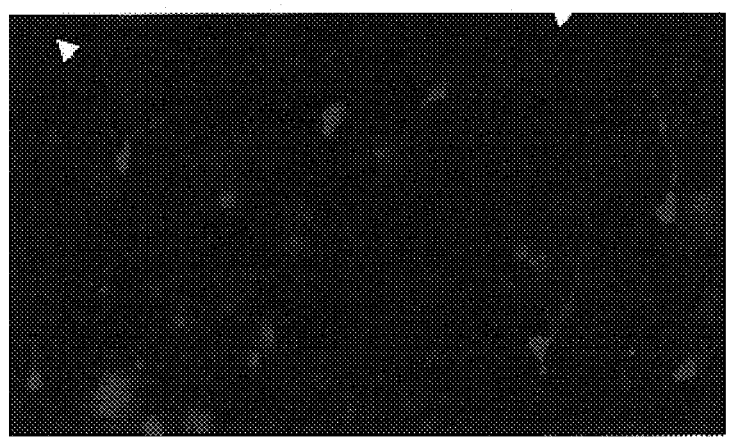
Figure 36C:
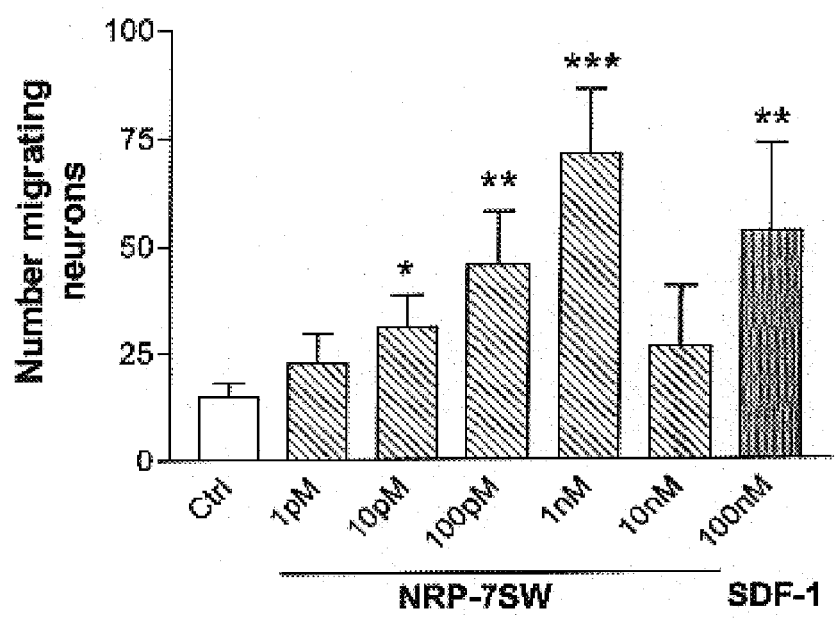

FIG. 36 depicts a graph of results of studies of neuronal migration induction by NRPs. FIG. 36A shows that rat and mouse synthetic peptide-derived NRPs (NRP-9SD and NRP-7SW) exhibited chemoattractive properties in attracting neuronal stem cells ("NSCs") as shown with a haptotactic migration assay. The efficacy of NRP-7SW was similar to that of SDF-1, but the NRPs displayed higher potency. Although the magnitudes of effects of SDF-1 and NRP-7SW appear similar, the amount of SDF-1 (100 nM) was higher than that of NRP-7SW (0.2 nM). Thus, NRP-7SW is about 500 times more potent than SDF-1. FIG. 36B depicts a microphotograph of brain OTCs showing travelling medial ganglionic eminence-derived neural precursor cells migrating towards the cortical anlage. FIG. 36C: Quantification of the OTC assay demonstrated an optimum dose of NRP-7SW at a concentration of 1 nM while SDF-1 was less potent. Student's t-test was used for statistical analysis (i p<0.05, ii p<0.01, iii p<0.001- N=6).

FIG. 37 depicts expression and functional properties of full-length mouse recombinant NRP-7 long (SEQ ID NO:35). FIG. 37A shows a northern blot demonstrating that under the control of a cytomegalovirus ("CMV") promoter, mouse NRP-7 long (SEQ ID NO:35) gene 0.8kb signal was highly overexpressed in HEK cells, as detected by the NRP gene-specific 88bp-cRNA probe. FIG. 37B is a Western blot showing that NRP-7 long (SEQ ID NO:36) is expressed by HEK-cells and migrates at a molecular weight of 20 kDa. FIG. 37C shows that recombinant Myc-NRP-7 long (SEQ ID NO:35)-HEK cells provide 51% neuroprotection to oxidative/excitotoxic-injured cerebellar microexplants. FIG. 37D shows that Myc-NRP-7 long (SEQ ID NO:36)-HEK cells possess chemoattractive activity for attracting NSCs in a haptotactic migration assay when seeded on the bottom of the dish. More than twice the number of cells was attracted from the insert to the bottom of the culture dish compared to Myc-HEK control experiments. Student's t-test was applied for statistical analysis (* * * p<0.001; N=4 for microexplants and * * * p<0.001; N=6 for haptotactic migration assay).

Figure 38A:
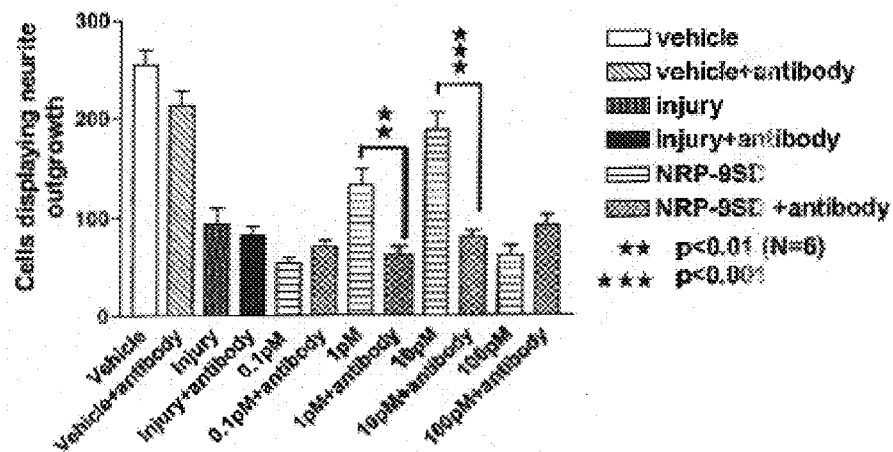
Figure 38B:
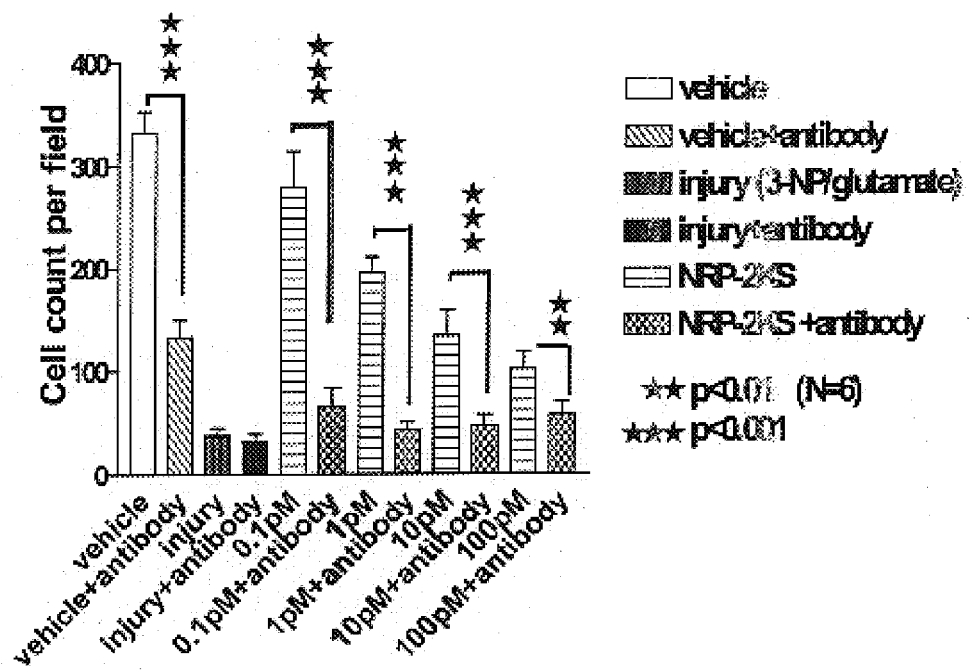
Figure 38C:
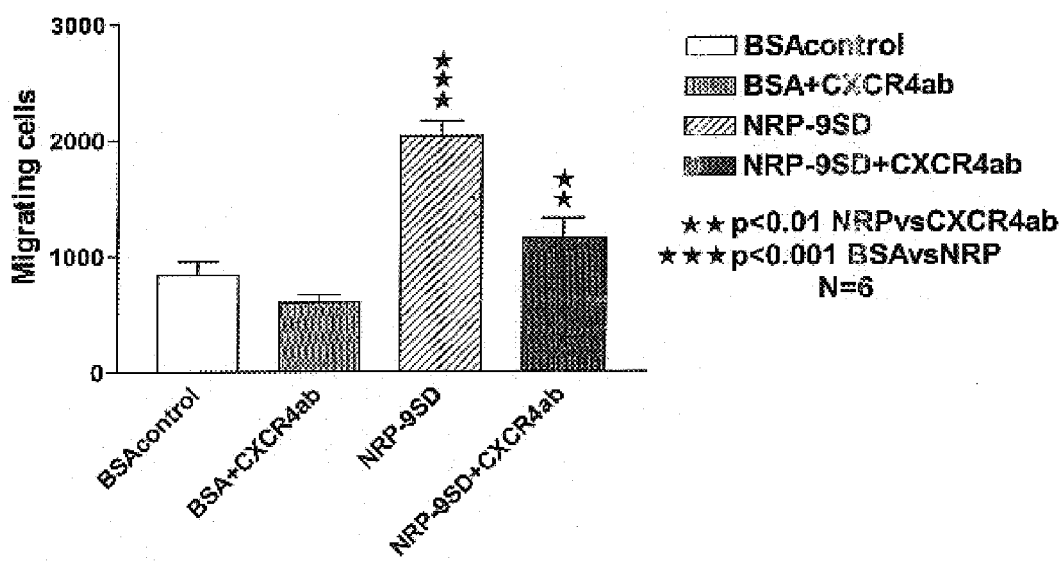

FIG. 38 depicts results of studies using CSCR4 antibody and NRP-9SD on P4-cerebellar explants. FIGS. 38A, B and C show that neuronal survival-promoting and migration-inducing action of NRP-9 SW was inhibited by CXCR4 neutralizing antibody, suggesting that NRPs can compete with the CSCR4 receptor ligand for binding to the CXCR4 receptor. FIG. 38A shows NRP-9 SD (SEQ ID NO:34) inhibition of neurite outgrowth. FIG. 38B depicts NRP-7SW (SEQ ID NO:24) inhibition of neurite outgrowth. Chemoattractive effects of 10 ng/ml NRP coated on the culture dish were completely blocked by pre-incubating the neuronal stem cell line MEB-5 for 1.5 hrs with a neutralizing antibody for CXCR4. Significantly less cells migrated compared to NRP-9 SD (SEQ ID NO:34) peptide alone (FIG. 38C).

Figure 39A:
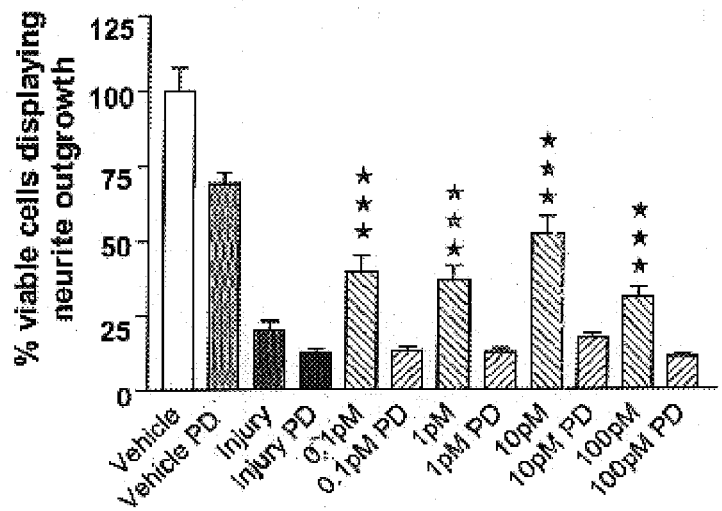
Figure 39B:
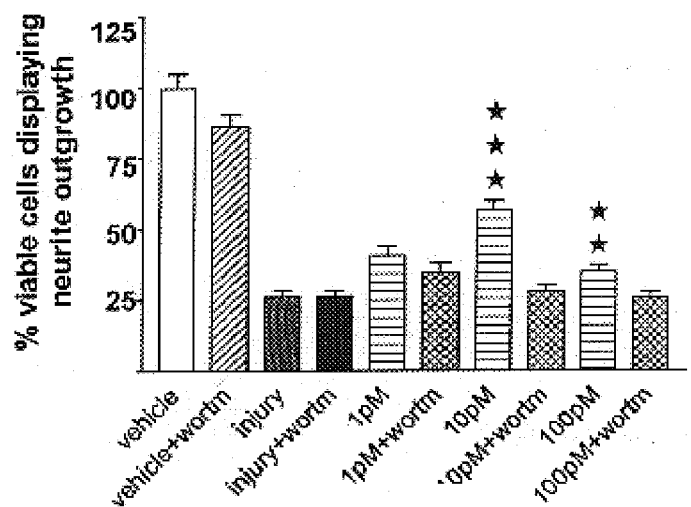
Figure 39C:
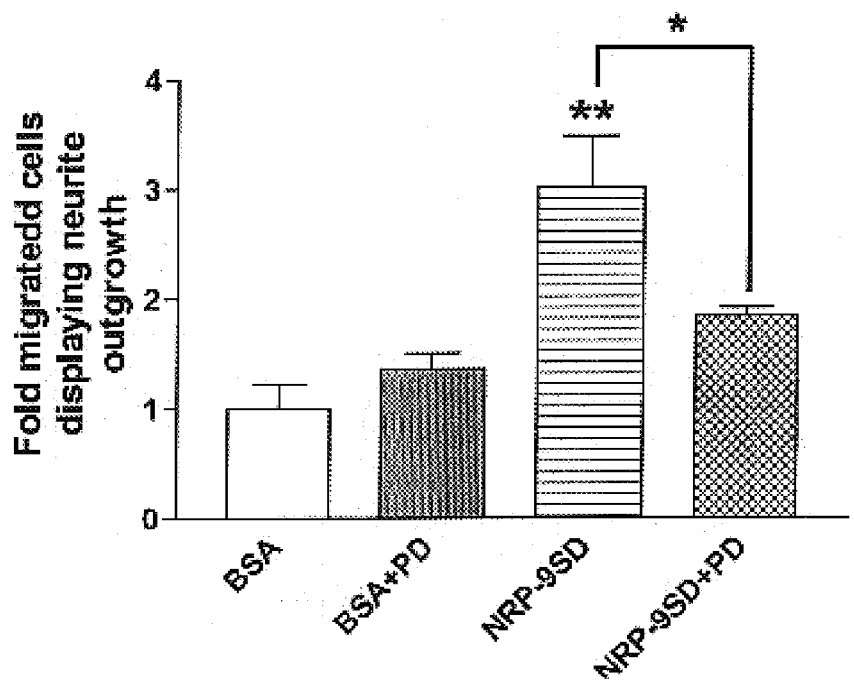

FIG. 39 depicts a possible signalling cascade involved in NRP neuroprotective and migration-inducing activity. FIG. 39A shows that the MAPK (MEK)-inhibitor PD98509 completely blocked neuroprotective activity of rat NRP-9 SD (SEQ ID NO: 34) over a range of different NRP concentrations. FIG. 39B shows that like PD98509, the PIK-3 inhibitor wortmannin inhibited the neuroprotective activity of NRP-9 SD (SEQ ID NO: 34). FIG. 39C shows that the NRP-9 SD (4 nM) induced increase in migrating NSC numbers was inhibited by 15 μM PD98509, whereas the basal migration level in BSA coated wells was not significantly altered by the MEK-inhibitor (* p<0.05, * * p<0.01, * * * p<0.001- N=8).

Figure 40B:
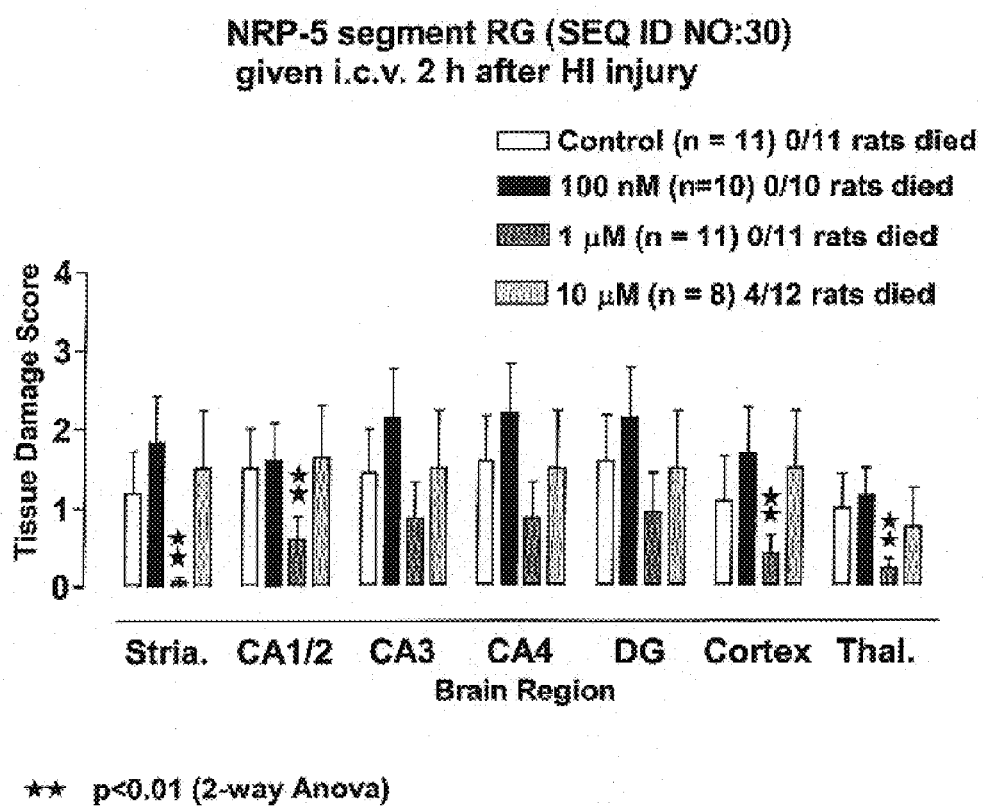

FIG. 40A depicts results of studies in which NRP-4 segment PQ (SEQ ID NO:43), provided substantial neuroprotection in all analysed brain regions five days after insult when administered ICV 2 hrs after hypoxia. FIG. 40B depicts results of studies in which NRP-5 segment RG (SEQ ID NO: 30) administered ICV 2 hrs after hypoxia provided substantial neuroprotection in all analysed brain regions five days after the hypoxic insult.

Figure 41:
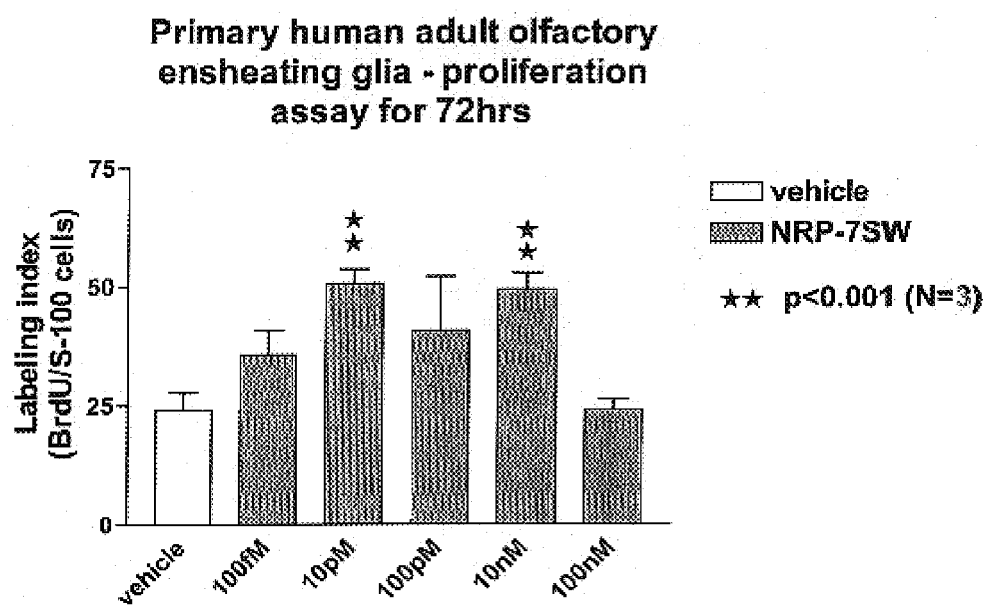

FIG. 41 depicts results of studies in which NRP-7 segment SW (SEQ ID NO:24) enhance proliferation of primary human adult olfactory ensheating glia.

FIG. 42A-D depicts the neuroprotective activity of 4 NRP-5 RG analogues in reference to the original NRP-5 RG sequence.

Figure 43:
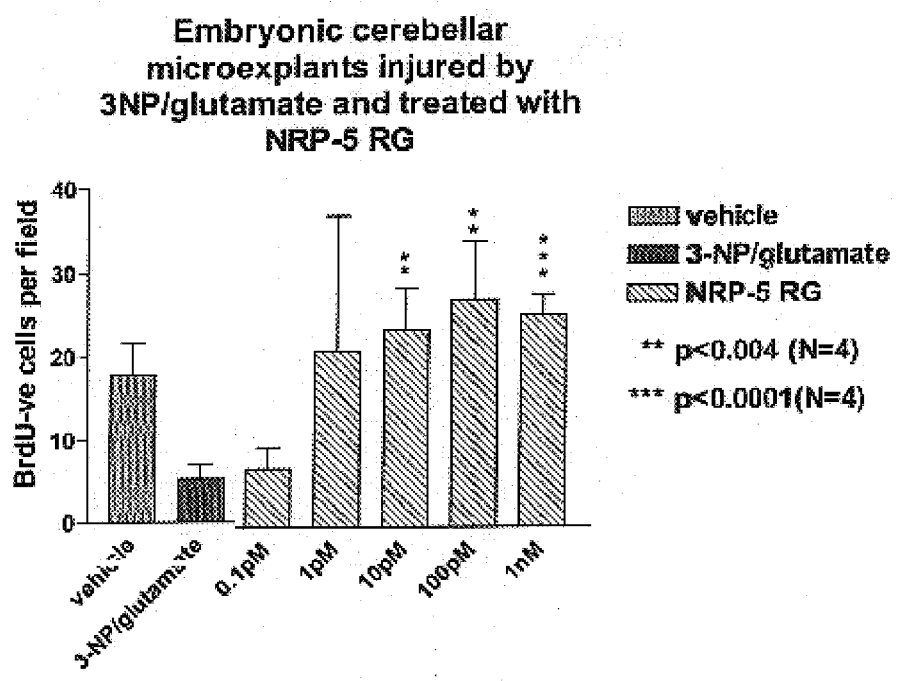

FIG. 43 depicts the proliferation-inducing capacity of NRP-5 RG within embryonic cerebellar cells.

FIG. 44 depicts a haptotactic migration assay using mouse NSCs and NRP-5 RG as chemoattractant.

Figure 45:
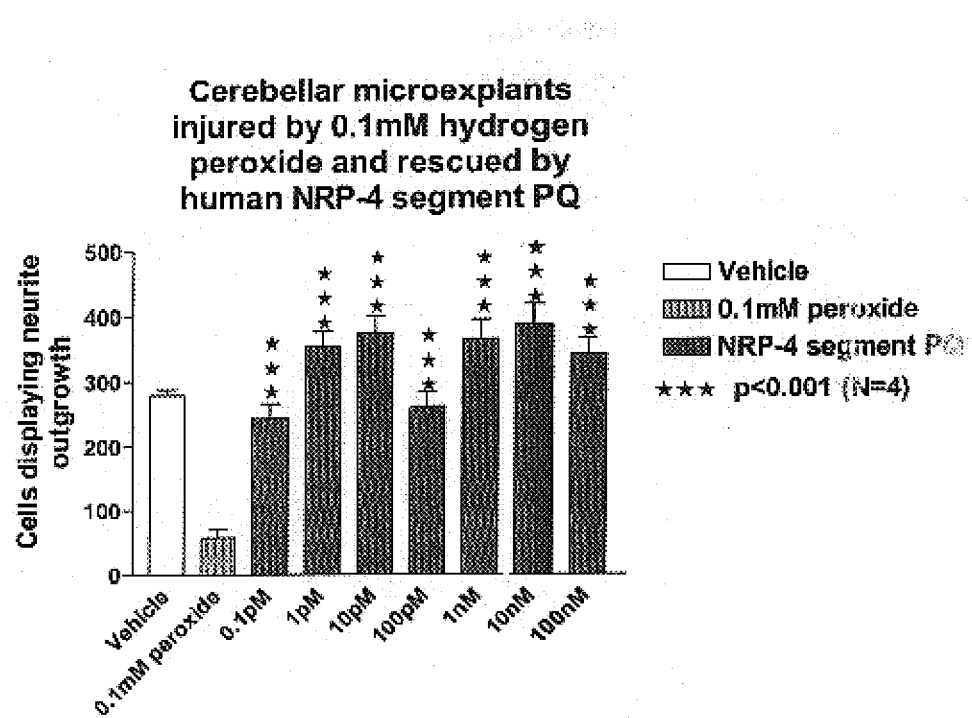

FIG. 45 depicts the neuroprotective effects NRP-4 PQ after 48 hrs of oxidative stress (0. IlmM hydrogen peroxide).

Figure 46:
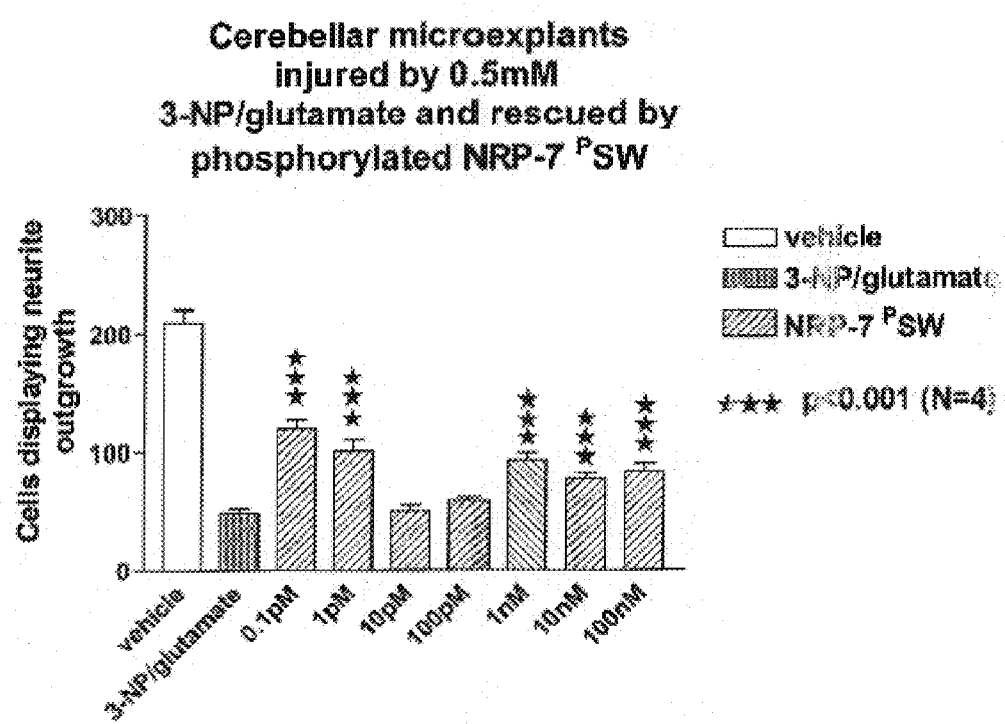

FIG. 46 depicts the neuroprotective profile of phosphorylated NRP-7 SW (NRP-7 $^P$SW).

Figure 47:
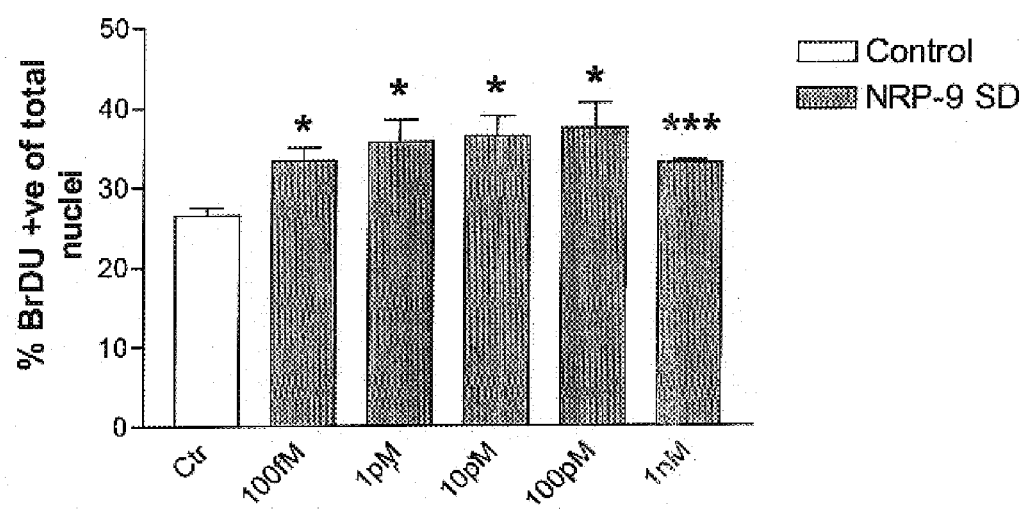

FIG. 47 depicts a graph of studies showing effects of NRP 9 SD on BrDU stained nuclei.

Figure 48A:
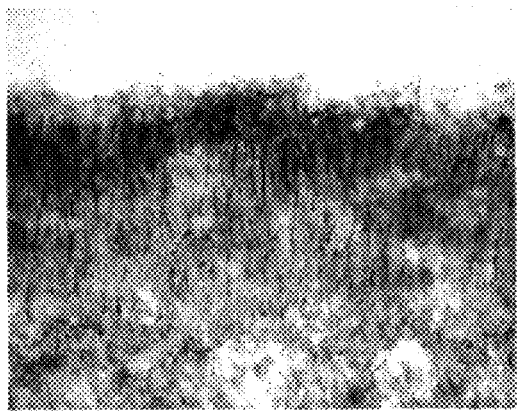
Figure 48B:
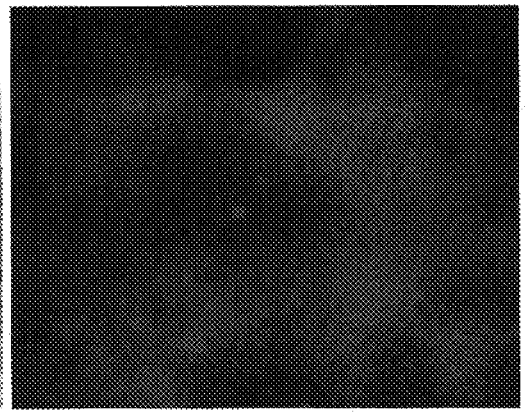

FIGS. 48 A and B depict graphs of gene expression of NRP-7 (SEQ ID NO:35) within the neuroepithelial stem cell—radial glia-astrocytic lineage. FIG. 48A depicts expression of the mouse frameshift transcript in the cerebral cortex of E17 mouse brain, detected with the 88 mer specific probe by in situ hybridization on cryosections and FIG. 48B depicts immunohistochemistry of the same section with an anti-vimentin antibody, demonstrating a high degree of co-localization of the mouse frameshift message with the vimentin intermediate filament protein.

DETAILED DESCRIPTION

Definitions

The term "homolog" includes one or more genes whose gene sequences are significantly related because of an evolutionary relationship, either between species (ortholog) or within a species (paralog). Homolog also includes genes related by descent from a common ancestral DNA sequence. Homolog also includes a relationship between genes separated by a speciation event, or to a relationship between genes by the event of genetic duplication (see paralog). As used herein, the term "homolog" also includes gene products related to each other by way of an evolutionary relationship. NRPs having conserved amino acid sequence domains are examples of homologs.

The term "paralog" includes one of a set of homologous genes that have diverged from each other as a consequence of genetic duplication. For example, the mouse alpha globin and beta globin genes are paralogs. As used herein, the term "paralog" also includes gene products related to each other by way of an evolutionary relationship. Human NRPs having conserved amino acid sequence domains are examples of paralogs.

The term "ortholog" includes one of a set of homologous genes that have diverged from each other as a consequence of speciation. For example, the alpha globin genes of mouse and chick are orthologs. As used herein, the term "ortholog" also includes gene products related to each other by way of an evolutionary relationship. Human and mouse NRPs having conserved amino acid sequence domains are examples of homologs.

The term "paralog peptide" includes a peptide encoded by a paralog nucleotide sequence.

The term "peptide" and "protein" include polymers made of amino acids.

The term "prodrug" includes molecules, including pro-peptides which, following enzymatic, metabolic or other processing, result in an active NRP, an active NRP analog or a NRP paralog.

The term "NRP compound" includes NRPs, NRP homologs, NRP paralogs, NRP orthologs, NRP analogs, and prodrugs of NRP.

The term "NRP" includes peptides having functions including one or more of neural migration, neuroblast migration, neural proliferation, neuronal differentiation, neuronal survival and neurite outgrowth, regardless of evolutionary relationship.

Amino acids are represented by the standard symbols where alanine is represented by "A" or "Ala", arginine by "R" or "Arg", asparagine by "N" or "Asn", aspartic acid by "D" or "Asp", cysteine by "C" or "Cys", glutamic acid by "E" or "Glu", glutamine by "Q" or "Gln", glycine by "G" or "Gly", histidine by "H" or "His", isoleucine by "I" or "Ile", leucine by "L" or "Leu", lysine by "K" or "Lys", methionine by "M" or "Met", phenylalanine by "F" or "Phe", proline by "P" or "Pro", serine by "S" or "Ser", threonine by "T" or "Thr", tryptophan by "W" or "Trp", tyrosine by "Y" or "Tyr", and valine by "V" or "Val". Carboxy terminally amidated peptides are indicated by —NH$_2$.

Nucleic acids comprise nucleotides including adenine, which is represented by "a"; thymine, which is represented by "t"; cytosine, which is represented by "c" and guanine, which is represented by "g." A nucleotide, which can be either guanine or adenine, is represented by "r", a nucleotide that can be either thymine or cytosine is represented by "y" and a nucleotide, which can be guanine, adenine, cytosine, or thymine is represented by "n". Polynucleotides may be DNA or RNA, and may be either single stranded or double stranded. Where the polynucleotide is a RNA polynucleotide, uracil "u" may be substituted for thymine.

"Disease" includes any unhealthy condition of CNS or peripheral nervous system of an animal, including particularly Parkinson's disease, Lewy Body, Huntington's disease, Alzheimer's disease, multiple sclerosis, motor neuron disease, muscular dystrophy, peripheral neuropathies, metabolic disorders of the nervous system including glycogen storage diseases.

"Injury" includes any acute damage of an animal, including particularly stroke, traumatic brain injury, hypoxia, ischemia, perinatal asphyxia associated with fetal distress such as following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycaemia and status epilepticus, episodes of cerebral asphyxia associated with coronary bypass surgery, hypotensive episodes and hypertensive crises, cerebral trauma and spinal cord injury.

DESCRIPTION OF SPECIFIC EMBODIMENTS

Embodiments of this invention include compositions and methods for the treatment of brain damage, encompassing neural regeneration peptides (NRPs). NRPs can induce neuronal migration, neurite outgrowth, neural differentiation, neural survival and/or neural proliferation. NRPs may be NRP analogs, paralogs, orthologs and/or NRP prodrugs, and peptides encoded by human, mouse or other species' genes. Some of the NRPs described herein are based on predicted protein sequence based upon the previously sequenced oligonucleotides corresponding to the genes noted herein. Other peptides are synthetic, and at least some are presented as a C-terminal amidated form. However, it can be appreciated that non-amidated forms of the proteins and peptides are to be included within the scope of this invention.

The nucleotide sequence (SEQ ID NO: 1) and amino acid sequence (SEQ ID NO: 2) of rat NRP-1 are:

```
                9                   18                  27                  36
5' tat gat cca gag gcc gcc tct gcc cca gga tcg ggg
   Tyr Asp Pro Glu Ala Ala Ser Ala Pro Gly Ser Gly 45
   aac cct tgc cat 3'                                    SEQ ID NO:1
   Asn Pro Cys His-NH₂                                   SEQ ID NO:2
```

Due to the degeneracy of the genetic code, however, multiple codons may encode the same amino acid. Thus, various nucleic acid sequences may encode for the same amino acid sequence. Each of these variations can be translated into SEQ ID NO: 2, and thus, all of these variations are included within the scope of this invention. For example, multiple nucleic acid sequences, including the nucleic acid sequence listed in SEQ ID NO: 1, encode for the rat NRP-1 amino acid sequence. The invention further comprises variants of the nucleotide sequence of SEQ ID NO: 1, including variants which preserve the amino acid sequence encoded by the nucleic acid sequences, as well as nucleic acid sequences which encode for rat NRP-1 analogs and NRP-1 orthologs and/or paralogs. By way of example only, variants of SEQ ID NO: 1 according to the genetic code for DNA are listed below, with each codon separated by a space from neighbouring codons, and where a nucleic acid following a "/" is a variant for the nucleic acid preceding the "/":

```
5' tat/c gat/c cca/t/c/g gag/a gcc/g/a/t gcc/g/a/t
tct/a/c/g gcc/g/a/t cca/t/c/g gga/t/c/g tcg/a/t/c
ggg/a/t/c aac/t cct/a/c/g tgc/t cat/c 3'
```

The above sequence, including the indicated variants, may be written using the letters r, y and n as defined above to provide the following sequence:

```
                                                        SEQ ID NO:3
5' tay gay ccn gar gcn gcn tcn gcn ccn ggn
tcn ggn aay ccn tgy cay 3'
```

It will be understood that other nucleotide sequences encoding other NRPs can vary according to the redundancy of the genetic code. Moreover, RNA as well as DNA may encode the peptides of the invention, and that where a nucleic acid is a RNA nucleic acid, uracil may be substituted for thymine.

A human gene was annotated using the human cachexia cDNA (U.S. Pat. No: 5,834,192) as a template. A survival-promoting peptide has more than 96% identity to a survival-promoting peptide (Cunningham et al., 1998) and rat NRP-1 has 100% identity to the cachexia protein and is the only NRP-1 homologue with known respective cDNA. Human cachexia protein is localised on chromosome 12 within the region of base pairs 621841-625428 and consists of 5 exons. We have compared the cachexia mRNA splice sites with the identified NRP human paralog on chromosome 13 (genomic clone from the Sanger Sequencing Centre—bA87G1: base pairs 77232-76768) and have annotated the coding region of a NRP-1 human ortholog (this ortholog is herein termed NRP-2). The nucleotide and amino acid sequences relating to NRP-2 are:

```
                              SEQ ID NOs: 4 and 5
                9                   18                  27                  36
5' atg aga gtc aga gta caa ctc aag tct aat gtc caa gtt gga
   Met Arg Val Arg Val Gln Leu Lys Ser Asn Val Gln Val Gly 45                  54                  63                  72                  81
E,UNS gca gga cac tca gcaatg aga gtc aga gta caa ctc aag tct aat gtc caa gtt aag
   gat cca gag gca agg aga gca cct
   Ala Gly His Ser Ala Lys Asp Pro Glu Ala Arg Arg Ala Pro 90                  99                  108                 117                 126
   gga agc cta cat ccc tgt cta gca gca tca tgc tca gct gct
   Gly Ser Leu His Pro Cys Leu Ala Ala Ser Cys Ser Ala Ala 135                 144                 153                 162
   ggc ctg cac aca agc tcg tgg aag aac ctg ttt ttg ata gaa
   Gly Leu His Thr Ser Ser Trp Lys Asn Leu Phe Leu Ile Glu 171                 180                 189                 198                 207
   gga cta gta agt att tgc cta ggg cac ata gtt gta caa gag
   Gly Leu Val Ser Ile Cys Leu Gly His Ile Val Val Gln Glu 216                 225                 234                 243                 252
   acg gac gtt ttt agg tcc ttg cgg ttt ctt gca ttt cca gaa
   Thr Asp Val Phe Arg Ser Leu Arg Phe Leu Ala Phe Pro Glu 261                 270                 279                 288
   aac ttg ctt caa ata ttt ttc cag atg caa aat tcc ttg gat
   Asn Leu Leu Gln Ile Phe Phe Gln Met Gln Asn Ser Leu Asp
```

-continued

SEQ ID NOs: 4 and 5

```
297         306             315             324             330
cct tgt ttt aga atg aat cta tta aaa act tca cat taa 3'    SEQ ID NO:4
Pro Cys Phe Arg Met Asn Leu Leu Lys Thr Ser His *stop     SEQ ID NO:5
```

The underlined nucleotide sequence denotes the signal peptide.

The protein-encoding DNA sequence consists of 4 exons as predicted by splice site analysis taking the sequence of the paralog form of the human cachexia gene (cDNA from U.S. Pat. No. 5,834,192) on chromosome 12 as a template. The chromosome map of the genomic clone bA87G1 is considered as the basis for the exact exon localisation. Exon 1 is located between bp 77232-77170. Exon 2 is located between bp 77088-77046. Exon 3 is located between bp 77036-76824.

between the base pairs 34764-33003 on the reverse complement strand of chromosome 3 (region according the Double Twist human genome annotation project). The protein coding sequence consists of 5 exons with the following locations: exon 1: 34764-34743; exon 2: 34729-34700; exon 3: 33745-33596; exon 4: 33498-33459; exon 5: 33043-33003. The nucleotide sequence (SEQ ID NO: 6) has 333 nucleotides and the amino acid sequence (SEQ ID NO: 7; herein termed NRP-3) has 111 amino acids, as denoted below.

SEQ ID NOs: 6 and 7

```
         9               18              27              36
5' atg aaa ata aat gta tta att aaa tta atg acc aag tca gat
   Met Lys Ile Asn Val Leu Ile Lys Leu Met Thr Lys Ser Asp 45          54              63              72              81
   tct ttt aaa agc caa gcc agg ggc caa gtt ccc cca ttt cta
   Ser Phe Lys Ser Gln Ala Arg Gly Gln Val Pro Pro Phe Leu 90          99              108             117             126
   ggg ggg gtg ggg tgc ccc tgg ttt ttt caa aca agg ttt tgg
   Gly Gly Val Gly Cys Pro Trp Phe Phe Gln Thr Arg Phe Trp 135             144             153             162
   ggc cat agt ttt gca gtt aaa ctg gcc tcc aac ctt tcc cag
   Gly His Ser Phe Ala Val Lys Leu Ala Ser Asn Leu Ser Gln 171         180             189             198             207
   gca gag aaa ttg gtc ctt cag caa acc ctt tcc caa aaa ggc
   Ala Glu Lys Leu Val Leu Gln Gln Thr Leu Ser Gln Lys Gly 216             225             234             243             252
   cta gac gga gca aaa aaa gct gtg ggg gga ctc gga aaa cta
   Leu Asp Gly Ala Lys Lys Ala Val Gly Gly Leu Gly Lys Leu 261             270             279             288
   gga aaa gat gca gtc gaa gat cta gaa agc gtg ggt aaa gga
   Gly Lys Asp Ala Val Glu Asp Leu Glu Ser Val Gly Lys Gly 297         306             315             324             333
   gcc gtc cat gac gtt aaa gac gtc ctt gac tca gta cta tag 3'   SEQ ID NO:6
   Ala Val His Asp Val Lys Asp Val Leu Asp Ser Val Leu *stop    SEQ ID NO:7
```

Exon 4 is located between base pairs 76778-76768 followed by the translation stop codon TAA. The translated protein consists of 110 amino acids, is identical in length to the human cachexia protein, and has 24.5% overall identity to human cachexia protein. Sequence comparison of the signal peptides for extracellular localisation (amino acids 1-19) of both proteins reveals 31.6% identity. Significantly, comparison of the first 30 amino acids of the mature (cleaved) peptide reveals 46.7% amino acid identity. Furthermore this peptide has similar neuronal migration, proliferation, survival and neurite outgrowth activities as NRP-1 (see FIGS. 16, 17 and 18).

A second ortholog of NRP-1 has been annotated, and is encoded by a DNA sequence from the human genome located These sequences belong to the human gene family of NRPs, and it is herein termed NRP-3. The sequence has 50% identity and 62.7% similarity to the human cachexia-associated protein. Furthermore, the peptide encoded by this nucleotide sequence has similar properties to NRP-1.

A third NRP-1 ortholog has been annotated is contained in the DNA sequence from the human genome located between the region 21970003-21972239 on the forward strand of human chromosome 15 (region according NCBI human genome annotation project). The protein coding sequence consists of 6 exons with the following locations: exon 1: 21970003-21970031; exon 2: 21970515-21970545; exon 3: 21970571-21970644; exon 4: 21970818-21970861; exon 5: 21971526-21971731; exon 6: 21972189-21972239. This gene has been re-sequenced and now is believed to be reflected in SEQ ID NO:48 and SEQ ID NO:49 below. However, the resequencing of the gene has not altered the NRP encoded thereby. The sequence consists of 435 nucleic acids that encode 145 amino acids. The nucleotide sequence (SEQ ID NO: 8) and predicted amino acid sequence (SEQ ID NO:9; herein termed NRP-4) are:

not appear to affect the sites relevant to neuroprotective effects of peptides derived from SEQ ID NO:8 or SEQ ID NO:9.

Another human ortholog ("NRP-5") of rat NRP-1 is encoded by the DNA sequence located within the Homo sapiens chromosome 7 working draft (NCBI: ref/NT_007933.9/Hs7_8090) of the NCBI database on the reverse

```
                              SEQ ID NO: 8 and 9

9             18            27            36
5' atg gct gtt gtg tta ctt gca cca ttt ggg gac atc agc cag
   Met Ala Val Val Leu Leu Ala Pro Phe Gly Asp Ile Ser Gln 45          54            63            72          81
   gaa atc aca aag gtt ggg aca ggg act cca ggg agg gct gag
   Glu Ile Thr Lys Val Gly Thr Gly Thr Pro Gly Arg Ala Glu 90            99           108           117           126
   gcc ggg ggc cag gtg tct cca tgc ctg gcg gcg tcc tgc agt
   Ala Gly Gly Gln Val Ser Pro Cys Leu Ala Ala Ser Cys Ser 135           144           153           162
   cag gcc tat ggc gcc atc ttg gct cac tgc aac ctc tgc ctc
   Gln Ala Tyr Gly Ala Ile Leu Ala His Cys Asn Leu Cys Leu 171           180           189           198           207
   cca ggt tca atg att aaa aaa aag aag aaa ttt ata gtt gaa
   Pro Gly Ser Met Ile Lys Lys Lys Lys Lys Phe Ile Val Glu 216           225           234           243           252
   ata gaa agt caa cct tta aag tct tac agg gaa aat tct acc
   Ile Glu Ser Gln Pro Leu Lys Ser Tyr Arg Glu Asn Ser Thr 261           270           279           288
   cat ttt ccc aga cca gtc cta aat ctt atg cga aaa cac tgt
   His Phe Pro Arg Gly Val Leu Asn Leu Met Arg Lys His Cys 297           306           315           324           333
   ggg gaa aag ggg gaa gaa ggg cct tgt ttc tct ccc aag caa
   Gly Glu Lys Gly Glu Glu Gly Pro Cys Phe Ser Pro Lys Gln 342           351           360           369           378
   atg ggg gag agg cga gnn tgt ggc gga ggg cta ggg ttg gct
   Met Gly Glu Arg Arg XXX Cys Gly Gly Gly Leu Gly Leu Ala 387           396           405           414
   cgc gag atc act aat tta aca tcc gct cat ctg ttg gtc ttg
   Arg Glu Ile Thr Asn Leu Thr Ser Ala His Leu Leu Val Leu 423           432 435
   aat atc agc aac cag tga 3'                                   SEQ
                                                                ID
                                                                NO:8
   Asn Ile Ser Asn Gln *stop                              SEQ ID NO:9
```

This sequence belongs to the human gene family NRPs. This sequence has 45% amino acid similarity to the NRP encoded by a nucleic acid sequence located on human chromosome 13. Triplet 244-246 (amino acid position 82); triplet 391-393 (amino acid position 131) and triplet 421-423 (amino acid position 141) encode potential N-glycosylation sites. Amino acid position 118 has an x because of uncertainty within the nucleic acid sequence. The peptide, NRP-4, exhibits neural proliferation promoting activity, neurite outgrowth and neuronal survival promoting activities. Note that in oligonucleotide position 353-354, the nucleotide had not been determined and the corresponding amino acid is not known. However, subsequent to the publication of the above sequence, a correct sequence has been provided and is described herein as Example 26, SEQ ID NO: 48 and SEQ ID NO:49. We note that the change in sequence information does strand. The protein coding sequence has been annotated and consists of 3 exons with 798 nucleic acids in total length coding for 266 amino acids. The exact locations for the protein coding exons are the following: exon 1: 15047153-15046815; exon 2: 14897885-14897772; exon 3: 14824386-14824042. There exists evidence from a human EST (GenBank AW138864) that the mRNA is expressed. The nucleotide sequence (SEQ ID NO:10) and the amino acid sequence (SEQ ID NO: 11; NRP-5) are as follows:

```
                   SEQ ID NOs: 10 and 11

9             18            27            36
5' atg ctg gac ccg tct tcc agc gaa gag gag tcg gac gag ggg
   Met Leu Asp Pro Ser Ser Ser Glu Glu Glu Ser Asp Glu Gly
```

SEQ ID NOs: 10 and 11 (continued)

```
         45                   54                   63                   72                   81
         ctg  gaa  gag  gaa  agc  cgc  gat  gtg  ctg  gtg  gca  gcc  ggc  agc
         Leu  Glu  Glu  Glu  Ser  Arg  Asp  Val  Leu  Val  Ala  Ala  Gly  Ser 90                   99                  108                  117                  126
         tcg  cag  cga  gct  cct  cca  gcc  ccg  act  cgg  gaa  ggg  cgg  cgg
         Ser  Gln  Arg  Ala  Pro  Pro  Ala  Pro  Thr  Arg  Glu  Gly  Arg  Arg 135                  144                  153                  162
         gac  gcg  ccg  ggg  cgc  gcg  ggc  ggc  ggc  ggc  gcg  gcc  aga  tct
         Asp  Ala  Pro  Gly  Arg  Ala  Gly  Gly  Gly  Gly  Ala  Ala  Arg  Ser 171                  180                  189                  198                  207
         gtg  agc  ccg  agc  ccc  tct  gtg  ctc  agc  gag  ggg  cga  gac  gag
         Val  Ser  Pro  Ser  Pro  Ser  Val  Leu  Ser  Glu  Gly  Arg  Asp  Glu 216                  225                  234                  243                  252
         ccc  cag  cgg  cag  ctg  gac  cat  gag  cag  gag  cgg  agg  atc  cgc
         Pro  Gln  Arg  Gln  Leu  Asp  Asp  Glu  Gln  Glu  Arg  Arg  Ile  Arg 261                  270                  279                  288
         ctc  cag  ctc  tac  gtc  ttc  gtc  gtg  agg  tgc  atc  gcg  tac  ccc
         Leu  Gln  Leu  Tyr  Val  Phe  Val  Val  Arg  Cys  Ile  Ala  Tyr  Pro 297                  306                  315                  324                  333
         ttc  aac  gcc  aag  cag  ccc  acc  gac  atg  gcc  cgg  agg  cag  cag
         Phe  Asn  Ala  Lys  Gln  Pro  Thr  Asp  Met  Ala  Arg  Arg  Gln  Gln 342                  351                  360                  369                  378
         aag  ctt  aac  aaa  caa  cag  ttg  cag  ttg  ctg  aaa  gaa  cgg  ttc
         Lys  Leu  Asn  Lys  Gln  Gln  Leu  Gln  Leu  Leu  Lys  Glu  Arg  Phe 387                  396                  405                  414
         cag  gcc  ttc  ctc  aat  ggg  gaa  acc  caa  att  gta  gct  gac  gaa
         Gln  Ala  Phe  Leu  Asn  Gly  Glu  Thr  Gln  Ile  Val  Ala  Asp  Glu 423                  432                  441                  450                  459
         gca  ttt  tgc  aac  gca  gtt  cgg  agt  tat  tat  gag  gtt  ttt  cta
         Ala  Phe  Cys  Asn  Ala  Val  Arg  Ser  Tyr  Tyr  Glu  Val  Phe  Leu 468                  477                  486                  495                  504
         aag  agt  gac  cga  gtg  gcc  aga  atg  gta  cag  agt  gga  ggg  tgt
         Lys  Ser  Asp  Arg  Val  Ala  Arg  Met  Val  Gln  Ser  Gly  Gly  Cys 513                  522                  531                  540
         tct  gct  aag  gac  ttc  aga  gaa  gta  ttt  aag  aaa  aac  ata  gaa
         Ser  Ala  Asn  Asp  Phe  Arg  Glu  Val  Phe  Lys  Lys  Asn  Ile  Glu 549                  558                  567                  576                  585
         aaa  cgt  gtg  cgg  agt  ttg  cca  gaa  gtg  gat  ggc  ttg  agc  aaa
         Lys  Arg  Val  Arg  Ser  Leu  Pro  Glu  Val  Asp  Gly  Leu  Ser  Lys 594                  603                  612                  621
         gag  aca  gtg  ttg  agc  tca  tgg  ata  gcc  aaa  tat  gat  gcc  att
         Glu  Thr  Val  Leu  Ser  Ser  Trp  Ile  Ala  Lys  Tyr  Asp  Ala  Ile 630                  639                  648                  657                  666
         tac  aga  ggt  gaa  gag  gac  ttg  tgc  aaa  cag  cca  aat  aga  atg
         Tyr  Arg  Gly  Glu  Glu  Asp  Leu  Cys  Lys  Gln  Pro  Asn  Arg  Met 675                  684                  693                  702                  711
         gcc  cta  agt  gca  gtg  tct  gaa  ctt  att  ctg  agc  aag  gaa  caa
         Ala  Leu  Ser  Ala  Val  Ser  Glu  Leu  Ile  Leu  Ser  Lys  Glu  Gln 720                  729                  738                  747
         ctc  tat  gaa  atg  ttt  cag  cag  att  ctg  ggt  att  aaa  aaa  ctg
         Leu  Tyr  Glu  Met  Phe  Gln  Gln  Ile  Leu  Gly  Ile  Lys  Lys  Leu 756                  765                  774                  783                  792
         gaa  cac  cag  ctc  ctt  tat  aat  gca  tgt  cag  gta  agt  ggt  ctc
         Glu  His  Gln  Leu  Leu  Tyr  Asn  Ala  Cys  Gln  Val  Ser  Gly  Leu 798
         tga 3'                                                              SEQ ID NO: 10
         *stop                                                               SEQ ID NO: 11
```

The entire protein NRP-5 consists of 266 amino acids. The annotated translated NRP amino acid sequence NRP-5 has 76% similarity to a human calcium dependent activator protein of secretion (GenBankXP_036915) located on chromosome 3. Furthermore, exon 1 (339 nucleic acids) of the translated human chromosome 7 NRP-5 has 95.5% homology to a translated mouse 5' EST (RIKENBB632392). This protein shares domains present in NRP-1 and other NRPs that exhibit biological properties of neurite outgrowth, neuronal survival, neuronal proliferation and neuronal migration.

We have annotated a DNA sequence from the human genome located between the regions 116668725-116667697 on the reverse complement strand of chromosome 6 (region according NCBI human genome annotation project). The protein coding sequence consists of 3 exons with the following locations: exon 1: 116668725-116668697, exon 2: 116668333-116668305, and exon 3: 116667872-116667697. The sequence, herein termed NRP-6 consists of 234 nucleic acids that encode 78 amino acids. This sequence belongs to the human gene family of NRPs. The highest homology found to human ESTs presents identity from nucleic acids 59-234 compared to the human cDNA clone GenBankCSODK001YI19 isolated from human placental tissue. This clone was sequenced from the 3'-prime end and consists of 924 nucleic acids. Because our homologue form ends with the stop codon TGA after 234 nucleic acids we are not dealing with the same gene product. The nucleotide sequence (SEQ ID NO: 12) encoding for an NRP, and the amino acid sequence (SEQ ID NO: 13; NRP-6) for the peptide is:

SEQ ID NOs: 12 and 13

```
                        9                   18                   27                   36
    5'  atg  aga  gac  aaa  caa  cat  cta  aat  gca  aga  cat  aaa  aag  gaa
        Met  Arg  Asp  Lys  Gln  His  Leu  Asn  Ala  Arg  His  Lys  Lys  Glu 45                   54                   63                   72                   81
        agg  aag  gag  aga  tca  tat  agt  aca  aca  cta  caa  ggt  gtt  ctc
        Arg  Lys  Glu  Arg  Ser  Tyr  Ser  Thr  Thr  Leu  Gln  Gly  Val  Leu 90                   99                  108                  117                  126
        aac  aaa  aag  tct  ttg  tta  gac  ttc  aat  aat  act  att  tgg  tac
        Asn  Lys  Lys  Ser  Leu  Leu  Asp  Phe  Asn  Asn  Thr  Ile  Trp  Tyr
```

SEQ ID NOs: 12 and 13

|     |     | 135 |     |     | 144 |     |     | 153 |     |     | 162 |     |     |             |
| --- | --- | --- | --- | --- | --- | --- | --- | --- | --- | --- | --- | --- | --- | ----------- |
| ttc | tat | cag | caa | ata | gga | agc | att | cca | ata | ctt | att | aga | tcc |             |
| Phe | Tyr | Gln | Gln | Ile | Gly | Ser | Ile | Pro | Ile | Leu | Ile | Arg | Ser |             |
| 171 |     |     | 180 |     |     | 189 |     |     | 198 |     |     | 207 |     |             |
| tct | acc | atc | aga | cac | aga | aat | tac | cta | gaa | aac | aga | aat | gta |             |
| Ser | Thr | Ile | Arg | His | Arg | Asn | Tyr | Leu | Glu | Asn | Arg | Asn | Val |             |
|     | 216 |     |     | 225 |     |     | 234 |     |     |     |     |     |     |             |
| ttg | cca | aat | ctc | aaa | caa | gag | ggc | tga | 3'  |     |     |     |     | SEQ ID NO:12 |
| Leu | Pro | Asn | Leu | Lys | Gln | Glu | Gly | *stop |   |     |     |     |     | SEQ ID NO:13 |

The amino acid sequence of NRP-6 has 14.1% identity and 44.9% similarity to the annotated NRP paralog on human chromosome 13, NRP-2. This protein shares domains present in NRP-1 and other NRPs (e.g., NRPs 2-5) that have biological properties of neurite outgrowth, neuronal survival, neuronal proliferation and neuronal migration.

Furthermore, another NRP-1 ortholog has been identified, a mouse NRP family member. The mouse NRP family member (here indicated as protein 2, SEQ ID NO:17; herein termed NRP-7) is located within the arachne contig_191157 of NCBI consisting of 339 nucleic acids using reading frame 1. Within an overlapping region there is a second ORF of 198 nucleic acids starting at position 29 of the annotated NRP paralog using frame 3. This ORF codes for a protein (here indicated as protein 1) with high identity to a truncated human DNA repair protein. By using the search paradigm tBLASTN using the biological active NRP peptide sequence: KDPEAR-RAPGSLHPCLAASCSAAG-NH$_2$ (SEQ ID NO:18) we got a blast hit in the mouse EST RIKEN database. This 5'-generated mouse EST has the accession number GenBankAKO12518 and the following sequence (SEQ ID NO:14):

5'-GGCAGCCTCGAGATGGGGAAGATGGCGGCTGCTG SEQ ID NO:14

TGGCTTCATTAGCCACGCTGGCTGCAGAGCCCAGAGA

GGATGCTTTCCGGAAGCTTTTCCGCTTCTACCGGCAG

AGCCGGCCGGGGACAGCGGACCTGGGAGCCGTCATCG

ACTTCTCAGAGGCGCACTTGGCTCGGAGCCCGAAGCC

CGGCGTGCCCCAGGTAGGAAAGGAGGAGTAGTGTGTG

CCAGCCTAGCGGCCGACTGGGCCACCCGAGACTGGGC

CGCCTCCGGGCCGGCTTTGGAGGGAAGCCCCTGCTGG

GCCTGTCCAGTGAGCTGTAATGTCGAGCGATGAGCGA

CCAGCTGCCTCGCTGTCCCAACGCTCTGGCCACGGCT

TGTGCCTTGCCGCCATTTCCCCCAACCCACGCGGGCC

ACGGCTTGTGCCCTGCCGCCATTTCCCCCAACCCACG

CGACCTTGCTC-3'

Protein 1 Reading Frame 3

Translation of open reading frame 3 (ORF of 198 nucleic acids starting at position 13 of the EST) reveals the following protein sequence (SEQ ID NO: 15):

SEQ ID NO:15
MGKMAAAVASLATLAAEPREDAFRKLFR-
FYRQSRPGTADLGAVIDFSEAHLA

RSPKPGVPQVGKEE

This sequence has 82% homology (identity and chemical similarity) of amino acid sequence to the human alkylated DNA repair protein with the GenBank accession number Q13686. The mouse form is C-terminal truncated and has only 66 of the 389 amino acids of the human DNA repair protein.

Protein 2 Reading Frame 1

An even longer ORF of 323 nucleic acids can be found within frame 1 of the EST sequence. We then annotated the 5' end of the 323 nucleic acid ORF in the mouse genome and found a new gene located in the mouse arachne contig_191157 sequence of the NCBI database between 23970 and 24374. The protein coding sequence consists of two exons with an overall length of 339 nucleic acids coding for 113 amino acids. The location of exon 1 is: 23970-23990, and for exon 2 it is: 24057-24374. The nucleotide sequence (SEQ ID NO:16) and the amino acid sequence (SEQ ID NO:17; NRP-7) of this mouse NRP ortholog of rat NRP-1 are:

SEQ ID NOs: 16 and 17

|     |     |     | 9   |     |     | 18  |     |     | 27  |     |     | 36  |     |
| --- | --- | --- | --- | --- | --- | --- | --- | --- | --- | --- | --- | --- | --- |
| 5' atg | aat | cga | aac | cct | gga | gtc | cct | cga | gat | ggg | gaa | gat | ggc |
| Met | Asn | Arg | Asn | Pro | Gly | Val | Pro | Arg | Asp | Gly | Glu | Asp | Gly |
|     | 45  |     |     | 54  |     |     | 63  |     |     | 72  |     |     | 81  |
| ggc | tgc | tgt | ggc | ttc | att | agc | cac | gct | ggc | tgc | aga | gcc | cag |
| Gly | Cys | Cys | Gly | Phe | Ile | Ser | His | Ala | Gly | Cys | Arg | Ala | Gln |
|     | 90  |     |     | 99  |     |     | 108 |     |     | 117 |     |     | 126 |

-continued

SEQ ID NOs: 16 and 17

```
aga gga tgc ttt ccg gaa gct ttt ccg ctt cta ccg gca gag
Arg Gly Cys Phe Pro Glu Ala Phe Pro Leu Leu Pro Ala Glu 135             144             153             162
ccg gcc ggg gac agc gga cct ggg agc cgt cat cga ctt ctc
Pro Ala Gly Asp Ser Gly Pro Gly Ser Arg His Arg Leu Leu 171             180             189             198             207
aga ggc gca ctt ggc tcg gag ccc gaa gcc cgg cgt gcc cca
Arg Gly Ala Leu Gly Ser Glu Pro Glu Ala Arg Arg Ala Pro 216             225             234             243             252
ggt agg aaa gga gga gta gtg tgt gcc agc cta gcg gcc gac
Gly Arg Lys Gly Gly Val Val Cys Ala Ser Leu Ala Ala Asp 261             270             279             288
tgg gcc acc cga gac tgg gcc gcc tcc ggg ccg gct ttg gag
Trp Ala Thr Arg Asp Trp Ala Ala Ser Gly Pro Ala Leu Glu 297             306             315             324             333
gga agc ccc tgc tgg gcc tgt cca gtg agc tgt aat gtc gag
Gly Ser Pro Cys Trp Ala Cys Pro Val Ser Cys Asn Val Glu 339
cga tga 3'                                                          SEQ ID NO:16
Arg *stop                                                           SEQ ID NO:17
```

The entire expressed amino acid sequence of NRP-7 contains 113 amino acids (SEQ ID NO:17). An alternative version of NRP-7 is an alternatively spliced form containing an additional 66 nucleotides after position 21 of SEQ ID NO:16 (SEQ ID NO:35), which produces a long form of NRP-7 ("NRP-7 long") having 135 amino acids (SEQ ID NO:36).

```
                    9               18              27              36
5'  ATG AAT CGA AAC CCT GGA GTC GTG ACC CCG GAA GAA CCT GCC
    Met Asn Arg Asn Pro Gly Val Val Thr Pro Glu Glu Pro Ala 45              54              63              72              81
    AGA GCC GGA ATT TCG AGT TCT GCT TCC GGG CCA AAC TGT TGG
    Arg Ala Gly Ile Ser Ser Ser Ala Ser Gly Pro Asn Cys Trp 90              99              108             117             126
    CAG CCT CGA GAT GGG GAA GAT GGC GGC TGC TGT GGC TTC ATT
    Gln Pro Arg Asp Gly Glu Asp Gly Gly Cys Cys Gly Phe Ile 135             144             153             162
    AGC CAC GCT GGC TGC AGA GCC CAG AGA GGA TGC TTT CCG GAA
    Ser His Ala Gly Cys Arg Ala Gln Arg Gly Cys Phe Pro Glu 171             180             189             198             207
    GCT TTT CCG CTT CTA CCG GCA GAG CCG GCC GGG GAC AGC GGA
    Ala Phe Pro Leu Leu Pro Ala Glu Pro Ala Gly Asp Ser Gly 216             225             234             243             252
    CCT GGG AGC CGT CAT CGA CTT CTC AGA GGC GCA CTT GGC TCG
    Pro Gly Ser Arg His Arg Leu Leu Arg Gly Ala Leu Gly Ser 261             270             279             288
    GAG CCC GAA GCC CGG CGT GCC CCA GGT AGG AAA GGA GGA GTA
    Glu Pro Glu Ala Arg Arg Ala Pro Gly Arg Lys Gly Gly Val 297             306             315             324             333
    GTG TGT GCC AGC CTA GCG GCC GAC TGG GCC ACC CGA GAC TGG
    Val Cys Ala Ser Leu Ala Ala Asp Trp Ala Thr Arg Asp Trp 342             351             360             369             378
    GCC GCC TCC GGG CCG GCT TTG GAG GGA AGC CCC TGC TGG GCC
    Ala Ala Ser Gly Pro Ala Leu Glu Gly Ser Pro Cys Trp Ala 387             396             405 408     3'
    TGT CCA GTG AGC TGT AAT GTC GAG CGA TGA (*stop)                 SEQ ID NO:35
    Cys Pro Val Ser Cys Asn Val Glu Arg                             SEQ ID NO:36
```

The protein function program tool SAMRT predicts a signal peptide sequence consisting of 28 amino acids. The protein has 13.6% identity and 23.6% similarity towards the NRP ortholog on human chromosome 13, and has neuronal survival, migration, proliferation and outgrowth activity similar to NRP-1.

A second mouse NRP family member is located within the genomic clone bM344E9 of the mouse Sanger database on the reverse complement strand. By using the search program tBLASTN using the biologically active NRP peptide sequence: KDPEARRAPGSLHPCLAASCSAAG-NH$_2$ (SEQ ID NO:18) we obtained an area of similarity in the genomic mouse Sanger database within the genomic clone bM344E9. The protein coding sequence has been annotated and consists of 5 exons and is 423 nucleic acids in total length coding for 141 amino acids. The locations for the coding exons are the following: exon 1: 5609-5596, exon 2: 5502-5489, exon 3: 5398-5283, exon 4: 5243-5229, and exon 5: 5215-4952. The coding nucleotide sequence (SEQ ID NO:19) and the amino acid sequence (SEQ ID NO:20) of the mouse ortholog of rat NRP-1 (herein termed NRP-8) is:

The expressed amino acid sequence of NRP-8 contains 141 amino acid residues. The asparagine residue at position 112-114 is putatively N-glycosylated according to the occurrence of an N-glycosylation consensus sequence. The new mouse NRP-1 ortholog NRP-10 has 35.5% homology to the human NRP ortholog located on chromosome 13 (NRP-2) and 28.9% homology to the mouse NRP-1 ortholog located on the arachne contig from NCBI. Furthermore this peptide comprises amino acid sequence domains similar to those present in NRP-1 or other NRP peptides and this peptide has biological properties including promotion of neuronal migration, proliferation, survival and/or neurite outgrowth.

The nucleotide sequence (SEQ ID NO:27) and the amino acid sequence (SEQ ID NO:28) of NRP-9, the rat ortholog of mouse NRP-7 is:

---

SEQ ID NOs: 19 and 20

```
                  9                   18                  27                  36
5'  atg  tgc  act  ctg  cag  gta  tgg  tct  tcc  tcc  ctc  cct  tcc  ctc
    Met  Cys  Thr  Leu  Gln  Val  Trp  Ser  Ser  Ser  Leu  Pro  Ser  Leu 45             54                  63                  72                  81
    ccc  cac  ctc  tct  gag  ggg  tca  ggg  gtc  agc  att  tgg  atg  ctg
    Pro  His  Leu  Ser  Glu  Gly  Ser  Gly  Val  Ser  Ile  Trp  Met  Leu 90                  99                 108                 117            126
    ctc  cca  cca  ggc  cca  gct  tta  gaa  atg  aat  tcc  tcc  ggc  ctc
    Leu  Pro  Pro  Gly  Pro  Ala  Leu  Glu  Met  Asn  Ser  Ser  Gly  Leu 135                 144                 153                 162
    ctt  tat  act  ctt  gag  acc  tcc  tgg  gga  acc  agg  acc  ctc  ttg
    Leu  Tyr  Thr  Leu  Glu  Thr  Ser  Trp  Gly  Thr  Arg  Thr  Leu  Leu 171            180                 189                 198                 207
    gct  cct  ctg  gtg  aca  tac  atg  gga  tct  gat  gca  tct  gag  gtg
    Ala  Pro  Leu  Val  Thr  Tyr  Met  Gly  Ser  Asp  Ala  Ser  Glu  Val 216                 225                 234                 243            252
    gat  gca  aga  aga  gca  aaa  aag  agt  ctc  cac  tgc  atc  ctg  tct
    Asp  Ala  Arg  Arg  Ala  Lys  Lys  Ser  Leu  His  Cys  Ile  Leu  Ser 261                 270                 279                 288
    gac  acc  agc  cat  ccc  cgg  ggc  cat  gcc  cgg  aat  gag  agg  agg
    Asp  Thr  Ser  His  Pro  Arg  Gly  His  Ala  Arg  Asn  Glu  Arg  Arg 297            306                 315                 324                 333
    ctt  ggc  ctt  ggg  gtt  tgg  aag  acc  gag  ctt  tgg  gtc  cag  acc
    Leu  Gly  Leu  Gly  Val  Trp  Lys  Thr  Glu  Leu  Trp  Val  Gln  Thr 342                 351                 360                 369            378
    ctg  cta  tca  ctg  atg  gtg  aca  tcc  tgg  gaa  gtt  tat  gaa  act
    Leu  Leu  Ser  Leu  Met  Val  Thr  Ser  Trp  Glu  Val  Tyr  Glu  Thr 387                 396                 405                 414
    cgt  tcg  tgc  ctc  agt  ttc  ccc  atc  agg  cct  tta  gct  cac  tgg
    Arg  Ser  Cys  Leu  Ser  Phe  Pro  Ile  Arg  Leu  Leu  Ala  His  Trp 423
    gga  taa  3'   END                                                   SEQ ID NO:19
    Gly  *stop                                                            SEQ ID NO:20
```

|  |  |  |  |  |  |  |  |  |  |  |
|---|---|---|---|---|---|---|---|---|---|---|
| | | | | | SEQ ID NOs: 27 and 28 | | | | | |

```
1           9                       18                  27                      36                  45
ATG  TTA  AAA  CTG  AAT  GAA  CCA  AAG  CCT  GGG  GTC  GTG  ACC  TCG  GAA
Met  Leu  Lys  Leu  Asn  Glu  Pro  Lys  Pro  Gly  Val  Val  Thr  Ser  Glu 54                       63                  72                      82                  90
GAA  CTT  ACA  GGA  TCC  GGA  ATT  TGG  AGT  TCT  GCT  TCC  GGG  CCA  AAC
Glu  Leu  Thr  Gly  Ser  Gly  Ile  Trp  Ser  Ser  Ala  Ser  Gly  Pro  Asn 99                       108                 117                     126                 135
TGT  TCG  CAA  CAT  CGA  GAT  GGG  GAA  GAT  GGC  GGC  TGC  GGT  CGT  TTC
Cys  Ser  Gln  His  Arg  Asp  Gly  Glu  Asp  Gly  Gly  Cys  Gly  Arg  Phe 144                      153                 162                     171                 180
ATT  AAC  CTC  GCT  GGC  AAC  AGA  ACC  CAA  AGA  GGA  TGC  TTT  CCG  GAA
Ile  Asn  Leu  Ala  Gly  Asn  Arg  Thr  Gln  Arg  Gly  Cys  Phe  Pro  Glu 189                      198                 207                     216                 225
GCT  TTT  CCG  CTT  CTA  CAG  GCA  GAG  CCG  GCG  GAG  TAC  GGC  GGA  CCT
Ala  Phe  Pro  Leu  Leu  Gln  Ala  Glu  Pro  Ala  Glu  Tyr  Gly  Gly  Pro 234                      243                 252                     261                 270
AGG  AGC  GGT  CAT  CGA  CTT  CTC  AGA  GGC  TCA  CGT  GGC  TCA  GAG  CCC
Arg  Ser  Gly  His  Arg  Leu  Leu  Arg  Gly  Ser  Arg  Gly  Ser  Glu  Pro 279                      288                 297                     306                 315
GAA  GCC  CGG  CGT  GCC  CAA  GGT  GGT  CAG  ATT  CCC  TCT  GAA  CGT  GTC
Glu  Ala  Arg  Arg  Ala  Gln  Gly  Gly  Gln  Ile  Pro  Ser  Glu  Arg  Val

324
CTC  AGT  GAC  TGA                                                             SEQ ID NO:27
Leu  Ser  Asp  stop                                                            SEQ ID NO:28
```

In addition to the NRP compounds described above, we have identified other genes having NRP-like peptide domains that also can be useful for expressing NRPs. These include genes from mycobacteria and tumor cells. A recently published paper has disclosed a PE multigene family of Mycobacterium tuberculosis containing a consensus sequence (PE_PGRS) that is similar to our proposed sequence (PGR/S). They also mention that these proteins are released in the host, by the bacterium, to promote bacterial survival. Here are the examples they provided in the paper, where the PE_PGRS consensus sequence was found. The amino acid sequence of the Rv1818c gene product of M. tuberculosis (SEQ ID NO:21) is shown below:

```
MSFVVTIPEA  LAAVATDLAG  IGSTIGTANA  AAAVPTTTVL  AAAADEVSAA  MAALFSGHAQ  SEQ ID NO:21

AYQALSAQAA  LFHEQFVRAL  TAGAGSYAAA  EAASAAPLEG  VLDVINAPAL  ALLGRPLIGN

GANGAPGTGA  NGGDGGILIG  NGGAGGSGAA  GMPGGNGGAA  GLFGNGGAGG  AGGNVASGTA

GFGGAGGAGG  LLYGAGGAGG  AGGRAGGGVG  GIGGAGGAGG  NGGLLFGAGG  AGGVGGLAAD

AGDGGAGGDG  GLFFGVGGAG  GAGGTGTNVT  GGAGGAGGNG  GLLFGAGGVG  GVGGDGVAFL

GTAPGGPGGA  GGAGGLFGVG  GAGGAGGIGL  VGNGGAGGSG  GSALLWGDGG  AGGAGGVGST

TGGAGGAGGN  AGLLVGAGGA  GGAGALGGGA  TGVGGAGGNG  GTAGLLFGAG  GAGGFGFGGA

GGAGGLGGKA  GLIGDGGDGG  AGGNGTGAKG  GDGGAGGGAI  LVGNGGNGGN  AGSGTPNGSA

GTGGAGGLLG  KNGMNGLP
```

The amino acid sequence of Epstein-Barr Virus Nuclear Antigen 1 (SEQ ID NO:22) is shown below:

```
MSDEGPGTGP  GNGLGEKGDT  SGPEGSGGSG  PQRRGGDNHG  RGRGRGRGRG  GGRPGAPGGS    SEQ ID NO:22
GSGPRHRDGV  RRPQKRPSCI  GCKGTHGGTG  AGAGAGGAGA  GGAGAGGGAG  AGGGAGGAGG
AGGAGAGGGA  GAGGGAGGAG  GAGAGGGAGA  GGGAGGAGAG  GGAGGAGGAG  AGGGAGAGGG
AGGAGAGGGA  GGAGGAGAGG  GAGAGGAGGA  GGAGAGGAGA  GGGAGGAGGA  GAGGAGAGGA
GAGGAGAGGA  GGAGAGGAGG  AGAGGAGGAG  AGGGAGGAGA  GGGAGGAGAG  GAGGAGAGGA
GGAGAGGAGG  AGAGGGAGAG  GAGAGGGGRG  RGGSGGRGRG  GSGGRGRGGS  GGRRGRGRER
ARGGSRERAR  GRGRGRGEKR  PRSPSSQSSS  SGSPPRRPPP  GRRPFFHPVG  EADYFEYHQE
GGPDGEPDVP  PGAIEQGPAD  DPGEGPSTGP  RGQGDGGRRK  KGGWFGKHRG  QGGSNPKFEN
IAEGLRALLA  RSHVERTTDE  GTWVAGVFVY  GGSKTSLYNL  RRGTALAIPQ  CRLTPLSRLP
FGMAPGPGPQ  PGPLRESIVC  YFMVFLQTHI  FAEVLKDAIK  DLVMTKPAPT  CNIRVTVCSF
DDGVDLPPWF  PPMVEGAAAE  GDDGDDGDEG  GDGDEGEEGQ  E
```
20

From Brennan, M. J. and Delogu, G.,(2002). The PE multigene family: a 'molecular mantra' for mycobacteria. *Trends in Microbiology* 5: 246-249.

It can be appreciated that the entire sequence of NRP-1-NRP 9 need not be used. Rather, peptide fragments of about 8 amino acids can be used according to embodiments of this invention. Given the consensus sequence domains herein identified, one can fashion synthetic peptides or can truncate naturally occurring NRPs to obtain portions of peptides that are biologically active. Methods of truncation (e.g., using synthetic DNA) or enzymatic modification of expressed peptides are known in the art.

One embodiment of the invention is a 24-mer fragment of NRP-2 (SEQ ID NO:5) comprising the sequence KDPEAR-RAPGSLHPCLAASCSAAG-NH$_2$ (NRP-2 segment KG; SEQ ID NO:18).

Another embodiment of the invention is a 19-mer fragment of NRP-2 (SEQ ID NO: 5) comprising the sequence KDPE-ARRAPGSLHPCLAAS-NH$_2$ (NRP-2 segment KS; SEQ ID NO: 23).

Yet another embodiment of the invention is a 24-mer form of NRP-7 (SEQ ID NO: 17 or SEQ ID NO: 36) comprising the sequence SEPEARRAPGRKGGVVCASLAADW-NH$_2$ (NRP-7 segment SW; SEQ ID NO: 24).

Further embodiment of the invention is an 11-mer peptide comprising the sequence SDSFKSQARGQ-NH$_2$ (NRP-3 segment SQ; SEQ ID NO:25), located between amino acids 13-23 of NRP-3 (SEQ ID NO:7).

Another embodiment of the invention is an 11-mer peptide comprising sequence GTPGRAEAGGQ-NH$_2$ (NRP-4 segment GQ; SEQ ID NO: 26), located between amino acids 22-32 of the annotated NRP-4 (SEQ ID NO:9).

Another embodiment of the invention is a 25-mer fragment of NRP-4 (SEQ ID NO: 9) comprising sequence GTPGRAE-AGGQVSPCLAASCSQAYG-NH$_2$ (NRP-4 segment GQ; SEQ ID NO: 29)

Yet another embodiment of the invention is a 13-mer fragment of NRP-5 (SEQ ID NO: 11) comprising sequence REGRRDAPGRAGG-NH$_2$ (NRP-5 segment RG; SEQ ID NO: 30).

Still further embodiment of the invention is a 24-mer fragment of NRP-8 (SEQ ID NO 20) comprising sequence SEV-DARRAKKSLHCILSDTSHPRG-NH$_2$ (NRP-8 segment SG; SEQ ID NO: 31)

Yet another embodiment of the invention is a 24-mer fragment of NRP-3 (SEQ ID NO: 7) comprising sequence SDS-FKSQARGQVPPFLGGVGCPWF-NH$_2$ (NRP-3 segment SF; SEQ ID NO: 32)

Another embodiment of the invention is an 8-mer fragment of NRP-5 (SEQ ID NO: 11) comprising sequence REGR-RDAP-NH$_2$ (NRP-5 RP; SEQ ID NO: 33).

Additional embodiment of the invention is a 21-mer peptide comprising sequence SEPEARRAQGGQIPSERVLSD-NH$_2$ (NRP-9 segment SD; SEQ ID NO:34), which is located between amino acid residues 88-108 of NRP-9 (SEQ ID NO: 28).

Another embodiment of the invention is a 9-mer peptide comprising sequence PGRAEAGGQ-NH$_2$ (NRP-4 segment PQ; SEQ ID NO: 43), located between amino acids 24-32 of the annotated NRP-4 (SEQ ID NO:9). Further embodiments are described elsewhere herein.

Uses of NRP Compounds

Thus, the invention includes embodiments which relate to NRPs, peptides encoded by NRPs, homologs, orthologs or paralogs of NRPs, analogs of NRPs, and prodrugs of NRPs, where a prodrug of an NRP is a molecule that may be enzymatically, metabolically or otherwise modified to become an NRP, a NRP homolog, NRP paralog, an NRP ortholog or an NRP analog. Such molecules are collectively termed as "NRP compounds" or "NRPs." NRP compounds may be encoded for by nucleotide sequences, which may be DNA or RNA and which may be single stranded or double stranded. It will be understood that the invention includes sequences complementary to the sequences described in this application as well as the sequences themselves. It is also to be understood that there may be alternatively spliced forms of NRPs, in which case, those alternatively spliced forms of NRP RNA, and the proteins and peptides they may encode are also considered to be part of this invention.

As indicated above, embodiments of the present invention are based upon the inventors' surprising finding that NRPs can induce neurons and neuroblasts to proliferate, migrate, differentiate, produce neuritis and can protect neurons against damage caused by neural insults. Proliferation and migration of neural cells into areas of damage caused by acute brain injury or chronic neurodegenerative disease can result in improvement in neural functioning. Further, NRPs can promote neuronal survival, neuronal differentiation, and/or neurite outgrowth. Thus, NRP compounds may be used to treat a variety of disorders and conditions where brain tissue degenerates, is at risk of degeneration or death, or has died.

Cells can also use NRP oligonucleotides to stimulate production of NRPs after transfection. In some cases, transfection can be in a replicable vehicle, and in others, the NRP oligonucleotide can be introduced as naked DNA.

Disorders and Conditions Treatable with NRPs

Disorders and conditions in which NRP compounds can be of benefit include:

Infections of the central nervous system including bacterial, fungal, spirochetal, parasitic and sarcoid including pyrogenic infections, acute bacterial meningitis, leptomeningitis;

Cerebrovascular diseases including stroke, ischemic stroke, atherosclerotic thrombosis, lacunes, embolism, hypertensive haemorrhage, ruptured aneurysms, vascular malformations, transient ischemic attacks, intracranial haemorrhage, spontaneous subarachnoid haemorrhage, hypertensive encephalopathy, inflammatory diseases of the brain arteries, decreased perfusion caused by, for example, cardiac insufficiency (possibly resulting from coronary bypass surgery) and other forms of cerebrovascular disease;

Craniocerebral trauma including basal skull fractures and cranial nerve injuries, carotid-cavernous fistula, pneumocephalus, aerocele andrhinorrhea, cerebral contusion, traumatic intracerebral haemorrhage, acute brain swelling in children;

Demyelinating diseases include neuromyelitis optica, acute disseminated encephalomyelitis, acute and subacute necrotizing haemorrhagic encephalitis, diffuse cerebral sclerosis of Schilder and multiple sclerosis in conjunction with peripheral neuropathy. Degenerative diseases of the nervous system including syndrome of one or more of progressive dementia, diffuse cerebral atrophy, diffuse cortical atrophy of the non-Alzheimer type, Lewy body dementia, Pick's disease, fronto-temporal dementia, thalamic degeneration, non-Huntingtonian types of Chorea and dementia, cortico-spinal degeneration (Jakob), the dementia-Parkinson-amyotrophic lateral sclerosis complex (Guamanina and others);

Acquired metabolic disorders of the nervous system including metabolic diseases presenting as a syndrome comprising one or more of confusion, stupor or coma-ischemia-hypoxia, hypoglycaemia, hyperglycemia, hypercapnia, hepatic failure and Reye syndrome, metabolic diseases presenting as a progressive extrapyramidal syndrome, metabolic diseases presenting as cerebellar ataxia, hyperthermia, celiac-sprue disease, metabolic diseases causing psychosis or dementia including Cushing disease and steroid encephalopathy, thyroid psychosis and hypothyroidism, pancreatic encephalopathy;

Diseases of the nervous system due to nutritional deficiency;

Alcohol and alcoholism;

Disorders of the nervous system due to drugs and other chemical agents including opiates and synthetic analgesics, sedative hypnotic drugs, stimulants, psychoactive drugs, bacterial toxins, plant poisons, venomous bites and stings, heavy metals, industrial toxins, anti-neoplastic and immunosuppressive agents, thalidomide, aminoglycoside antibiotics (ototoxicity) and penicillin derivatives (seizures), cardioprotective agents (beta-blockers, digitalis derivatives and amiodarone).

As illustrated by the preceding list, compositions and methods of the invention can fmd use in the treatment of human neural injury and disease. Still more generally, the compositions and methods of the invention fmd use in the treatment of human patients suffering from neural damage as the result of acute brain injury, including but not limited to diffuse axonal injury, perinatal hypoxic-ischemic injury, traumatic brain injury, stroke, ischemic infarction, embolism, and hypertensive haemorrhage; exposure to CNS toxins, infections of the central nervous system, such as, bacterial meningitis; metabolic diseases such as those involving hypoxic-ischemic encephalopathy, peripheral neuropathy, and glycogen storage diseases; or from chronic neural injury or neurodegenerative disease, including but not limited to Multiple Sclerosis, Lewy Body Dementia, Alzheimer's disease, Parkinson's disease and Huntington's disease. Patient's suffering from such diseases or injuries may benefit greatly by a treatment protocol able to initiate neuronal proliferation and migration, as well as neurite outgrowth.

Still more generally, the invention has application in the induction of neuronal and neuroblast migration into areas of damage following insult in the form of trauma, toxin exposure, asphyxia or hypoxia-ischemia.

NRP compounds, including NRP-1, its orthologs, analogs, paralogs and prodrugs containing the identified NRP peptide domains, can be used to promote neuronal and neuroblast migration. Most conveniently, this can be affected through direct administration of NRP compounds to the patient.

However, while NRPs can be advantageously used, there is no intention to exclude administration of other forms of NRP compounds. For example, human paralog forms or peptide fragments of NRP can be administered in place of NRP. By way of example, the effective amount of NRP in the CNS can be increased by administration of a pro-drug form of NRP that comprises NRP and a carrier, NRP and the carrier being joined by a linkage that is susceptible to cleavage or digestion within the patient. Any suitable linkage can be employed which will be cleaved or digested to release NRP following administration.

Another suitable treatment method is for NRP levels to be increased through an implant that is or includes a cell line that is capable of expressing NRP or analogs, paralogs or propeptides of an NRP in an active form within the central nervous system of the patient.

An NRP can be administered as part of a medicament or pharmaceutical preparation. This can involve combining NRP compounds with any pharmaceutically appropriate carrier, adjuvant or excipient. Additionally an NRP compound can be used with other non-NRP neuroprotective, proliferative, or other agent. The selection of the carrier, adjuvant or excipient will of course usually be dependent upon the route of administration to be employed.

The administration route can vary widely. An NRP may be administered in different ways: intraperitoneal, intravenous or intracerebroventricular. The peripheral application may be the way of choice because then there is no direct interference with the central nervous system.

Any peripheral route of administration known in the art can be employed. These can include parenteral routes for example injection into the peripheral circulation, subcutaneous, intraorbital, ophthalmic, intraspinal, intracisternal, topical, infusion (using eg. slow release devices or minipumps such as osmotic pumps or skin patches), implant, aerosol, inhalation, scarification, intraperitoneal, intracapsular, intramuscular, intranasal, oral, buccal, pulmonary, rectal or vaginal. The compositions can be formulated for parenteral administration to humans or other mammals in therapeutically effective amounts (eg. amounts which eliminate or reduce the patient's pathological condition) to provide therapy for the neurological diseases described above.

One route of administration includes subcutaneous injection (e.g., dissolved in 0.9% sodium chloride) and oral administration (e.g., in a capsule).

It will also be appreciated that it may on occasion be desirable to directly administer NRP compounds to the CNS of the patient. This can be achieved by any appropriate direct administration route. Examples include administration by lateral cerebroventricular injection or through a surgically inserted shunt into the lateral cerebroventricle of the brain of the patient.

Determining Doses of NRP

The determination of an effective amount of an NRP to be administered is within the skill of one of ordinary skill in the art, and will be routine to those persons skilled in the art. In certain embodiments, the amount of an NRP to be used can be estimated by in vitro studies using an assay system as described herein. The final amount of an NRP to be administered will be dependent upon the route of administration, upon the NRP used and the nature of the neurological disorder or condition that is to be treated. A suitable dose range may for example, be between about 0.01 mg to about 1 mg per 100 g of body weight, alternatively about 0.06 µg to about 0.6 mg of NRP-1 per 100 g of body weight where the dose is administered centrally.

For inclusion in a medicament, NRP can be directly synthesized by conventional methods such as the stepwise solid phase synthesis method of Merryfield et al., 1963 (J. Am. Chem. Soc. 15:2149-2154). Such methods of peptide synthesis are known in the art, and are described, for example, in Fields and Colowick, 1997, *Solid Phase Pelptide Synthesis* (Methods in Enzymology, vol. 289), Academic Press, San Diego, Calif. Alternatively synthesis can involve the use of commercially available peptide synthesizers such as the Applied Biosystems model 430A.

As a general proposition, the total pharmaceutically effective amount of NRP-1 (SEQ ID NO:2) administered parenterally per dose will be in a range that can be measured by a dose response curve. One range is between about 0.06 mg and about 0.6 mg per 100 g body weight. For example, NRP-1 (SEQ ID NO:2) in the blood can be measured in body fluids of the mammal to be treated to determine dosing. Alternatively, one can administer increasing amounts of the NRP-1 (SEQ ID NO:2) compound to the patient and check the serum levels of the patient for NRP-1 (SEQ ID NO:2). The amount of NRP-1 (SEQ ID NO:2)to be employed can be calculated on a molar basis based on these serum levels of NRP-1 (SEQ ID NO:2).

Specifically, one method for determining appropriate dosing of the compound entails measuring NRP levels in a biological fluid such as a body or blood fluid. Measuring such levels can be done by any means, including RIA and ELISA. After measuring NRP levels, the fluid is contacted with the compound using single or multiple doses. After this contacting step, the NRP levels are re-measured in the fluid. If the fluid NRP levels have fallen by an amount sufficient to produce the desired efficacy for which the molecule is to be administered, then the dose of the molecule can be adjusted to produce maximal efficacy. This method can be carried out in vitro or in vivo. This method can be carried out in vivo, for example, after the fluid is extracted from a mammal and the NRP levels measured, the compound herein is administered to the mammal using single or multiple doses (that is, the contacting step is achieved by administration to a mammal) and then the NRP levels are remeasured from fluid extracted from the mammal.

NRP compounds are suitably administered by a sustained-release system. Suitable examples of sustained-release compositions include semi-permeable polymer matrices in the form of shaped articles, for example, films, or microcapsules. Sustained-release matrices include polylactides (U.S. Pat. No. 3;773,919, EP 58,481), poly(2-hydroxyethyl methacrylate) (Langer et al., 1981), ethylene vinyl acetate (Langer et al., supra), or poly-D-(–)-3-hydroxybutyric acid (EP 133, 988). Sustained-release compositions also include a liposomally associated compound. Liposomes containing the compound are prepared by methods known to those of skill in the art, as exemplified by DE 3,218,121; Hwang et al., 1980; EP 52,322; EP 36,676; EP 88,046; EP 143,949; EP 142,641; Japanese Pat. Appln. 83-118008, U.S. Pat. Nos. 4,485,045 and 4,544,545 and EP 102,324. In some embodiments, liposomes are of the small (from or about 200 to 800 Angstroms) unilamellar type in which the lipid content is greater than about 30 mol. percent cholesterol, the selected proportion being adjusted for the most efficacious therapy. All U.S. parents referred to herein, both supra and infra, are hereby incorporated by reference in their entirety.

PEGylated peptides having a longer life than non-PEGylated peptides can also be employed, based on, for example, the conjugate technology described in WO 95/32003 published Nov. 30, 1995.

For parenteral administration, doses may be between about 0.01 to about 1 mg per 100 g of body weight, alternatively about 0.06 µg to 0.6 mg of NRP compound per 100 g body weight. In some embodiments, the compound can be formulated generally by mixing each at a desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides. It can be appreciated that the above doses are not intended to be limiting. Other doses outside the above ranges can be determined by those with skill in the art.

In some embodiments, formulations can be prepared by contacting a compound uniformly and intimately with liquid carriers or finely divided solid carriers or both. Then, if desired, the product can be shaped into the desired formulation. In some embodiments, the carrier is a parenteral carrier, alternatively, a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

The carrier suitably contains minor amounts of additives such as substances that enhance isotonicity and chemical stability. Such materials are desirably non-toxic to recipients at the dosages and concentrations employed, and include, by way of example only, buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

An NRP compound can be desirably formulated in such vehicles at a pH of from about 4.5 to about 8. It will be understood that use of certain of the foregoing excipients, carriers, or stabilizers will result in the formation of salts of the compound. The final preparation may be a stable liquid or lyophilized solid.

In other embodiments, adjuvants can be used. Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen, or cherry. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a coloring agent, and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

Desirably, an NRP compound to be used for therapeutic administration may be sterile. Sterility can be readily accomplished by filtration through sterile filtration membranes (e.g., membranes having pore size of about 0.2 micron). Therapeutic compositions generally can be placed into a container having a sterile access port, for example an intravenous solution bag or vial having a stopper pierceable by a hypodermic injection needle.

In other embodiments, an NRP compound can be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 0.01% (w/v) aqueous solution of compound, and the resulting mixture is lyophilized. The infusion solution can be prepared by reconstituting lyophilized compounds using bacteriostatic water or other suitable solvent.

Gene Therapy

In other embodiments of this invention, therapeutic methods include gene therapy for treating an organism, using a nucleic acid encoding an NRP compound. Generally, gene therapy can be used to increase (or overexpress) NRP levels in the organism. Examples of nucleotide sequences include SEQ ID NOs: 1, 3, 4, 6, 8, 10, 12, 16, 19, 27 or 35 or portions thereof that encode peptides having the consensus domains and biological properties of NRP. It can be appreciated that other sequences can be used to encode a pro-NRP, which, upon cleavage, can result in a biologically active NRP.

Any suitable approach for transfecting an organism with a sequence encoding an NRP can be used. For example, in vivo and ex vivo methods can be used. For in vivo delivery, a nucleic acid, either alone or in conjunction with a vector, liposome, precipitate etc. can be injected directly into the organism, for example, a human patient, and in some embodiments, at the site where the expression of an NRP compound is desired. For ex vivo treatment, an organism's cells are removed, the nucleic acid is introduced into these cells, and the modified cells are administered to the organism either directly or, for example, encapsulated within porous membranes which are implanted into the patient. See, e.g. U.S. Pat. Nos: 4,892,538 and 5,283,187.

We have demonstrated herein that cultured cells can express NPRs, and that when those NRP-expressing cells are incubated with neurons susceptible to toxic damage, NPRs can be expressed, secreted into the medium and can protect the neurons from toxic damage. This surprising finding supports a therapeutic approach to treating neural degeneration by gene transfer and cell transplantation.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

In certain embodiments, in vivo nucleic acid transfer techniques include transfection with viral vectors (such as adenovirus, Herpes simplex I virus, or adeno-associated virus) and lipid-based systems (useful lipids for lipid-mediated transfer of the gene are N-[1-(2,3-dioleyloxy)propyl]-N,N,N-trimethylammonium (DOTMA), dioleoylphatidylethanolamine (DOPE) and 3-β[N-(N',N'-dimethylamionethane)carbomoyl]cholesterol (DC-Chol), for example. In some situations it may be desirable to provide the nucleic acid source with an agent that directs the nucleic acid-containing vector to target cells. Such "targeting" molecules include antibodies specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake. Examples of such proteins include capsid proteins and fragments thereof tropic for a particular cell type, antibodies for proteins, which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein.

Kits are also contemplated within the scope of this invention. A typical kit can comprise a container, in some embodiments a vial, for the NRP formulation comprising one or more NRP compounds in a pharmaceutically acceptable buffer and instructions, such as a product insert or label, directing the user to utilize the pharmaceutical formulation.

EXAMPLES

The following examples are provided to illustrate certain embodiments of this invention. It can be readily appreciated that other embodiments can be devised and still remain within the scope of this invention. All of these other embodiments are considered to be part of this invention.

Example 1

Identification of Human, Mouse and Rat NRPs

Using bioinformatic tools, we identified NRPs within the human, mouse and rat genome. These new NRP genes were annotated using the following methods.

We performed a BLASTP search using the 16 amino acid rat NRP-1 (SEQ ID NO:2) as a template. We found a sequence having 100% identity to the rat NRP-1 sequence: a human cachexia-related protein. The cDNA of the human cachexia-related protein is encoded by 5 exons located on human chromosome 12. Because of the identity of the rat NRP-1 (SEQ ID NO: 2) and a portion of the human cachexia protein, a new annotation of NRP orthologs was orientated alongside these 5 exons. tBlastN searches within the human NCBI-database revealed a previously unknown open reading frame (ORF) of 321 nucleic acids on chromosome 13. This sequence encodes a peptide having striking homology to the cachexia-related protein fragment having amino acids 1-30 (cachexia protein without signal sequence). These methods were also used to identify other human NRP orthologs, as well as rat and mouse NRP orthologs.

A program for multiple or pairwise alignment of protein or nucleic acid sequences, ClustalW, was used to perform alignment analysis. In order to identify the protein-coding exons of the newly annotated NRP-2 gene on human chromosome 13, (SEQ ID NO:4) the protein encoding nucleotide sequences of the cachexia protein were compared with the region around the ORF of chromosome 13. The non-coding 5' region of cachexia DNA was used to determine exon 1 of the NRP ortholog. For annotating other human and mouse NRPs, alignments of amino acid sequences were performed. By the term annotation, we mean to include processes for identifying DNA sequences containing protein encoding information, splice sites to create new exons, and for predicting the existence and structures, including specific amino acid, peptide or protein domains suitable for identification of NRPs having desirable biological or other properties.

To identify 5' and 3' splice sites in unprocessed RNA, (pre-mRNA), hexamer human consensus sequences for splice sites of the splicosomes were aligned to the respective chromosome 13 NRP sequence (SEQ ID NO: 4) to identify exon-intron boundaries in order to determine the number of exons present in the protein-coding sequence of a newly annotated NRP gene sequence. For identification of mouse splice sites, publications from Baldwin et al. and Wagener et al. were used as templates. For human splice site identification, publications from van der Flier et al. and Guth et al. were used.

Thus, we conclude that multiple NRPs exist in a newly recognized gene family of neural regeneration peptides, having related amino acid domains and having similar biological properties. Members of the NRP gene family include peptides derived from human, rat, mouse and bacterial origin. NRPs of this family can be used to treat a variety of neurological conditions or injury to neural tissue in which neural repair is needed.

Example 2

In Vitro Assay for Evaluating Migration-Inducing Activity I

We developed a new assay system for identifying NRP having migration-inducing activity. The assay system was used following guidelines approved by the Gesundheitsamt Magdeburg animal ethics committee. Newborn Long Evans rats (P0) were killed by decapitation, and neural tissues were used for preparation of organotypic cultures (OTCs). Neocortical tissue (areas 17-18 according to the Paxinos rat atlas of the developing rat brain) and thalamic tissue from the dorsal thalamus (visual areas) were extracted. These areas represent the visual axis. The dorsal thalamus was accessed by an intersection cut to remove the hypothalamus. Subsequently, the thalamus was sliced frontally using a McIllwain tissue chopper into 350 μm thick slices. Using a dissecting microscope, the habenula nucleus served as a landmark to select only dorsal thalamic areas. Cortical tissues were cut using two sagittal and two frontal intersections in order to obtain areas 17-18 of the occipital cortex. Before the last frontal cut was made, the hippocampal formation was removed. The cortical tissues were sliced by a McIllwain tissue chopper into 350 μm thick frontal slices and was incubated in Gey's balanced salt solution (GBSS) plus 0.65% D(+)glucose, and tissuesswere kept at 4° C. for at least 30-40 minutes for recovery.

Figure 1:
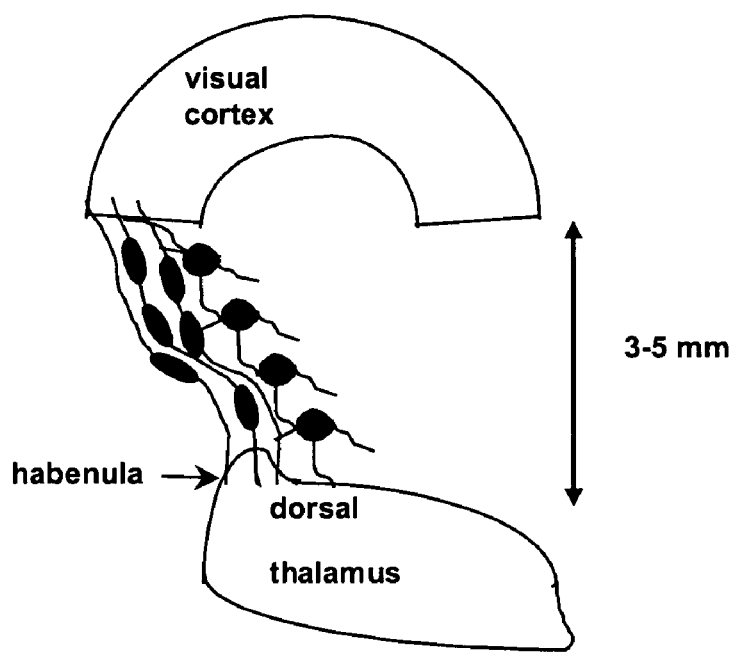
FIG. 1 depicts an arrangement of an in vitro bioassay of this invention, comprising thalamocortical co-cultures on a substrate and the subsequent generation of a thalamic cell bridge after 3-4 days of exposure to purified NRP-1 (SEQ ID NO:2). There was a preference for migration induction within the habenula nucleus a part of the limbic system within the dorsal thalamus.

For each assay, two slices of tissue, one cortical and one thalamic, were arranged at a distance at least about 3 mm from each other on a glass substrate (e.g., a cover slip; FIG. 1). The thalamus was oriented with the habenula nucleus facing cortical layer VI. The tissues were adhered to the substrate using a plasma clot (10 μl chicken plasma (Cocalico) coagulated with 10 μl thrombin (25 U/ml, ICN) and the tissues were subsequently cultured (cultivated) at 36° C. in a roller tube incubator as organotypic cultures using ¾ BME/¼ HBSS (Invitrogen) medium supplemented with 25% heat-inactivated horse serum (Gaehwiler, 1981) plus 2 mM L0glutamine and 0.65% D-glucose. A 712.5 μl sample of prepared medium was supplemented with 37.5 μl of purified rat NRP-1 (SEQ ID NO:2) (in concentrated or diluted form) in 0.01 M sodium phosphate (pH 7.3) or phosphate alone (control). For the experiments using 600 ng/ml NRP-1, the peptide was concentrated 4 times by speed vacuum centrifugation. The medium containing NRP was changed every three days. After each study was completed, the tissues were fixed using conventional fixatives, and migrating neurons were analysed by immunocytochemistry.

Using prior art conditions, in which thalamic and cortical tissues were close together (less than 1.5 mm from each other), the tissues spontaneously produce reciprocal neurite outgrowths and interconnecting cell bridges within 7-10 days after co-culturing commencement (Bolz et al., 1992). The presence of spontaneous regeneration and formation of interconnecting cell bridges confounds attempts to identify exogenously added neuroregeneration molecules, such as NRPs.

We found that if the thalamic and cortical tissues were separated by more than 2 mm, but no spontaneous regeneration features appeared. Thus, any observations of neurite outgrowths or interconnecting cell bridges are due to the influence of factors added to the culture medium. We found that NRPs, including rat NRP-1 (SEQ ID NO:2) and human, mouse and rat orthologous NRPs induced one or more thalamocortical cell bridge(s) over a long distance, for example, about 3-5 mm within a time of only 3 to 4 days of cultivation (see FIG. 1). Thus, in certain embodiments of this invention, NRPs can be identified and/or quantified. In other embodiments, NRPs amounts can be standardized, forming a basis for therapeutic application of NRPs to treat neurological diseases or conditions.

Statistical Analysis

Migration of the thalamic neurons was determined after 3 days of co-culture in the presence of NRP. The migration distances were measured by a micrometer scaled-microscopic ocular, beginning from the tissue margin of the migrating cell stream. See FIG. 4A-4D. As a threshold value for the formation of a migrating cell chain was considered to be a number of at least 5 interconnected neurons. For the determination of the dose-response curve, the longest distance of a migrated neuron from the thalamic tissue margin was measured. Results are given as mean values+/− standard deviation.

Figure 3:
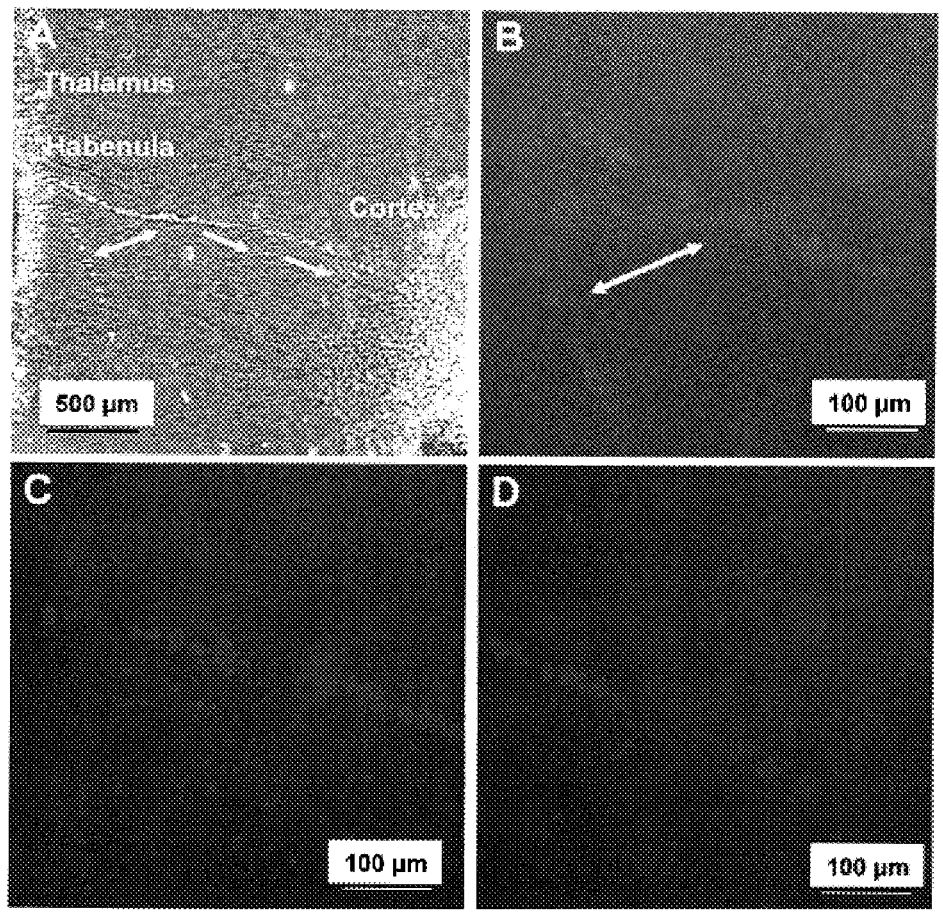
FIG. 3 depicts photomicrographs of formation of neuronal cell bridges between thalamic and cortical tissues within thalamocortical OTCs after 4 days of incubation in vitro. At the commencement of incubation, cultures were supplemented with 300 ng/ml NRP extract (as total protein of the hydroxy apatite chromatography).
Figure 4:
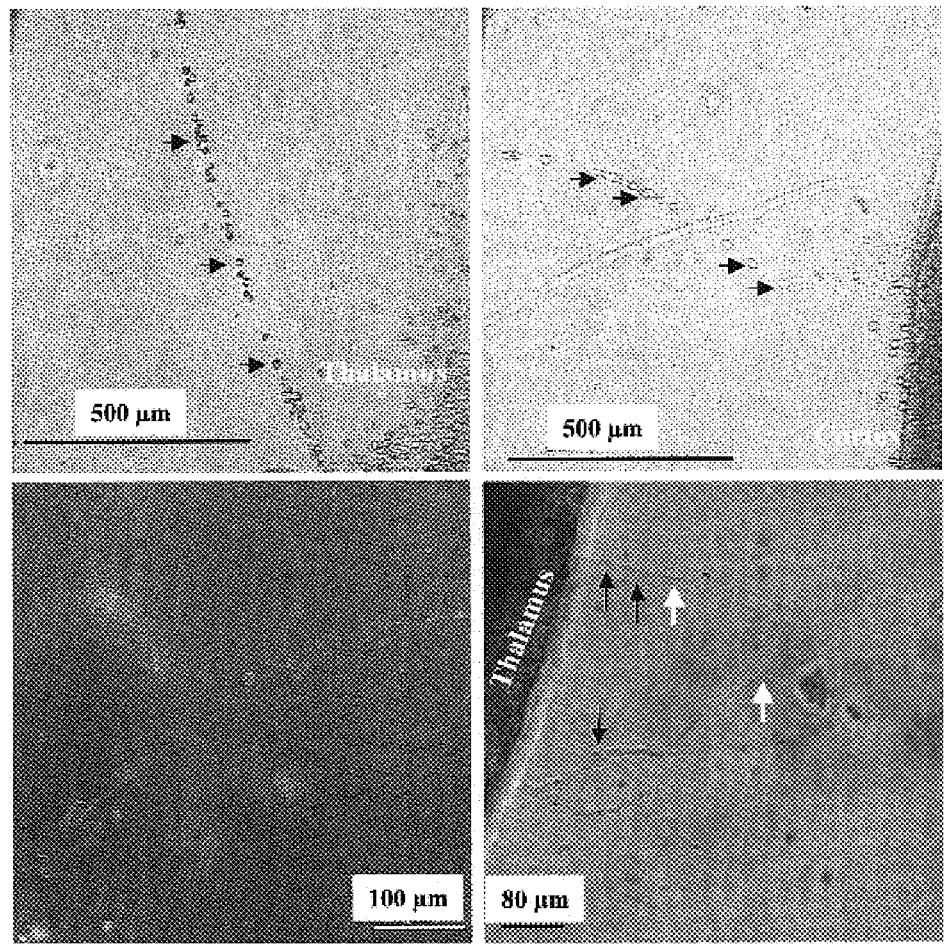
FIG. 4 shows a photomicrograph demonstrating tissue specificity of the originating cell chain within the thalamocortical system. The migrating cell chain, also termed "cell stream" is shown originating from the thalamic tissue (FIG. 4A, upper left panel). The concentration of NRP-1 (SEQ ID NO: 2) producing the greatest effect was 3 nM. Cortical migration chains occurred and are shown in FIG. 4B (upper right panel). Greater magnification revealed that the migrating MAP-2-positive neurons were interconnected by neurite structures (arrow in FIG. 4C, lower left panel).
Figure 5:
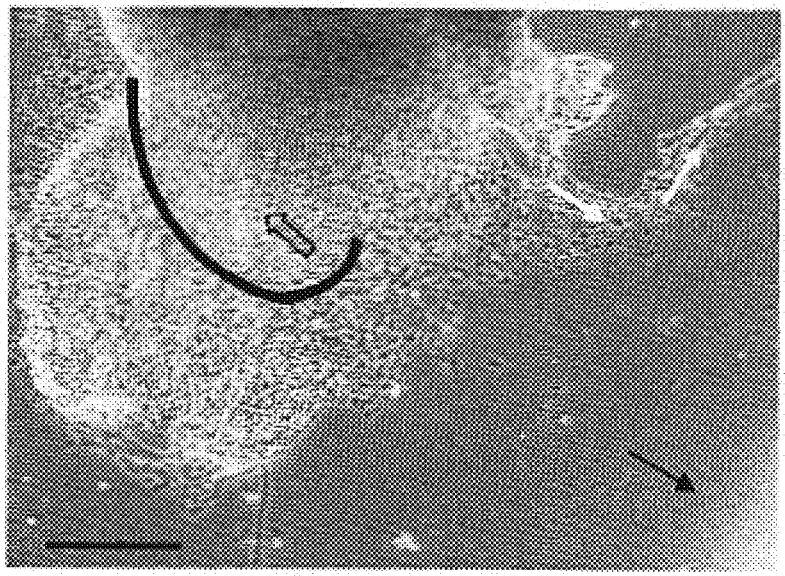
FIG. 5 shows a phase contrast micrograph of the thalamic region of a NRP-1 (SEQ ID NO :2) supplemented OTC (3 nM highly purified cation exchange eluate) 24 hours after the start of incubation. The black line indicates the original margin of the habenula nucleus (open arrow). There was "tissue spreading" of the habenula nucleus. The white arrows indicate a cell chain that was in the migration process. A number of neurites originated from the migrating cell chain and projected to the cortical tissue (black arrow). Bar: 1000 μm.

Induction of Neuronal Cell Chain Migration and/or Neuronal Cell Stream Migration FIG. 3 depicts formation of cell bridges induced by rat NRP-1 harvested from hippocampal OTC supernatant. The NRP-1 was administered to the thalamocortical OTCs at cultivation start. Under these conditions, the formation of cell bridges comprising both proliferating and differentiated neurons occurred. At most NRP concentrations, cell bridges originated from the thalamic tissue (see FIGS. 3A-3D and FIGS. 4A and 4D), and only at a single dose of NRP, a cell bridge originated from cortical tissue as well (FIG. 4B). One possible reason for this observation could be the different anatomy of thalamic and cortical tissue, respectively. Neocortical tissue possesses a basal lamina that can hinder migrating thalamic cells from penetrating into the cortical tissue, whereas the thalamus lacks such a basal lamina. Before neuronal migration occurred, an interconnecting neurite network between the respective tissues was formed within the first 36 hours after cultivation had started in NRP-1 supplemented thalamocortical co-cultures (see FIG. 5). The first migrating cells were observed between 30 and 48 hours after cultivation began (see FIG. 4D).

Figure 6:
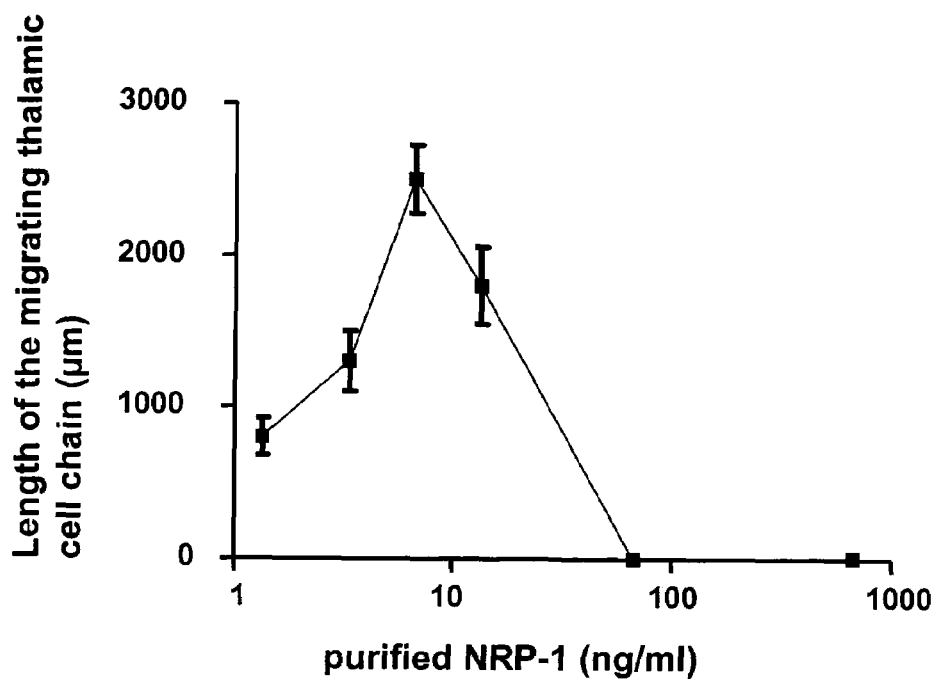
FIG. 6 depicts a graph of a dose-response relationship for NRP-1 (SEQ ID NO: 2) in thalamocortical OTCs. In order to assay the biological activity range of NRP-1 (SEQ ID NO: 2), homogenously purified (cation exchanger) protein was administered to the thalamocortical OTCs at the start of incubation. For the dose-response curve, concentrations of 2, 4, 6, 20, 60 and 600 ng/ml of NRP-1 (SEQ ID NO: 2) were tested. At 2 ng/ml (1 nM), neuronal migration was clearly detected. The concentration producing the longest cell chain was 6 ng/ml (3 nM). At concentrations between about 20-60 ng/ml (10-30 nM), NRP-1 (SEQ ID NO: 2) did not increase neuronal migration. All concentrations were tested 6 times in the assay.

A dose-response curve (FIG. 6) revealed that an applied concentration of 6 ng/ml (3 nM-1/500 diluted 3 µg/ml homogenously purified NRP-1 (SEQ ID NO: 2)) established a cell bridge of 2500±240 µm length between the thalamic and cortical tissues. The concentration range for biological activity range within the in vitro system was between about 1 and 10 nM. The concentration of 3 µg/ml NRP-1 (SEQ ID NO:2) was estimated from the absorbance value of 0.003 measured at the UV wavelength of 280 nm.

We conclude that NRP-1 (SEQ ID NO:2) induced neuronal migration in postnatal explant thalamocortical brain slices. The migrating cell chains overbridged gap regions between thalamic and cortical tissue. We further conclude that NRPs can be used to promote neuronal cell migration. The ability of NRPs to induce neuronal migration indicates an application for NRP-1 (SEQ ID NO:2) in restoring neuronal networks, which degenerate in neurodegenerative diseases and injuries.

Example 3

Migrating Cells are of Neuronal Origin and Can Adopt a Differentiated Phenotype

To determine the cellular nature of cell bridges, we used neural-specific immunohistochemistry. Immunohistochemistry was carried out according to methods of (Obst and Wahle, 1995). OTCs as described above were rinsed twice in 0.1 M phosphate buffer for 3 h. After a study was carried out, tissues were fixed using conventional fixatives suitable for immunohistochemistry. To improve antibody penetration into the tissues and cells, OTCs were incubated for 10 min in a freezing solution consisting of 25% sucrose; 10% glycerol; 100 mM NaCl in 0.01 M phosphate buffer (pH 7.4) at −80° C. (Gulyas et al., 1996). OTCs were then incubated for 5 min in 1% $H_2O_2$ followed by a treatment of 0.4% Triton 100 and 10% normal goat serum (blocking solution) for 3 h (Sigma chemicals). Primary antibodies (anti-parvalbumin IgG; anti-calretinin IgG; anti-MAP-2 IgG) were incubated with 0.4% Triton, 2% BSA and 2% normal goat serum in PBS over night at 4° C. Biotinylated secondary antibody diluted in 0.2% Triton, 2% BSA and 2% normal goat serum in PBS (1/200) was incubated for 2 h, followed by avidin-biotin-horseradish peroxidase complex (Dakopatts, Hamburg, Germany) or alternatively by streptavidin-Cy3 complex (Sigma). For double staining experiments, biotyinylated secondary antibody followed by streptavidin-Cy2 and a goat anti-mouse IgG coupled to Cy2 (1/150) were used. OTCs were rinsed for 3×15 min between incubation steps. Peroxidase reactivity was developed with 0.05% diaminobenzidine (DAB) and 0.009% $H_2O_2$ in 50 mM Tris buffer (pH 7.4) for 10 min. Subsequent treatments included dehydration, clearance, and placing the co-cultures on coverslips with DePeX® (Serva, Heidelberg, Germany) for DAB-treated OTCs, or Fluoromount® (BDH Lab, Poole, England).

Thalamocortical Cell Bridge Was of Neuronal Origin

Figure 7:
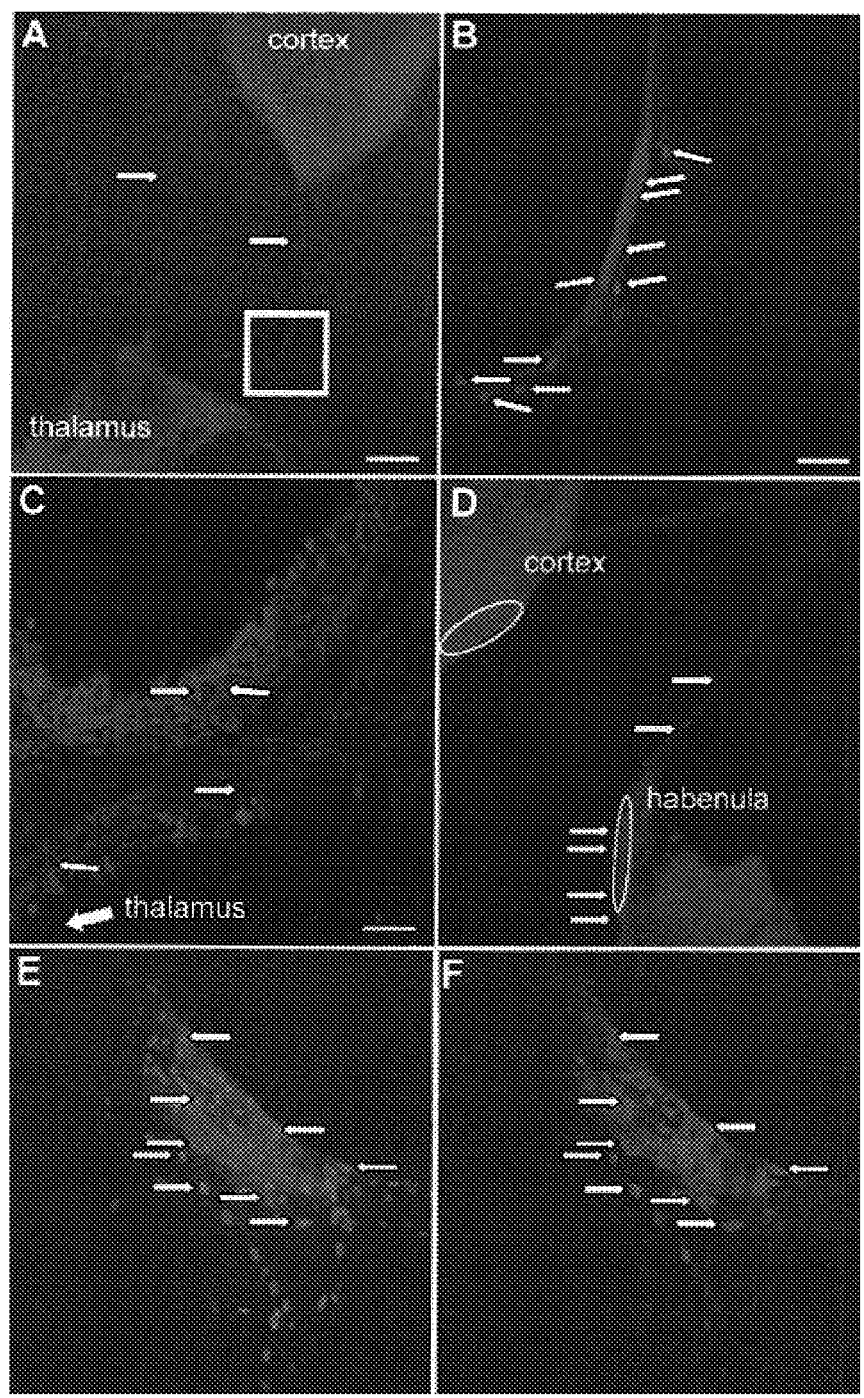
FIG. 7 shows production of a thalamocortical cell bridge after 4 days in vitro. Co-cultures were supplemented with 3 nM highly purified NRP-1 (SEQ ID NO: 2).

Migrating cells within the thalamocortical cell bridge were found to be of neuronal origin. FIG. 7C shows that MAP-2-ir cells formed a highly ordered structure at the thalamic origin. A row of MAP-2-ir neurons formed the margin of the cell stream that was different from the single cell chain migration observed in FIG. 7. The neurons at the margin, projected with their apical dendrite towards the middle of the migrating cell stream accompanied by neurite structures (FIG. 7C). The neurons of the regenerated cell bridge possess high levels of MAP-2 protein. MAP-2 was strongly expressed within the leading apical neurite (FIG. 8) of a migrating neocortical neuron. Within the thalamic migrating cell stream, a subpopulation of MAP-2-ir neurons were co-localized with the calcium binding protein parvalbumin (see FIG. 7A, 7B and FIG. 9). Parvalbumin is a late postnatal marker of neuronal differentiation in the thalamus and can detect inhibitory cells of the thalamic reticular formation as well as excitatory thalamic projection neurons (Sieg et al., 1998). FIGS. 7E and 7F revealed that proliferative cells within the cell bridge are partially co-localized with parvalbumin. This finding indicates that NRP-1 (SEQ ID NO: 2) stimulates early differentiation of parvalbumin-positive neurons in the thalamic cell bridge. Thus, the proliferating cells were of neuronal origin and the NRP stimulated neuronal proliferation and differentiation.

We conclude that the ability of NRP-1 (SEQ ID NO:2) to induce neuronal proliferation, migration and early differentiation indicates many therapeutic applications of NRP compounds in restoring neuronal networks which degenerate in neurodegenerative diseases and injuries. This example also supports the conclusion that the novel assay systems of embodiments of this invention provide sensitive, rapid and selective methods for detecting and quantifying activity of NRP compounds.

Example 4

In Vitro Assay for Evaluating Migration-Inducing Activity II

Figure 2:
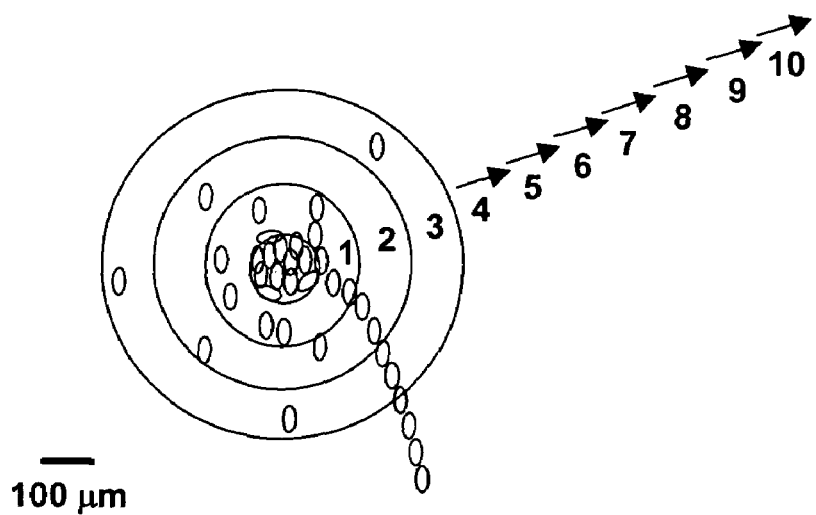
FIG. 2 depicts a schematic diagram of methods used to quantify neuronal migration within cerebellar microexplants. A transparent overlay comprising ten consecutive rings of 100 μm diameter was laid around a microexplant. To calculate the percentage of migrating cells, all cells within a respective consecutive ring were counted and divided by the total number of cells distributed in rings 1 to 10.

Another assay of this invention includes embodiments comprising cerebellar microexplants. Laminated cerebellar cortices of the two hemispheres were explanted from a P-4 Long Evans rat, cut into small pieces in GBSS with 0.65% D(+)glucose solution, and triturated by a 0.4 mm gauge needle and subsequently pressed through a 125 µm pore size sieve. The obtained microexplants were centrifuged (200×g) 2 times for a medium exchange into serum-free BSA-supplemented START V-medium (Biochrom). Finally, the microexplants were reconstituted in 500 µl STARTV-medium. For culturing, 38 µl of the cell suspension and 2 µl of migration-inducing factor (NRP-1) in 0.01 M sodium phosphate (pH 7.3) or phosphate alone (control) was incubated for 3 hours on a poly-D-lysine-coated cover slip in a 35 mm Petri dish under an atmosphere comprising 5% $CO_2$ in air and 100% humidity at 34° C. Subsequently, 1 ml of STARTV-medium was added, and the cultures were evaluated after 2-3 days of culture (for example, see FIG. 2).

For immunohistochemistry and neuronal migration experiments, cerebellar microexplants were fixed after 2-3 days in culture after the following regime: microexplants were fixed by 2-minute, serial treatment with 0.4%; 1.2%; 3% paraformaldehyde/0.25% glutaraldehyde, respectively, followed by a 5 min incubation in 4% paraformaldehyde/0.25% glutaraldehyde in 0.1 M sodium phosphate (pH 7.4). MAP-2 was detected using the biotin-streptavidin/Cy3 detection system as described under the immunohistochemistry section of the thalamocortical OTCs.

Statistical Analysis

Microexplants having a diameter between 100-120 μm were chosen for statistical analysis. For quantitative analysis of neuronal migration, an optical device having 10 consecutive rings of 100 μm diameter was applied over the microexplants. All neurons that had migrated after 48 h of culture were counted. Neurons located between circles 1 to 10 (0.1-1 mm) around the margin of the respective microexplant (see FIG. 2) were counted, and each circle was expressed as a percentage of total migrating cells. The unpaired Student's t-test was used for significance analysis. Results were given as mean values±standard deviation.

Induction of Cerebellar Cell Migration Within a Microexplant System

A concentration of 3 nM of purified NRP-1 (SEQ ID NO:2) was sufficient to induce a significantly enhanced migration of neurons within the cerebellar microexplant system. The number of migrating cells was in the range of 30 and 140 cells measured up to a distance of 1000 um away from the margins of explants having diameters of from 100-120 μm. A highly significant ($p<0.001$) population of 7.3±2.8% of migrating cerebellar cells were distributed between 400-500 μm, and 13.2±13.9% of migrating cerebellar cells were distributed between 500-600 μm away from the microexplant margin after 2 days of culture with NRP-I(SEQ ID NO:2) (see FIGS. 13 and 14). The vehicle-treated (0.01 M sodium phosphate) controls revealed neuronal migration to a certain extent (not significantly better than factor-treated samples over 200 μm migration distance). This relatively minor migration may be because in early postnatal cerebellar tissue, the final migration process to form the cerebellar granule cell layer had not been completed. Therefore the granule cells of P-4 animals revealed some intrinsic neuronal migration activity when cultured. Nevertheless, we found that purified NRP-1 (SEQ ID NO: 2) caused a substantial increase in both the number of migrating cells as well as the distance travelled.

Similar cerebellar granule cell migration has been induced by activation of $AT_2$ receptor of angiotensin II that is highly expressed in early postnatal cerebellar neurons (Cote et al., 1999). After $AT_2$ receptor activation using the highly effective agonist CGP-42112 the longest migration distances were around 550 im measured 96 hours after start of cultivation. The migration-inducing factor confers similar migration distances to the cerebellar microexplants although there exist two major differences to the angiotensin II-induced migration pattern. First, angiotensin does not induce neuronal chain migration like NRP-1 (SEQ ID NO: 2) does and secondly the whole process of neuronal migration is considerably slower when induced by angiotensin II.

Thus, we conclude that NRP-1 (SEQ ID NO:2) induces neuronal migration a separate, novel mechanism, and not by way of angiotensin II receptors. The ability of NRP-1 to induce neuronal migration indicates an application for NRPs in restoring neuronal networks damaged by neurodegenerative diseases and injuries.

Example 5

Induction of Neuronal Proliferation within the Thalamocortical OTCs

Thalamocortical OTCs from rats, as described above in Examples 3 and 4 were incubated at the start of cultivation with 2 μM of BrdU that was removed after 24 hours of cultivation time. OTCs were fixed in 4% paraformaldehyde in 0.1 M phosphate buffer (pH 7.4). Blocking was done in 0.4% Triton and 10% normal goat serum in PBS for 30 minutes. Subsequently the cultures were treated for 30 minutes in 2N HCl at 37° C. and neutralized by 0.1 M $Na_2B_4O_7$ for 2×5 minutes. Internal peroxidase activity was prevented by 5 minute treatment of the OTCs in 1% $H_2O_2$ (only in case of the PAP reaction). Primary antibody (mouse anti-BrdU 1/50-Sigma) reaction was done overnight in 0.4% Triton, 2% BSA in PBS.

Biotinylated goat anti-mouse IgG was applied (1/200 for 2 h) with the subsequent application of the avidin biotin horseradish peroxidase system and the final DAB-detection (0.05%); 0.009% $H_2O_2$ enhanced by 0.025% cobalt chloride and 0.02% nickel ammonium sulphate. BrdU-positive nuclei become black stained. After three PBS washes, the rabbit anti-parvalbumin IgG (1/1000) was applied overnight at room temperature in 0.4% Triton; 2% BSA in PBS followed by the goat anti-rabbit (1/100) in the same buffer. Subsequently, follows the PAP reaction in PBS (rabbit PAP 1/200) developed by the DAB-reaction. The parvalbumin-ir cytoplasm becomes brown stained. OTCs were placed on coverslips with DePeX®. For double fluorescence detection, mouse anti-BrdU IgG and rabbit anti-parvalbumin IgG (or rabbit anti-calretinin 1/1000) were given simultaneously after the neutralisation step and anti-parvalbumin antibody binding was detected by the biotin-streptavidin/Cy2 detection system while the occurrence of BrdU was monitored by an anti-mouse/Cy3 IgG. These fluorescent OTCs were placed on coverslips with Fluoromounto.

Statistical Analysis

For quantitative analysis of the parvalbumin/BrdU co-localization within thalamic tissue, a DAB/PAP reaction system was used, because double-fluorescence techniques can be characterized by quenching effects in dense tissues and thus are well suited for cellular monolayers (see FIG. 9). We counted all parvalbumin-ir cells within 5 factor-treated and 5 control cultures. Subsequently, the double-positive cells (parvalbumin-ir cells that contain a BrdU-positive nucleus) were counted, and results were expressed as a percentage of the total thalamic parvalbumin-ir neuronal cell population. The unpaired Student's t-test was used for significance analysis. Results are given as mean values±standard deviation.

Results

Neuronal expression patterns of newly formed cell bridges were detected using parvalbumin, calretinin, or MAP-2 positive immunological reactions. These studies showed that neuronal cells partly co-localized with BrdU, indicating that these neurons were in the S-phase of the cell cycle. Another subpopulation of cells within the cell bridge exhibited a strong MAP-2, calretinin or parvalbumin expression and was not positive for BrdU (FIG. 9A). Although the mechanism is not known with certainty, one theory is that these cells have completed migration and went off the S-phase to differentiate into their distinct neuronal cell types. We studied the cell cycle status in cultures having BrdU added at the beginning of culturing 4 days after administration of the migration-promoting factor. The number of parvalbumin expressing neurons in the thalamus was between 500 and 700 cells within control and factor treated tissue. Double-staining experiments using anti-parvalbumin antiserum and anti-BrdU antibody revealed that NRP-treated thalamic areas have 6.8±1.3% (p<0.01) of their parvalbumin-ir neurons co-localised with BrdU, whereas controls (medium only) revealed only 2.7±0.7% of parvalbumin-ir neurons in a proliferative state after 5 days in culture (see FIGS. 10 and 11). The control value of 2.7% proliferating parvalbumin expressing neurons represented the basal level of these neurons after the traumatic event of the initial cultivation. Administration of NRP-1 (SEQ ID NO:2) (3 nM) to the thalamocortical OTCs enhanced proliferation of parvalbumin expressing neurons within the thalamic tissue up to 150% compared to controls treated with defined medium alone. A more pronounced proliferation rate was observed within the newly formed (migrated) cell bridge where the majority of parvalbumin expressing neurons were of a proliferative state (FIGS. 7 E and F and FIG. 9).

We also investigated the effects of NRP-1 (SEQ ID NO:2) on the induction of proliferation within astrocytes in a qualitative way. Standard organotypic tissue cultures exhibit increased numbers of reactive astrocytes, which may appear due to the traumatic event of the tissue extraction process. Therefore we looked only at the newly formed cell bridge between the thalamic and cortical tissue 4 days after NRP administration. We found that only a small subpopulation of astrocytes that express GFAP reveal incorporation of BrdU (see FIG. 12).

Purified NRP-1 (SEQ ID NO:2) preferably induces neuronal proliferation but does not induce astroglial division. Thus, we conclude that NRPs are effective agents and can cause neurons to proliferate. The results also indicate applications for NRPs and paralogs or fragments in the treatment of neurological conditions and spinal cord injuries in which neural tissue is damaged or has degenerated, for example Huntington's disease, Parkinson's disease and paraplegia. The results further indicate that NRPs have an application in improving outcomes of neural replacement therapies, such as in transplantation.

Example 6

Effects of Synthetic NRPs on Cerebellar Microexplants

To ensure that the effects observed with purified NRPs originating from tissue cultures were due to the NRPs themselves and not due to contaminants or other materials in the materials, we carried out a series of studies using synthetic NRPs. NRPs were supplied by Auspep (Australia). They were supplied with an amidated C-terminus, and were more than 95% pure as analyzed by MALDI-MS spectrum analysis. The mouse NRP-7 (arachne contig 191157 mouse; SEQ ID NO:17) was 91% pure. The peptides were stored lyophilized at −80° C. under argon until usage. They were reconstituted in PBS, alternatively in 100 µg/ml human transferrin/PBS or in other embodiments in 100 µg/ml BSA/PBS and further diluted in PBS having 10 g/ml of BSA or transferrin before further use within the different assays.

1. Cerebellar Microexplant System for Determination of Survival and Proliferation Inducing Activity of the NRPs Toxicological and drug administration experiments were designed such that 1/100 parts of toxin and neuroprotective drug were administered simultaneously to the freshly prepared cerebellar microexplants derived from P-4 or P8 rats. Glutamate was prepared as a 50 mM stock solution in MilliQ water while 50 mM 3-nitropropionic acid was pH-adjusted (pH 6.8-7.2) in MilliQ water. The concentrations of the oxidative stress inducing toxin, 3-nitropropionic acid (3-NP), and the excitotoxin, glutamate, in the assay were 0.5 mM each. Lyophilized peptides were reconstituted in PBS or 100 µg/ml human transferrin as a 10 µM stock solution. Subsequently, serial dilutions were made. Cerebellar microexplants were cultivated for 48-72 hours at 34° C., 5% $CO_2$ in air and 100% humidity before they were fixed by increasing amounts of paraformaldehyde (0.4%, 1.2%, 3% and 4%—each treatment 2-3 min).

Using the toxins described above, cerebellar explants were exposed for 24 hours, at the beginning of culturing to dilutions of NRP and 0.1 µM BrdU. Subsequently, 80% of the medium was changed without addition of new toxins and NRPs. The cerebellar cultures were fixed as described above after 3 days in vitro. The detection of the incorporated BrdU level was performed as described previously. Under these conditions, over 99% of the cells in the cerebellar population were neurons. Therefore any increase in cell number after NRP administration was most likely due to neuronal cell proliferation.

Neuronal Survival and Proliferation Assays

For statistical analysis of survival, four fields (each field having an area of 0.65 $mm^2$) of each fixed cerebellar culture with the highest cell densities were chosen, and cells displaying neurite outgrowth were counted. Statistical significance was measured by Student's t-test.

For statistical analysis of proliferation four fields (each field having an area of 0.65 $mm^2$) of each fixed cerebellar culture displaying highest density of BrdU-positive nuclei were chosen, and BrdU-positive nuclei were counted. Statistical significance was measured by Student's t-test.

2. Haptotactic Migration Assay

To test the cell adhesion and neuronal migration inducing properties of the NRPs a haptotactic migration cell assay was developed (Lu et al.,2001). For this purpose Transwell® cell culture dishes (Costar) with fitting inserts having pores therein with a 12 µm pore size were used to cultivate striatal and neocortical cells. In general, a test agent was adhered to the surface of a culture dish and an insert having pores was placed in culture medium over but not in contact with the surface of the culture dish. Test cells were placed in the inserts, and any cells migrating through the pores and onto the surface of the culture dish reflected chemattractiveness by the test molecule. Under these conditions, the surface of the culture dish would, over time, release some NRP molecules into the culture medium. It can be appreciated that the concentration of "free" NRP would be greater nearer the surface of the culture dish than at distances farther away from the culture dish, thereby creating a gradient in NRP concentration. Cells exposed to the gradient of NRP concentration could then be stimulated to migrate through the pores in the insert and then down onto the NPR-coated surface. By counting the number and morphology of such migrant cells, effects of NRPs on neuronal migration and differentiation can be evaluated.

After the inserts were coated with an NRP (or control), the inserts were coated with poly-D-lysine ("PDL") (0.1 mg/ml in PBS—cell culture tested grade from Sigma) for 15 minutes at room temperature. A 19 mer form of an NRP (NRP-2 segment KS; KDPEARRAPGSLHPCLAAS-$NH_2$; SEQ ID NO:23) of the annotated human NRP encoded by a nucleotide sequence located on chromosome 13 (SEQ ID NO:4), a 24 mer form of NRP-7 (SEQ ID NO:17 or it alternative, SEQ ID NO:36), NRP-7 segment SW, (SEPEARRAPGRKGGV-VCASLAADW-NH$_2$: SEQ ID NO:24) of the annotated mouse arachne contig__191157 gene NRP ortholog (SEQ ID NO:16) were chosen. The lyophilised peptides were reconstituted in 100 µg/ml human transferrin or bovine serum albumin (BSA) in PBS and further NRP dilutions were made in the presence of 10 µg/ml of the respective proteins. Peptide concentrations of between 0.01-1 µg/ml were used as well as blank transferrin and BSA controls. The final amounts of the NRPs were between 15 and 1500 ng/110 mm$^2$. The peptide coating process was carried out for 2 hrs at 37° C. After a PBS wash the culture dishes were subsequently coated with PDL (0.1 mg/ml) for 2 hrs at 37° C. followed by a PBS wash.

For seeding striatal cells, 1.5 ml of Neurobasal/B27 medium was put into the culture dishes and 0.5 ml of Neurobasa VB27 medium was put into the insert. The assay was ready for cell seeding. For the seeding of cortical cells, 50% of Neurobasal/B27 medium and 50% of astrocyte conditioned medium were added to culture dishes and inserts before the seeding of the cells.

Preparation of Striatal Tissues

For the preparation of striatal tissue from rat E18/E19 embryos, the dam was sacrificed by CO$_2$-treatment in a chamber for up to 4 minutes, and was then prepared for caesarean section. After surgery the embryos were removed from their amniotic sacs, decapitated and the heads were put on ice in DMEM/F12 medium for striatum and PBS plus 0.65% D(+)-glucose for cortex preparation. The whole brain was removed from the skull with the ventral side facing upwards in DMEM/F12 (Invitrogen) medium. The striatum was extracted under a stereoscopic microscope, by dissecting out the striatum from both hemispheres, which was then placed into the Falcon tube on ice.

The striatal dissection for both hemispheres was performed as follows; the embryonic brain was placed ventral side down, rostral end forward. Along the midline one hemisphere was gently pulled open using fine forceps. A frontal rostral cut was performed to expose the inner region (the striatum) that was located rostral-centre within the cortical cavity. The striatum was pinched out using the forceps and taking care not to avoid the underlying cortex. Tissue pieces were placed into a Falcon tube on ice. The collected striatal tissue was triturated using a P1000 pipettor in 1ml of medium. The cells were triturate by gently pipetting the solution up and down into the pipette tip about 15 times, using shearing force on alternate outflows. The tissue pieces settled to the bottom of the Falcon tube within 30 seconds, and subsequently the supernatant was transferred to a new sterile Falcon tube on ice. The supernatant contained a suspension of dispersed, dissociated cells. The tissue pieces were exposed to a second round of trituration by adding 1 ml of ice-cold DMEM/F12 medium to the tissue pieces in the first tube and triturating as before. In so doing, we did not excessively damage cells already dissociated. The tissues pieces were allowed settle and the supernatant removed to a new sterile Falcon tube on ice. The cells were centrifuged at 250 g for 5 minutes at 4° C. The resuspended cell pellet was used for cell counting.

Preparation of Cortical Astrocyte Cultures

One cortical hemisphere was used from P1 rats and collected into 4 ml of DMEM. Trituration was done with a 5 ml glass pipette and subsequently through an 18-gauge needle. Afterwards, the cells were passed through a 100 µm cell strainer and then washed in 50 ml DMEM, followed by centrifugation for 5 min at 250 g. The sediment was resuspended into 20 ml DMEM+10% fetal calf serum. 10 ml each were added into two 25 cm$^2$ flasks. They were cultivated at 37° C. and 10% CO$_2$ with a medium change twice weekly. After cells reached confluence they were washed three times with PBS and adjusted to Neurobasal/B27 and incubated for another 3 days. The supernatant was frozen at −80° C. for transient storage until use.

The cortical tissue was extracted from E18/19 rat embryos. The two cortical hemispheres were carefully removed by a spatula from the whole brain with the ventral side facing upwards into a PBS+0.65% D(+)-glucose containing petri dish. Forceps were put into the rostral part (near B. olfactorius) of the cortex for fixing the tissue and two lateral—sagittal oriented cuttings were done to remove the paraform and entorhinal cortices. The next cut involved a frontal oriented cut at the posterior end to remove the hippocampal formation. A fmal frontal cut was done a few millimeters away from the last cut in order to get hold of area 17/18 of the visual cortex.

The collected cortices were placed on ice in PBS+0.65% D(+)-glucose and centrifuged at 350 g for 5 min. The supernatant was removed and trypsin/EDTA (0.05%/0.53 mM) was added for 8 min at 37° C. The reaction was stopped by adding an equal volume of DMEM+10% fetal calf serum. The supernatant was removed by centrifugation followed by two subsequent washes in Neurobasal/B27 medium. Cells were triturated once with a glass Pasteur pipette in 1 ml of Neurobasal/B27 medium and subsequently twice more using a 1 ml syringe having a 22-gauge needle. The cell suspension was passed through a 100 im cell strainer and subsequently rinsed in 1 ml of Neurobasal/B27 medium. Cells were counted and were ready for plating for the haptotactic migration assay.

Cell Culture Conditions for the Haptotactic Migration Assay 200,000 striatal or cortical cells in a volume of about 50 µl of volume were seeded into an insert and the whole assay of inserts was cultured at 37° C. in an atmosphere containing 5% CO$_2$ in air and having 100% humidity. After 24 to 48 hrs, cells were fixed as already mentioned with increasing amounts of paraformaldehyde as described above.

Statistical Analysis

All paraformaldehyde-fixed cells displaying neurite outgrowth, which had migrated at least 1 mm (located at the bottom of the culture dish), were counted 48 hrs after the start of cultivation. Student's t-test was performed to obtain significance values.

Neuronal Cell Proliferation Inducing Activity and Neuronal Survival Activity And Neuronal Migration Inducing Activity For the testing of the biological activities of the human NRP-2 located on chromosome 13 (SEQ ID NO:5), NRP-2 segment KG (SEQ ID NO:18) and NRP-2 segment KS (SEQ ID NO:23) of the peptide were used. NRP-2KG (SEQ ID NO:18) is located between amino acids 20-43 of the annotated NRP amino acid sequence (SEQ ID NO:5), and produces the peptide: KDPEARRAPGSLHPCLAASCSAAG-NH$_2$ (NRP-2KG; SEQ ID NO:18), and the 19 mer form (NRP-2KS: SEQ ID NO:23) is located between amino acid positions 20-38 in SEQ ID NO:5. Preconditioning of cerebellar cultures with human NRP-2KG (FIG. 15) at a concentration between 5 to 100 nM for 15 hours resulted in complete neuroprotection from oxidative/excitotoxic injury. The data also showed that over a wide dose range, between 1-200nM, NRP-2KG showed no cytotoxicity. At a concentration of 1 nM, NRP-2KG (SEQ ID NO:18) showed 42.4% recovery from 3-NP/glutamate injury, which was similar to the 46.0% recovery rate seen at 1 nM concentration in the injury, and human NRP-2KG (SEQ ID NO:18) (compare FIGS. 15 and 16). The effective dosage range of NRP-2KG (SEQ ID NO:18) was even bigger in injured cells, namely between 0.1 pM and 1 nM. In comparison, in uninjured cells the dosage range had biological effects between 5 nM and 100 nM.

Within the applied proliferation assay rat NRP-1 (SEQ ID NO:2) and NRP-2KS (SEQ ID NO:23) were tested for neuronal proliferation inducing activity (see FIG. 19). In order to discriminate proliferation from increased survival and cellular adhesion properties, NRP-2 KS (SEQ ID NO:23) was administered 24 hrs after the start of cultivation. Rat NRP-1 (SEQ ID NO:2) had specific effects on neuronal proliferation, (see FIGS. 7, 9 and 10). Neuronal proliferation induced by NRP-2KS (SEQ ID NO:23) occurred within a range of about 0.3-30 nM using un-injured cerebellar microexplants (verified by counting cells displaying neurite outgrowth). The highest activity was observed at a concentration of 300 µM, which produced increased neuronal cell proliferation, or 117.5% greater than vehicle-treated controls. Rat NRP-1 (SEQ ID NO:2) had its greatest effect at 3 nM with 81.2% up regulation of neuronal cell proliferation (see FIG. 17).

For assaying chemoattractive activity of neuronal migration inducing factors a haptotactic migration assay (Lu et al., 2001) was applied. The human NRP-2KG was coated on Transwell® culture dishes in the presence of BSA or transferrin followed by PDL-coating. Seeded embryonic striatal cells migrated from the culture dish insert over a distance of 1 mm to the bottom of the culture dish. If the NRP-2KG (SEQ ID NO:18) was reconstituted in BSA, the migration inducing activity was non-significant, whereas NRP-2KG (SEQ ID NO:18) reconstituted in human transferrin and subsequent immobilization of 150 ng NRP-2KG (SEQ ID NO:18) caused 466.0% more neurons to migrate to the culture dish bottom after 2 days in vitro compared to transferrin control alone (see FIG. 18).

Biological activity of the human NRP located on chromosome 3 (SEQ ID NO:6) was tested using a 1 lmer peptide (NRP-3 segment SQ; SDSFKSQARGQ-NH$_2$: SEQ ID NO:25), which is located between amino acids 13-23 of the annotated NRP protein encoding sequence (SEQ ID NO:7). NRP-3 segment SQ (SEQ ID NO:25) elicited maximal biological activity between 100 µM and 1 nM applied within the cerebellar microexplant neurotoxicity assay (see FIG. 21). After 48 hrs, 100 µM of NRP-3 SQ (SEQ ID NO:25) increased recovery from oxidative/excitotoxic injury by 27.7%.

Biological activities of the human NRP located on chromosome 15 (NRP-4; SEQ ID NO:8) were tested using a 11 mer form of the peptide (NRP-4 segment GQ: GTPGRAE-AGGQ-NH$_2$: SEQ ID NO:26), located between amino acids 22-32 of the annotated NRP-4 protein encoding sequence. For neuronal survival, NRP-4 segment GQ (SEQ ID NO:26) conferred maximal biological activity between 10-100 nM as measured in the cerebellar microexplant neurotoxicity assay. After 48 hrs, 100 nM NRP-4 segment GQ (SEQ ID NO:26) produced recovery from oxidative/excitotoxic injury by an average of 46.3% (see FIG. 19).

NRP-4 segment GQ (SEQ ID NO:26) was also tested for neuronal proliferation inducing activity. Neuronal proliferation inducing activity of NRP-4 segment GQ (SEQ ID NO:26) was observed at a concentration of 10 nM, and produced an up regulation of 132.2% in the proliferation rate compared to injured cerebellar microexplants (see FIG. 20). There was no difference between injured and non-injured (vehicle treatment) microexplants concerning the proliferation rate, which indicated that the 24 hr injury protocol did not produce reactive astrocytes.

Biological activities of NRP-9 (SEQ ID NO:28), the rat orthologues of the mouse NRP-7 (SEQ ID NO: 17), were tested using its 21 mer form (NRP-9 segment SD (SEPEAR-RAQGGQIPSERVLSD-NH$_2$; SEQ ID NO:34)), which is located between amino acid residues 88-108 of the annotated NRP-9 (SEQ ID NO: 28). The neuronal survival activity conferred was maximal between 0.1-10 pM NRP applied within the cerebellar microexplant neurotoxicity assay (FIG. 23B).

Biological activities of the arachne_contig 191157 mouse NRP-7 (SEQ ID NO:17) were tested using a 24 mer NRP form of this peptide (NRP-7 segment SW; SEQ ID NO:24), which is located between amino acid residues 62-85 of the annotated NRP protein encoding sequence (from SEQ ID NO:17). The neuronal survival activity conferred was maximal between concentrations of about 0.1 and about 10 pM NRP-7 SW (SEQ ID NO:24) (FIG. 23). Cells treated with NRP-7 segment SW (SEQ ID NO:24; 48 hrs; 1 pM) reconstituted in human transferrin exhibited 57.0% recovery from oxidative/excitotoxic injury (see FIG. 22). Without reconstitution in human transferrin, the NRP-7 segment SW (SEQ ID NO:24) displayed less survival-promoting activity. The maximal activity range was then between 100 pM and 1 nM displaying 44.8% recovery from oxidative/excitotoxic injury at 100 pM mouse NRP (see FIG. 25).

The NRP-7 segment SW (SEQ ID NO:24) was tested for neuronal proliferation inducing activity. Neuronal proliferation inducing activity for the mouse NRP-7 segment SW (SEQ ID NO:24) could be seen at 0.1 pM and 100 pM of mouse NRP with an up regulation of averages of 252.6% and 123.7%, respectively, of the proliferation rate observed for injured cerebellar microexplants (see FIG. 24). There was no difference between injured and non-injured (vehicle treatment) microexplants concerning the proliferation rate.

NRP-7 segment SW (SEQ ID NO:24) was tested for chemoattractive activity using a haptotactic migration assay. NRP-7 segment SW (SEQ ID NO:24) was coated on Transwell® culture dishes in the presence of BSA followed by PDL-coating. Subsequently mouse NRP was given at 1 pg/ml directly into the medium. Seeded embryonic cortical cells migrated from the culture dish insert over a distance of Imm to the bottom of the culture dish. If mouse NRP was reconstituted in BSA followed by subsequent immobilization of 15 ng of the 24 mer mouse NRP, 49.8% more neurons migrated to the culture dish bottom after 1 day in vitro compared to BSA control alone (see FIG. 25).

We conclude that NRP-1 (SEQ ID NO:2) derived from hippocampal OTC supernatant with a molecular mass of 2046 induced neuronal proliferation and neuronal migration in the differentiated cultivated postnatal thalamus. Furthermore, NRP-1 induced neocortical neuronal migration by passing the barrier of the cortical basal lamina. The activity of NRP-1 was not tissue specific since cerebellar cells demonstrate strongly enhanced migratory behaviour in response to NRP-1 administration.

The results indicate an application for NRP-1 (SEQ ID NO:2) in inducing the proliferation and migration of neurons particularly in neurodegenerative diseases in which discrete areas degenerate and so a replenishment of new neurons is desired, eg. dopaminergic neuronal loss in the substantia nigra in Parkinson's disease, the cholinergic neuronal loss in the basal forebrain in Alzheimer's disease and GABA-ergic neuronal loss in the caudate nucleus and striatum in Huntington's disease.

The disclosed rat, human and mouse NRPs (SEQ ID NOS: 2, 5, 7, 9, 11, 13, 17, 18, 20, 23, 24, 25, 26, 28, 29, 30, 31, 32, 33, 34, 36, 43, 44, 45, 46, 47 and 49) (and fragments thereof containing the domains related to function) and other NRPs disclosed herein can possess similar activities. These peptides can promote neuronal proliferation, neural migration, neurite outgrowth, neuronal differentiation and neuronal survival.

The results further indicate that NRP compounds can be useful in situations in which neural repair is desirable. Such situations include diseases and injuries where neurons are damaged or have degenerated. Certain neurological diseases such as Alzheimer's disease, Parkinson's disease, Huntington's disease and others can be treated using the peptides of embodiments of this invention. Moreover, any type of neural damage, such as spinal cord or other central nervous system injuries can be treated using NRPs of this invention. Such injuries can be caused by trauma (blunt force or penetrating), hypoxia, such as caused by stroke, infarction, hypotension, or high altitude exposure.

The new assay systems described herein, although carried out using rat brain tissues, are an effective method for detecting and measuring activities of NRPs from any source, including human and murine sources. Because human and rodent NRPs share common peptide domains, embodiments of these assays is predictive of effects of NRPs in humans as well as other species that share at least one of characteristic peptide domains identified herein.

Example 7

Purification of Rat NRP-1 From Hippocampal OTC Supernatant

Rat NRP-1 was purified from hippocampal OTCs. Sagittally cut slices 350 μm thick from the hippocampal formation of P0 Long Evans rats were prepared in oxygenated, protein-free minimal essential medium "MEM" followed by a 30 min recovery period at 4° C. Subsequently, the slices were put on 0.4 μm interface membranes and were cultured in protein-free MEM under an atmosphere of 1% $CO_2$ in air as an air-liquid interface culture according to methods described by Stoppini (Stoppini et al., 1991) for 7 to 14 days. Every three days, the cell culture supernatant was harvested and stored at −20° C. until usage.

Rat NRP-1 was purified from samples of 100 ml protein-free (BME-medium+HBSS) medium obtained after culture of cultivated hippocampal OTCs for from about 5 to 14 days (DIV). Supernatant from the samples was dialysed against 200 volumes of binding buffer (0.05 M potassium phosphate—pH 7). (See flowchart FIG. 26).

Chromatography was carried out at a flow rate of about 1 ml/min of the dialysed supernatant on a 5 ml column of HiTrap Blue Sepharose (Amersham/Pharmacia). Elution was done by a stepwise gradient using KCl, until a final concentration of 1.5 M KCl in binding buffer was used.

Subsequently, the eluted material from the Blue Sepharose column was subjected to dialysis against hydroxy apatite binding buffer (0.01 M sodium phosphate—pH 7). Subsequent chromatography (1 ml/min) was on a 1 ml hydroxy apatite column (BioRad). Elution was done by a stepwise gradient until a concentration of 0.4 M sodium phosphate (pH 6.8) was used.

The resulting eluate was dialysed against 0.01 M sodium phosphate (pH 7) and subsequently was precipitated by 80% (v/v) acetone at −20 ° C. for 3 hours. Centrifuged precipitate was reconstituted in 200 μl of 0.2 M NaCl, 0.05% (v/v) Tween 80, 0.02 M of sodium phosphate (pH 7).

Gel filtration was carried out at a flow rate of 3.4 cm/h on Macroprep-40/1000 obtained from Biorad. The column dimension was 50×1.5 cm. Eluate with migration-inducing activity eluted at molecular weights of between 50,000-10,000.

Samples were then dialysed against 0.01 M sodium citrate (pH 4) and chromatography at a flow rate of (1 ml/min) on a 1 ml Econo-Pac S (Biorad) column was performed. Elution was done by a steep gradient of 1 M NaCl in binding buffer (pH 4.5). NRP-1 (SEQ ID NO:2) eluted between 0.5-0.6 M NaCl with an absorption maximum of 0.04 measured at 254 nm (see FIG. 27).

NRP-1 (SEQ ID NO:2) was homogenously purified after cation exchange chromatography as revealed by MALDI-TOF MS analysis (see FIG. 28). The mass spectrum revealed a main peak/abundance at a mass of 2046. The first 16 N-terminal amino acids have been sequenced, and resulted in unambiguous identification of those amino acids, indicating that the NRP-1 (SEQ ID NO:2) was substantially free of protein or peptide contaminants. Purified protein was stored lyophilised at −80° C.

The obtained sequence revealed identity to a recently described survival-promoting peptide that consists of 30 amino acids (Cunningham et al., 1998) and the human cachexia protein (US patent 5834192). Molecular mass calculation beginning from the sequenced C-terminus of the 16-residue NRP-1 (SEQ ID NO:2) compared to the ongoing sequence of the survival-promoting peptide and the human cachexia protein excluded the possibility that NRP-1 (SEQ ID NO:2) is a simple degradation product of the cachexia protein or survival-promoting peptide, respectively.

NRP-1 (SEQ ID NO:2) can be isolated and purified sufficiently to permit therapeutic use. Because NRP-1 can be purified, it can be administered to treat a neurological condition or nervous system injury in which neural repair is needed.

Example 8

NRP Gene Identification II

To identify mammalian neuronal migration-inducing factors with efficacy on neuronal survival, proliferation and neuronal differentiation, we under took a screen of the rat and mouse genome using the human cachexia related protein cDNA and its encoded 16-mer cachexia fragment as a template to identify novel NRP homologues.

Identification of the NRP genes involved obtaining total RNA from different cell sources (in vivo tissue, neural stem cell cultures). RNA was extracted using the Roche Total RNA Isolation Kit. Complementary DNA (cDNA) was synthesised using Superscript RT II, followed by multiplex PCR amplification of the mouse NRP gene fragment and beta-actin using the following primers: mouFS NRP Fwd primer: 5' AACGGAATGAATCGAAACCC 3' (SEQ ID NO:37); mouFS NRP Rev primer: 5' CGCTCGACATTACAGCTCA 3' (SEQ ID NO:38); mouse beta-actin Fwd: 5' GAAAGGGT-GTAAAACGCAGC 3' (SEQ ID NO:39); Mouse B-actin Rev: 5' GGTACCACCATGTACCCAGG 3' (SEQ ID NO:40). The correct sized fragments were gel purified, cloned directly into pGEM vectors and transformed into competent strain of E. Coli (DH5α). The transformed cell colonies were screened for the presence of the NRP gene fragment, and the plasmids from positive colonies were sequenced The structure of the gene encoding the NRP gene is depicted in FIG. 29A).

Characterisation of NRP Protein Domains

NRP is probably secreted over the non-classical pathway like FGF-1, FGF-2 because of highly significant scores when interpreting the protein sequence using the SecretomeP server (Technical University of Denmark). The high number of positive amino acid residues and overall atom number within N-terminal NRP led to this prediction (Bendtsen et al., 2004).

A single trefoil domain sequence motif can be predicted within the mouse NRP sequence and this domain has 52.5% homology (FIG. 29D) to human pS2 protein (Jakowlew et al., 1984). The putative NRP trefoil domain has 9 of 15 conserved amino acids within the consensus sequence of the trefoil domain (database SMART) as similar or identical. This 60% consensus value is also the threshold value for the acceptance of NRP as a trefoil factor family member. Trefoil domains have been implicated to participate in protein-protein interactions and acting through cyclooxygenase2 (COX-2) and thromboxane A2 receptor (TXA2-R) activation pathways (Rodrigues et al., 2003). The human Ps2 protein belongs to trefoil factor family 1 (TFF-1) and has been implicated in chemoattraction of breast cancer cells (Prest et al., 2002) by signalling over the ERK1/2 pathway (Graness et al., 2002).

The neuronal survival, proliferation, migration and differentiation-promoting mouse NRP (NRP-7 segment SW) domain is located C-terminal from the trefoil domain and is located at the C-terminus for rat NRP-9 (see aligned 21 mer and 24 mer sequences in FIG. 29B).

Homology Between NRP, Cachexia-Related Protein and SDF-1

In spite of the existence of striking similar biological activities between NRPs and SDF-1α both peptides reveal only a moderate similarity of 32.6% homology (FIG. 29E).

It has been shown that the first 9 amino acids of mature SDF-1 display residual chemoattractive activity, approximately a factor 100 lower than SDF-1α (Loetscher et al., 1998). The N-terminal 11 amino acids of the mouse 24 mer peptide (NRP-7 Segment SW; SEQ ID NO:24) align with more than 50% homology to the start of mature SDF-1. The related protein domains indicate that the cachexia protein, NRPs and SDF-1α share biological active domains that are important for neuronal survival, proliferation, migration and differentiation. For the cachexia-related protein and SDF-1 the biological active regions are situated N-terminal of the mature proteins while for the NRP this region is located C-terminal from the trefoil domain.

Example 9

Cerebellar Microexplants II: Neuroprotection and Neuronal

Proliferation

Methods

Laminated cerebellar cortex was extracted from P3/4, P7/8 rat pups and triturated through gauze having a 125 μm pore size to obtain uniformly sized microexplants. After centrifugation for 3 minutes at 61 g and the pellet was resuspended in StartV medium (Biochrom) and the suspension seeded on poly-D-lysine coated coverslips in 6-well plates and incubated for 3 hrs to allow adherence, before 1 ml StartV per well was added. As described previously, glutamate/3-NP and NRP were also added. The explants are cultivated at 34° C. at 5% $CO_2$ and 100% humidity for 48-72 hrs. BrdU was administered at start of cultivation for proliferation rate measurements and cells are counted per microscopic field after 48-72 hrs.

Results (a) Neuroprotection

Nanomolar concentrations of NRP-4 segment GQ (SEQ ID NO: 26), conferred survival rates of 50% after severe injury (FIG. 30).

(b) Neuronal Proliferation

NRP-7 segment SW (SEQ ID NO: 24) enhanced the proliferation rate in these cultures by more than 200% (FIG. 31). Proliferative cells of cerebellar microexplants were not susceptible towards excitotoxic and oxidative stress compared to effects of vehicle alone.

Example 10

Haptotactic Migration Assays

NRPs were tested for migration-inducing/chemoattractive activity on mouse neural stem cells, EGF-dependent immortalized mouse neural stem cell line MEB5 and wild-type PC-12 cells in a haptotactic migration assay as described below.

Methods

Initial NRP Coating. Control wells of Transwell plates (Coming) with 12 μm pore size were coated in 1.5 ml of the BSA/PBS vehicle. Remaining plates were coated using various concentrations of NRPs ranging between 1-100 ng/ml (prepared in PBS containing 10 ug/ml BSA). The plates were then incubated at 37° C. for 1 hr to coat. Wells were then rinsed 2× with 1 ml sterile PBS.

Extracellular Matrix Coating:

Laminin (10 g/ml) for MEB-5 cells, PDL (50 μg/ml)+Matrigel for mouse primary stem cells and fibronectin (25 ug/ml)+matrigel for PC-12 cells were used as extracellular matrix (ECM) coating for the cells. All ECM compounds were diluted in PBS. 1.5 ml of the ECM per well was incubated for 2 hrs at room temperature. The wells were then rinsed once with Iml serum-free media (e.g. NB/B27) followed by 1 ml PBS wash.

Coating of Inserts:

A 5 ug/mL PDL/PLL mixture (in PBS) was used to coat inserts. Subsequently the inserts were rinsed with MilliQ water.

Transferring to Media and Cell Seeding: Appropriate medium (MEB-5 cells: DMEM-high glucose+N2 (growth medium supplement from Invitrogen)+10 ng/biotin+2 mM L-glutamine, primary stem cells: NSA-medium from Euroclone and for PC-12 cells: NB/B27 medium) was transferred into the 12-well plates. The plates were then incubated at 37° C; 5% $CO_2$ and seeded with $1-2\times10^5$ cells. Plates were fixed at 1-2 days in vitro (DIV).

Fixation: Inserts were discarded and wells fixed in successive dilutions of PFA (0.4, 1.2, 3 and 4%) for 3-5min in each dilution. The wells were rinsed and stored in successive dilutions of PFA (0.4, 1.2, 3 and 4%) 3-5 min in each dilution. The wells were rinsed and stored in PBS until counting. All cells that displayed neurite outgrowth and traveled to the bottom chamber were counted as migrating cells.

Results 10 ng/ml NRP-4 GG (SEQ ID NO:29) caused 195% more MEB-5 cells to migrate to the bottom of the culture dish in comparison with the BSA-vehicle alone (FIG. 32A). In the presence of NRP-4 GG (SEQ ID NO:29) peptide 93.7% more E14 cells migrated compared with the BSA-vehicle alone (FIG. 32B). 109% more MEB-5 cells migrated to the bottom in the presence of NRP-2 KS (SEQ ID NO:23) compared with the BSA-vehicle alone (FIG. 32C). 35% more E-14 cell density occurred in the presence of NRP-7 SW (SEQ ID NO:24)-treated wells compared with the BSA-vehicle (FIG. 32D). 80.8% more PC-12 cells migrated to the bottom in the presence of NRP-4 GG (SEQ ID NO:29) peptide compared with the BSA vehicle alone (FIG. 32E). NRP-7 SW (SEQ ID NO:24) caused 333% more PC-12 cells to migrate in compared with the BSA vehicle alone (FIG. 32F).

Example 11

Neural Stem Cell Culture and Differentiation Assay for Axonal

Outgrowth

NSA stem cell culture medium was purchased from Euroclone, Italy. Neurobasal medium, DMEM/F12 medium, N2 and B27 supplement were all from Life Technology. Anti-βIII-tubulin antibody was purchased from Sigma. The Cy3-conjugated goat-anti mouse antibody was purchased from Amersham and Syto21 from Molecular Probes. NRP-2KS (SEQ ID NO:23) and NRP-7 SW (SEQ ID NO:24) were used. Human recombinant Erythropoietin (EPO) was purchased from R&D Systems.

Neural Stem Cell Culture

Neural stem cells were derived from E15 C3H mice forebrain and cultured as neurospheres in the presence of 20 ng/ml EGF and 10 ng/ml bFGF as described in Gritti et al. (2001). Briefly, timed pregnant mice were sacrificed and the embryos removed. Under sterile conditions the brains were removed and the forebrains dissected. The tissue was dissociated by trituration and pelleted by 75 g centrifugation for 10 minutes and the cells seeded in non-coated tissue culture flasks in NSA medium with growth factors. For passaging neurospheres were triturated and seeded as single cells.

To determine whether NRPs could induce a shift of cells within neurospheres from symmetric (two stem cells, both stem cells) to asymmetric division of neural stem cells (1 stem cell, 1 neuronal progenitor or neuroblast cell), as has been described for erythropoietin (EPO) by Shingo et al. (2001), neurospheres were dissociated by trituration and seeded for expansion at a density of 200,000 cells/well in 6 well plates in NSA medium with EGF only, EGF plus varying concentrations of an NRP, or EGF plus 10 U/ml EPO. One half of the medium with fresh NRP compound was exchanged every other day. After 7 days the cells from the neurospheres were plated. In the presence of EGF, cells retain symmetric cell division. With the removal of EGF, cells begin to differentiate (asymmetric cell division). Subsequently, the cells were subjected to a differentiation assay as described below, with the exception that bFGF was not added to the plating medium for the initial 24 h and differentiation for 7 days was allowed in control medium without NRPs or other compounds. In cells that had never been exposed to an NRP, the numbers of neuroblast cells were lower than in cells that had been exposed to an NRP or EPO. Therefore, NRPs can increase the differentiation of undifferentiated stem cells into neuroblast cells.

Differentiation Assay

Upon reaching a sufficient size, neurospheres were dissociated by trituration and plated at a density of 200,000 cells per well on laminin-coated 13 mm diameter coverslips that had been placed in Nunc 24 well plates. The plating medium was a 1:1 mixture of DMEM/F12 supplemented with N2 and Neurobasal supplemented with B27 and 2 mM glutamine. To enhance survival after plating the medium contained 2 ng/ml bFGF. After 24 h the medium was replaced with a neuronal differentiation-promoting medium (1:3 mixture of DMEM/F12 supplemented with N2 and Neurobasal supplemented with B27 and 2 mM glutamine) and except for the controls the test compound or IGF-1 was added simultaneously. The medium with fresh compound was exchanged every other day. Seven days after plating the differentiating cells were incubated for 20 minutes in differentiation medium containing 100 ng/ml Syto21 to label the nuclei of viable cells. Subsequently, they were fixed with 4% paraformaldehyde and immunostained with a mouse anti-βIII tubulin antibody and a goat anti-mouse Cy3-coupled secondary antibody.

Quantification of Neuronal Differentiation and Axonal Outgrowth

After staining the coverslips were removed from the tissue culture plate and mounted on coverslips, using Immunofluore fluorescent mounting medium. To analyse the percentage of neurons of total cells, with a Zeiss axiophot microscope, equipped with Axoivision software, at 20× magnification images of two random fields per well were taken in the red (tubulin stained neurons) and green (Syto21 stained nuclei) fluorescent channel. Neurons and nuclei per field were counted and the neuronal percentage of total cell number determined. Results of these studies are shown in FIGS. 33A-33H.

Results

Over a wide concentration range NRP-7 segment SW increased the percentage of neuronal progeny from NSC, plated on laminin in differentiation medium when normalising the neuronal cell number to the total viable cell number within the differentiation assay. At a concentration of 10 pM a maximum of 2-fold increase in beta-III-tubulin-positive neurons was observed (FIG. 33E) while the maximum activity for an increase in axonal length growth lies in the upper nanomolar range (FIG. 33A). IGF-1 is used as a positive control for axonal outgrowth promotion (Ishii et al., 1993) and is similar efficient as NRP but less potent when used at lower concentrations (FIG. 33A). When administering rat 21 mer NRP-9 during differentiation of NSC together with BrdU for 24 hrs, an increase in the proliferation rate can be observed (FIG. 33H), which makes it likely, that the increased neuronal percentage in the assay is at least partly due to proliferation of neuronal progenitor cells.

NRP-7SW and NRP-2KS had axonal outgrowth-promoting activity of differentiating neural precursor cells with similar efficacy as IGF-1 does but with much higher potency than IGF-1 (FIG. 33A/B).

Quantification of these data for NRP-2KS is given as examples in FIG. 33C (vehicle treatment) and in FIG. 33D (NRP-2KS treatment).

Over a wide concentration range NRP-2KS increased the percentage of neuronal progeny from NSC, plated on laminin in differentiation medium when normalising the neuronal cell number to the total viable cell number within the differentiation assay. At a concentration of 10nM a maximum of 2-fold increase in beta-III-tubulin-positive neurons was observed (FIG. 33F). When administering NRP-2KS during differentiation of NSC together with BrdU for 24 hrs, an increase in the proliferation rate can be observed (FIG. 33G), which makes it likely, that the increased neuronal percentage in the assay is at least partly due to proliferation of neuronal progenitor cells.

Example 12

Use of NRPs to Promote Neural Repopulation In Vivo

In light of the findings described in Example 12 and elsewhere herein, we carry out in vivo studies to determine whether NPRs can promote repopulation of neural tissue in animals. OEG cells have been evaluated as a source of cells for repopulation of neural tissue after injury, such in spinal cord injury. OEG cells are obtained using methods known in the art and are grown in cell culture. NPRs are added to the OEG cells in culture and/or are co-administered along with OEG cells in transplantation procedures of the spinal cord. Patients with spinal cord injury are prepared for surgery at the site of damage, the spinal canal is accessed using methods know in the art, and the area of damage identified. OEG cells and NRPs are transplanted into the site of injury and, optionally additional sources of NRPs are provided locally.

Example 13

Expression of NRPs

Methods

NRP Gene Expression Analysis

Expression of the annotated mouse NRP gene was confirmed by RT-PCR, Northern blot and in situ hybridisation.

In situ Hybridisation and Northern Blot

An 88-mer oligonucleotide encompassing the mouse NRP (NRP-7 (SEQ ID NO:35)) specific coding region upstream of the alkB homologue gene transcriptional start site was cloned between the BamHI and EcoRI sites of pGEM7Zf(-) (Promega, Madison, Wis., USA). The complimentary synthetic oligonucleotides; mfsNRP.S88, sense strand is shown below.

5' AATTCGGAATGAATCGAAACCCTGGAGTCGTGAC SEQ ID NO:41

CCCGGAAGAACCTGCCAGAGCCGGAATTTCGAGTTCT

GCTTCCGGGCCAAACTG and mfsNRP.AS88, the antisense strand is shown below.

5' GATCCAGTTTGGCCCGGAAGCAGAACTCGAAATT SEQ ID NO:42

CCGGCTCTGGCAGGTTCTTCCGGGGTCACGACTCCAG

GGTTTCGATTCATTCCG (Invitrogen), that also provided the appropriate 5' overhangs (underlined) were denatured and annealed at 48 uM each oligonucleotide in 100 mM NaCl, 0.1 mM EDTA (Sigma), 20 mM HEPES pH7.9 by heating 2 min at 95° C., cooling to 60° C. at 1° C./min and maintaining at 60° C. for another 1.5 h. One μl annealed 88-mer and 300 ng Qiaex extracted (Qiagen), gel purified, BamHI (Roche Diagnostics Ltd., Auckland, New Zealand) EcoRI (New England Biolabs Inc.) double digested pGEM7Zf(-) were ligated 19 h at 4° C. with 0.2 unit T4 ligase (Epicentre, Madison, Wis., USA). Clones prepared in competent DH10B (Invitrogen) were screened for the presence of a ClaI (Roche) resistant plasmid and excision of the 88-mer upon EcoRI/BamHI double digest. Templates for synthesis of sense and anti-sense RNA probes were prepared by digesting 10 μg DNA (prepared using a JetStar Maxi Kit, Genomed) to completion with 20U of either BamHI or EcoRI, respectively. The templates were gel purified using a Concert Rapid Gel Extraction System (Invitrogen).

Riboprobes were transcribed and Northern blots performed using the DIG Northern Starter Kit (Roche). 10 μg total RNA from perinatal astrocytes or pUSE-myc-mNRP-transfected HEK cells were separated on a 1.2% formaldehyde RNA gel with 0.16-1.77 kb RNA ladder and transferred in SSC to a positively charged nylon membrane (Roche). The marker lane was cut off and stained with methylene blue. The DIG-labelled NRP probe was hybridized at 52° C. over night. After stringent washes and DIG-antibody incubation, the signal was detected by CDP* luminescence with a Bioimaging System (UVP). Whole brains were extracted from E15 mice, fixed in 4% PFA for 3 hrs, cryoprotected in 20% Sucrose o/n, embedded in Tissuetek OCT medium and stored at -80° C. The cryoprotected brains were cut into 14 μm sections on PLL coated slides, treated with 8 ug/mal Proteinase K for 8 min, post-fixed with 4% PFA for 5 min, and hybridised o/n at 45° C. with DIG-labelled NRP probe (88-mer Probe sequence) (1:100 dilution), with sense controls. After labelling with anti-DIG antibody and color development of the signal with NBT/BCIP, the sections were double labelled with nestin/GFAP/b-tubulin, and were visualised using fluorescent secondary antibody.

Results

Figure 34B:
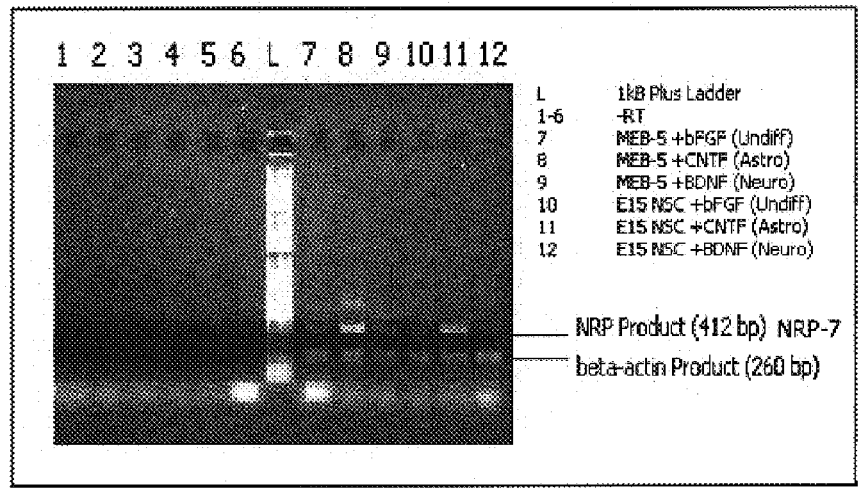
Figure 34C:
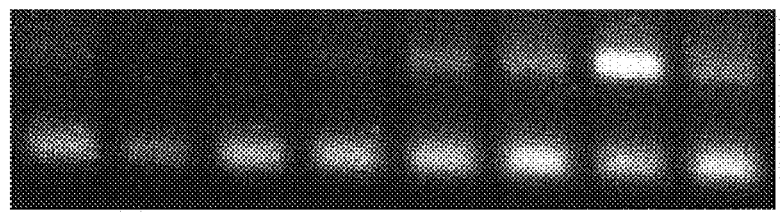
Figure 34D:
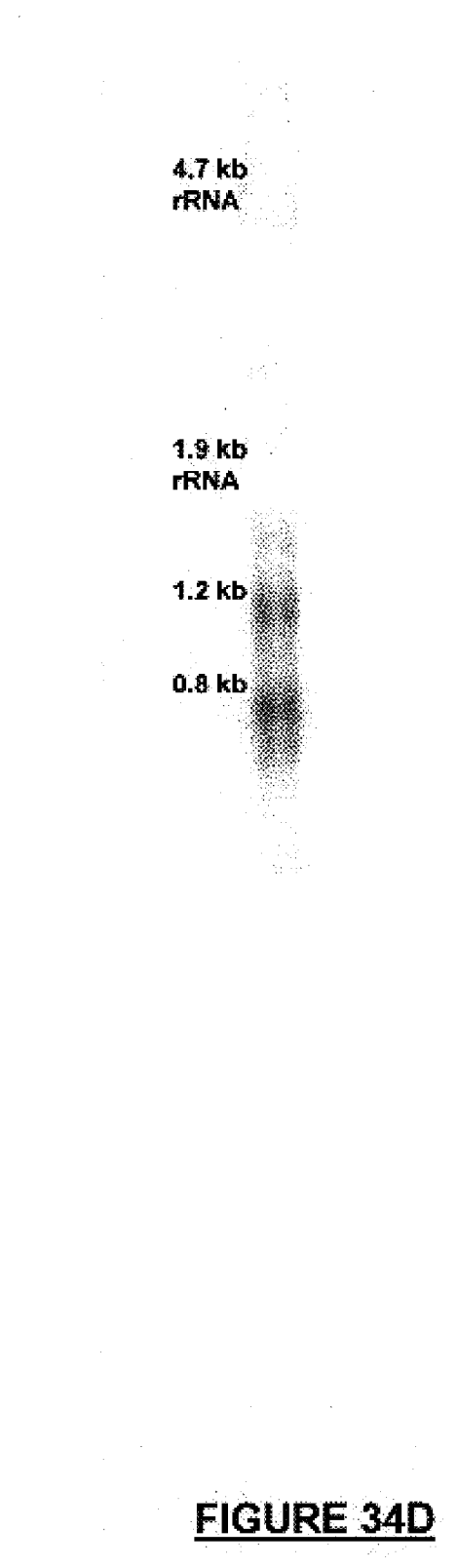
Figure 34L:
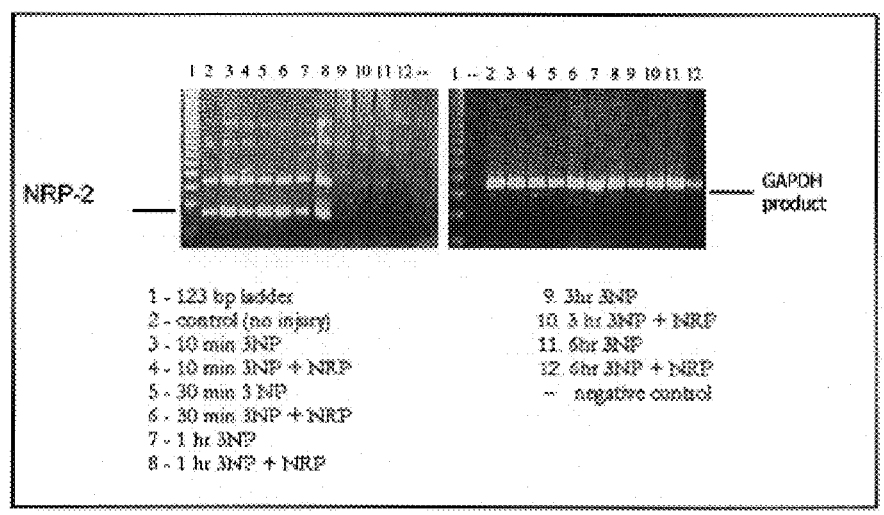

Employing PCR the NRP message was detected in different regions of the E15 embryonic mouse brain, but interestingly the expression level was much higher in cultured mouse neural stem cells (FIG. 34A). Neural stem cell specific expression was further substantiated by in situ hybridisation for mouse NRP mRNA and double staining with the stem/progenitor specific intermediate filament nestin (Lendahl et al. 1990) (FIGS. 34E-34H). In order to assess, whether the NRP message (mRNA) would be maintained in neuronal or glial progeny from NSC, the expression level in undifferentiated NSC was compared to NSC differentiated into astrocytes with CNTF and NSC coaxed to differentiate into neurons by BDNF. The NRP expression level was markedly increased only in the CNTF treated cells, indicating astrocytic lineages as the major source for secreted protein (FIG. 34B). Comparing expression levels in several tissues from E19 mouse, it became apparent that, except for the lung, expression in non-nervous tissues was lower, or even absent (FIG. 34C). Based on the relatively high expression level in astrocytes, a northern blot on RNA from perinatal astrocyte cultures was attempted, which revealed two transcripts of approximately 0.8 and 1.2 kb size, which correspond to predicted full-length transcripts, for transcription starts -114 and -509 upstream of the translation start (FIG. 34D). In situ hybridisation on sections of the E15 mouse embryonic forebrain, revealed an intense signal in the marginal zone and subplate, complemented by a lighter labelling of the cortical plate (FIG. 34I). Mouse NRP mRNA was co-localized with nestin-immununoreactivity. At this stage no co-labelling with GFAP or MAP2 was observed (data not shown). This staining pattern indicates expression in radial glial-like cells, undergoing transformation into immature astrocytes (Steindler & Laywell, 2003).

Example 14

Cerebellar Microexplants III—Neuroprotection Comparison of NRP-2 Segment SW (SEQ ID NO: 24 and SDF-1)

Methods

Cerebellar Microexplants were prepared as described in Example 9 with the addition of SDF-1 as described, in addition to glutamate/3-NP, and NRP.

Results

The resulting injury from treatment of unprotected cerebellar microexplants for 48 hrs with 0.5 mM 3-NP/glutamate was in the range from 75-92% cell death. FIG. 35A shows that NRP-7SW conferred highly significant neuroprotection over the concentration range from 100 fM to 100 nM and showed almost 50% recovery from injury at 100 μM. In comparison, 10 nM human SDF-1 conferred less than 30% neuroprotection and revealed a narrow dose range of efficacy (FIG. 35B).

The 16 mer- cachexia fragment had lower efficacy and a ten-fold lower potency for neuroprotection and induction of neuronal proliferation (data not shown).

Example 15

Induction of Neuronal Migration: Comparison of NRP-9 Segment SD (SEQ ID NO: 34), NRP-2 segment SW (SEQ ID NO: 24) and SDF-1

Method for Haptotactic Migration Assay

A haptotactic migration assay was performed according to the description of Example 10 using rat NRP-9SD (SEQ ID NO:34) (4 nM) and mouse NRP-7SW (SEQ ID NO:24) (0.4 nM) as attractants in a Boyden chamber Method for Thalamaco-Cortical Cultures The occipital cortex and dorsal thalamus from newborn Long Evans rats (P0) was dissected, according to the P0 atlas of Paxinos[37]. Occipital cortex was coronally, dorsal thalamus frontally cut with a tissue shopper (McIlwain) into 350 μm-thick slices, which were transferred immediately into Gey's Balanced Salt Solution (GBSS) supplemented with 0.65% D-glucose (Merck) and allowed to recover at 7° C. for one hour. Thalamic slices with perpendicular orientation were selected under a stereomicroscope and arranged with cortical tissue at a distance of at least 3 mm on cover slips. In this case, the thalamus was orientated with the habenula nucleus facing cortical layer VI. The slices were adhered to the cover slips in a plasma clot by 10 ill of chicken plasma (Cocalico), coagulated with 10 μl of thrombin (25 U/ml, ICN). Cover slips were placed in roller tubes (Nunc) and supplied with 0.75 semi-artificial culture medium [2/4 Basal Medium Eagle, 1/4 Hank's Balanced Salt Solution, 1/4 inactivated horse serum, 2 mM L-glutamine and 0.65% D-glucose. Cultures were maintained in a roller tube incubator at 36° C. for up to 20 days in vitro (DIV) and media containing rat cachexia-related NRP was exchanged every three days.

OTCs of rat embryonic forebrain were prepared as described. Briefly, pregnant rats at E17 gestation were sacrificed, the fetuses rapidly removed. Coronal slices of the forebrain were cut at 400 μm thickness and placed onto millicell PICM ORG50 membranes (Millipore) in 3 cm Petri dishes containing 1 ml of DMEMI/F12, 6.5 mg/ml glucose, 0.1 mM glutamine and 10% FCS for 34 hrs. Afterwards the medium was exchanged to 1 ml Neurobasal/B27, 6.5 mg/ml glucose, 0.1 mM glutamine, to which 10 μl PBS, NRP, or SDF-1 were added for the indicated concentrations and a small DiI (1,1'-dioctodecycyl-3,3,3'3-tetramethylindocarbocyanine) crystal of uniform size was placed in the medial ganglionic eminence (n=10-15) under a stereomicroscope. After 24 hrs cultivation the total number or migrated neurons dispersed in the ganglionic eminence and cortex were counted under an inverted fluorescent microscope.

Results

.NRP-9SD (SEQ ID NO:34) (4 nM) and mouse NRP-7SW (SEQ ID NO:24) (0.4 nM) exhibited substantial chemoattractive activity of the NRPs on mouse neural stem cells. Nearly four times as many cells as in control condition are attracted by the NRP-9SD while 10-fold less amount of NRP-7SW still attracted 2-fold more NSCs to the culture dish bottom. In comparison, 100 nM of SDF-1 coating attracted a similar number of cells, as did the 0.4 nM mouse NRP-7SW (FIG. 36A). Their representative morphological phenotype is depicted in FIG. 36B.

In an OTC assay using sagittal embryonic brain slices that include the ganglionic eminence and the cortical anlage NRP-7SW administered to the OTC lead to a 5-fold increase in number of migrating neuronal precursor cells (FIG. 36C). Human SDF-1 induces similar numbers of cells to migrate from the medial ganglionic eminence to the cortical anlage but as in the haptotactic migration assay the 63 amino acid long mature human SDF-1 is far less potent than NRP.

Example 16

Recombinant NRP Expression and Activity Assays

Preparation of HEK293-Expressing mfsNRP

HEK293 cells were transfected with N-terminal and C-terminal tagged MNRP fusion protein expression constructs (pUSE-Flag-mNRP2 and pUSE-myc-mNRP11, respectively) using 25 KDa polyethyleneimine (Boussif et al.; 1995). The NRP sequence used was SEQ ID NO:35. Parallel transfections with pEGFP-N1 (Clontech) were also performed. Briefly, each construct was combined with PEI at ratios of 6, 9 and 12 to 1 PEI nitrogen to DNA phosphate at 10 ng/ul DNA in 5% glucose. HEK293 cells at 70% confluence in 2 ml growth medium (DMEM supplemented with 10% fetal calf serum) in 36 mm wells were transfected by 4.5 h incubation with 200 ul of transfection mix per well. After this, 2 ml growth medium with 2× antibiotic/antimycotic mix were added to each well. The following day, the cultures were split 1:15 using 1 ml/well Trypsin-EDTA into growth medium containing 800 pg/ml of geneticin. Selection was maintained for 17 days with changes of medium twice a week. Upon confluence, selection was continued on a portion of cells at a 1:10 split and the remainder were frozen in growth medium containing 10% DMSO. Additionally, a 1:2 split from the 800 μg/ml geneticin selection was prepared day 13 Stable transfectants were harvested for detection of expressed, tagged proteins.

Western Blotting Confirmed Expression of Myc-NRP in HEK293 Cells

Western blotting was carried out to confirm expression of Myc-NRP in HEK293 cells. Cell lysates were solubilised under denaturing conditions and proteins were separated using SDS polyacrylamide gel electrophoresis (PAGE). Expressed recombinant mouse Myc-NRP is detected by monoclonal anti-Myc antibody.

Results

Figure 37A:
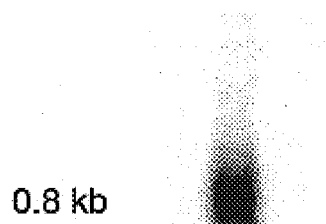
Figure 37B:
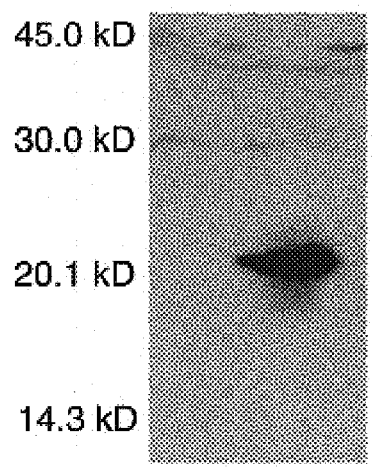

The creation of full-length recombinant mouse NRP under the control of a c-myc promoter transfected into HEK-cells revealed an expected 0.8 kb-sized transcript when probed with the antisense 88 bp NRP cRNA (FIG. 37A). The 16.5 kDa recombinant protein product expressed by the Myc-NRP-HEK cells migrated on a Laemmli SDS-gel to the protein marker size of 20 kDa (FIG. 37B).

Figure 37C:
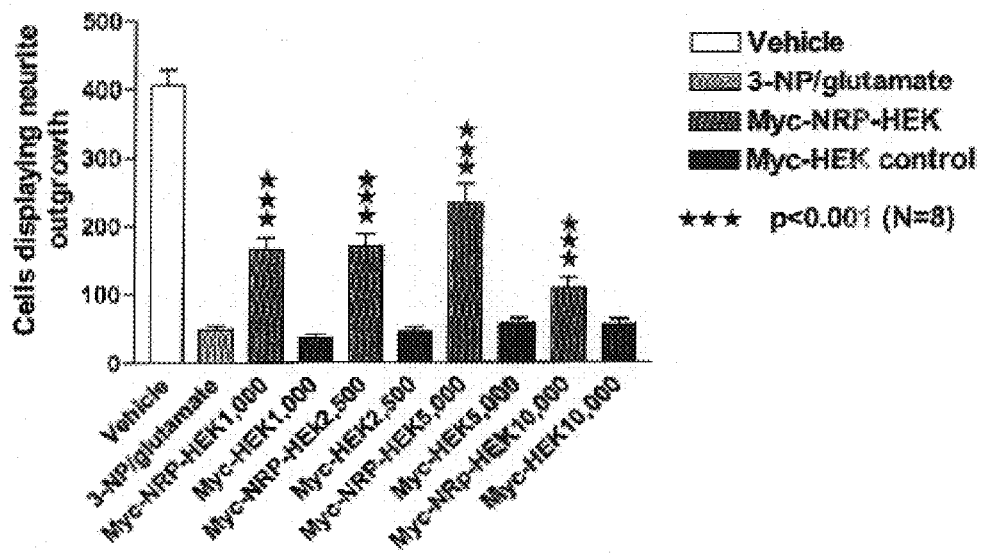

The measured biological activities of the expressed recombinant complete NRP gene product encoded by the NRP gene equalled those of the tested NRP synthetic peptides. In a co-culture assay together with cerebellar microexplants Myc-NRP-HEK cells conferred substantial neuroprotection when seeded at different cell concentrations, with a recovery value of 51% of MAP-2-positive neurons at a Myc-NRP-HEK cell number of 5000 (FIG. 37C). Control Myc-HEK possessing the empty vector only, did not reveal any recovery of MAP-2-positive cells after oxidative/excitotoxic stress. The added recombinant HEK cells revealed a bell-shaped dose response curve for neuroprotection.

Figure 37D:
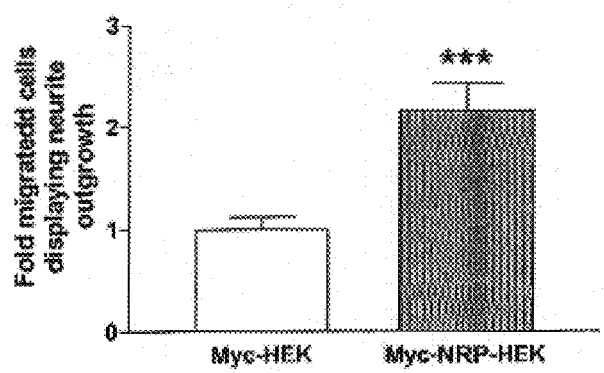

The Myc-NRP-HEK cells displayed chemoattractive neuronal migration-inducing activity when tested in the haptotactic migration assay using mouse NSCs. When mouse NRP expressing Myc-NRP-HEK cells were seeded onto the bottom of the Boyden chamber and mouse NSCs were seeded into the inserts, the detected neuronal cell population after 24 hrs displaying neurite outgrowth was two-fold increased compared to the same assay using control Myc-HEK cells (FIG. 37D).

Example 17

Possible Mechanism of Action of NRPs

Recent data suggest that SDF-1 (CXCL12) and its receptor CXCR4 may have parallel effects in the immune and nervous systems: they can regulate cellular movement, proliferation, plasticity (neurite outgrowth and differentiation) and survival of neurons and lymphocytes (Vlahakis et al., 2002 and Lazarini et al., 2003). Parallel reliance on CXCL12 might support coordinated homeostatic interactions but might also constitute a unique vulnerability to inflammatory processes, as HIV-1 infection and subsequent suffering of neuropathy, as a result to CXCR4 receptor binding (Keswani et al., 2003). HIV and related viruses require co-receptors, in addition to the lymphocyte receptor CD-4, to infect target cells. One of the HIV-used co-receptors is the G-protein coupled chemokine receptor CXCR4. SDF-1 interaction with CXCR4 can prevent HIV entry into the CD4-lymphocyte. Moreover, it is known that cancer metastasis can be prevented by inhibiting the migration/invasion of cancer cells by antagonizing the CXCR4-receptor in animal models (Rubin et al., 2003, Liang et al., 2004).

So far, SDF-1 is the only known ligand binding to the CXCR4 receptor. We provide here some evidence that the NRPs can represent a new class of ligands for the CXCR4 receptor and that biological activity (e.g. chemoattraction and neuronal survival) can be exerted by activation of CXCR4 receptors. Thus, NRPs can be agonists for the CXCR4 receptor without excluding the possibility that there might be antagonistic effects of NRPs on the CXCR4 receptor as well. Similar observations were made for SDF-1: single amino acid substitution can antagonize SDF-1 effects on CXCR4 (Tudan et al., WO0185196). It should be understood however, that this is not the only possible mechanism of action of NRPs, and that other mechanisms may account for the observations described herein.

Methods

Cerebellar microexplants were prepared as described in Example 9 with the addition of SDF-1, Wortmannin and PD98059 (both Calbiochem), as described, in addition to glutamate/3-NP, and NRP.

Effects of Neutralizing Antibodies Against CXCR4 Receptor on Survival-Promoting and Migration-Inducing Activities of NRPs Application of 1 ug/ml of a neutralizing antibody raised against the CXCR4 receptor (fusin receptor) for 72 hours significantly decreased neuronal survival and neuronal migration patterns within cerebellar microexplants treated with NRPs. At an antibody concentration of 1 μg/ml, neuroprotective and/or migration-promoting effects of NRP-9 SD (SEQ ID NO:34) were abolished (FIG. 38A). Similar inhibition was observed for the human NRP-2KS (SEQ ID NO:23) (FIG. 38B) or mouse NRP-7SW (SEQ ID NO:24).

Effects of Neutralizing Antibodies Against CXCR4 Receptors on Chemoattractive Actions of NRPs Chemoattractive effects of 10 ng/ml NRP coated to the culture dish were blocked by pre-incubating the neuronal stem cell line MEB-5 for 1.5 hrs with a neutralizing antibody for CXCR4. Significantly fewer cells migrated compared to the migration observed with NRP-9 SD (SEQ ID NO:34) peptide alone (FIG. 38C).

NRP Action Can Be Mediated by ERK1/2 and Akt Phosphorylation

To investigate the signalling pathways utilized by NRP to exert neuroprotective and/or migratory effects we used the MEK inhibitor PD98509 and the phosphatidylinositol 3-kinase (PI-3K) inhibitor wortmannin to block MAPK or Akt phosphorylation.

To address the role of MAPK and the upstream regulator of akt activity PI-3K (phosphorylation of Akt) in the mechanism of action of NRP-mediated neuroprotection and chemoattraction we tested the MAPK kinase (MEK) inhibitor PD98509 for efficacy in the cerebellar microexplant and haptotactic migration assays. The vehicle and injury treatment with and without PD98509 revealed only modest toxicity of the inhibitor, while simultaneous treatment of the inhibitor with NRP-9 SD (SEQ ID NO:34) abolished the neuroprotective activity of NRP (FIG. 39A). The inhibition of Akt phosphorylation with wortmannin (100 nM) had no significant effect after vehicle and injury conditions without the NRP, but similar to the inhibition of ERK1/2 phosphorylation, abolished neuroprotection produced by NRP (FIG. 39B). In the haptotactic migration assay the nearly three-fold increase in migrating NSC was almost completely blocked with PD98509 (from 0.1 pM to 100 pM), with no significant effect on basal migration in the BSA coated wells (FIG. 39C). In contrast to neuroprotection, the chemoattractive migratory activity of NRPs was not suppressed by inhibition of PI-3K with wortmannin (data not shown). To exclude that the reduced number of migrated cells at the bottom compartment could have been due to impaired neuronal survival, the insert was stained for live cells with Syto21 and the upper surface analysed. No significant difference in the number of surviving cells was found.

Example 18

NRP Efficacy in Vivo

Materials and Methods

To test the efficacy of NRPs in vivo studies were carried out in rats that had been exposed to hypoxic-ischemic injury (HI). Adult rats (50 days old, Wistar, 250-300 g, male) were used. The modified Levine model preparation and experimental procedures were used (Rice et al, 1981, *Ann. Neurol.* 9: 131-141; Guan et al *J.*, 1993, *Cereb. Blood Flow Metab.*: 13(4): 609-16). These procedures in brief, consist of an HI injury induced by unilateral carotid artery ligation followed by inhalational asphyxia in the animals with an implanted lateral ventricular cannula. A guide cannula was stereotaxically placed on the top of the dura 1.5 mm to the right of the mid-line and 7.5 mm anterior to the interaural zero plane under halothane anaesthesia. The right carotid artery was double ligated two days after the cannulation. After a 1-hour recovery period from anaesthesia, each of the rats was placed in an incubator where the humidity (90±5%) and temperature (31°±5° C.) were controlled for another hour, and then each of the rats was exposed to hypoxia (6% oxygen) for 10 min. The animals were kept in the incubator for an additional 2 hours before treatment.

Rats were treated intracerebral ventricularly (icv) with 5 nM (n=12), 50 nM (n=12) or 500 nM of NRP-4 segment PQ (PGRAEAGGQ; SEQ ID NO:43) dissolved in saline, or vehicle (n=10) (normal saline) 2 hours after hypoxic-ischemic insult.

Histological examination was performed on rats 5 days after the hypoxic-ischemic injury. The rats were killed with an overdose of sodium pentobarbital and were perfused transcardially with normal saline followed by 10% formalin. The brains were kept in the same fixative for a minimum of 2 days before being processed using a standard paraffin imbedding procedure.

Coronal sections 8 μm in thickness were cut from the striatum, cerebral cortex and hippocampus and were stained with thionin and acid fuchsin. The severity of tissue damage was scored in the striatum, cortex and the CA1-2, CA3, CA4 and dentate gyrus of the hippocampus. Tissue damage was identified as neuronal loss (acidophilic (red) cytoplasm and contracted nuclei), pan-necrosis and cellular reactions. Tissue damage was scored using the following scoring system: 0: tissue showed no tissue damage, 1:<5% tissue was damaged, 2:<50% tissue was damaged, 3:>50% tissue was damaged and 4:>95% tissue was damaged.

Results and Conclusion

The results of this study are shown in FIG. 40. The 9 mer-fragrnent of human chromosome 15, NRP-4 segment PQ (PGRAEAGGQ-NH$_2$; SEQ ID NO:43; 9 ng/20 μl icv 2 hrs after hypoxia), conferred 100% neuroprotection within all analysed brain regions five days after insult.

Example 19

Growth Promotion of Olfactory Ensheating Glial ("OEG") Cells

To determine whether NRPs might be useful for remyelinating neural tissues, we carried out studies using human olfactory ensheating glial (OEG) cells. OEG cells are being evaluated as a source population of cells for repopulating damaged neural tissue, such as that of the spinal cord. OEG cells were obtained from scrapings of human nasal mucosa using methods that are known in the art. Cells were grown in medium under control conditions and in the presence of NRP-7 SW (SEQ ID NO:24).

Under control conditions, the normal rate of proliferation of OEG cells is about 25% within 72 hours. We found that in the presence of NRP-7 SW (SEQ ID NO:24), the OEG cells grew at a rate of about 50% over 72 hours. These results indicate that NRPs can enhance proliferation of OEG cells, and thereby can be useful in neural cell transplant procedures to promote cell growth and return of neural function to damaged tissues (FIG. 41)

Example 20

Neuroprotective Activity of NRP-5 Segment RG Peptide Analogues

To determine if alteration in the amino acid sequence of peptides related to NRP-5 Segment RG produced peptides having activity different from that of NRP-5 Segment RG (SEQ ID NO:30), we produced synthetic peptides having various amino acid substations. We tested substituted NRP-5 RG peptides in the cerebellar microexplant assays described herein.

Amino acid substitutions within the first N-terminal five amino acids of the amidated peptide having amino acid sequence REGRRDAPGRAGG-NH$_2$ (SEQ ID NO:30) produced a peptide having the sequence: REAAADAPGRAGG-NH$_2$ (SEQ ID NO:44) and AAARRDAPGRAGG-NH$_2$ (SEQ ID NO:45).

Amino acid substitutions in the PGR-domain resulting in a peptide having the amino acid sequence REGR-RDAAAAAGG-NH$_2$ (SEQ ID NO:47) and substitution of the C-terminal GG-domain resulting in a peptide having the amino acid sequence REGRRDAPGRAAA-NH$_2$ (SEQ ID NO:46). Each of the above substituted peptides were tested and the results comnpared to those obtained using NRP-5 Segment RG (SEQ ID NO:30; "NRP-5 RG").

Figure 42A:
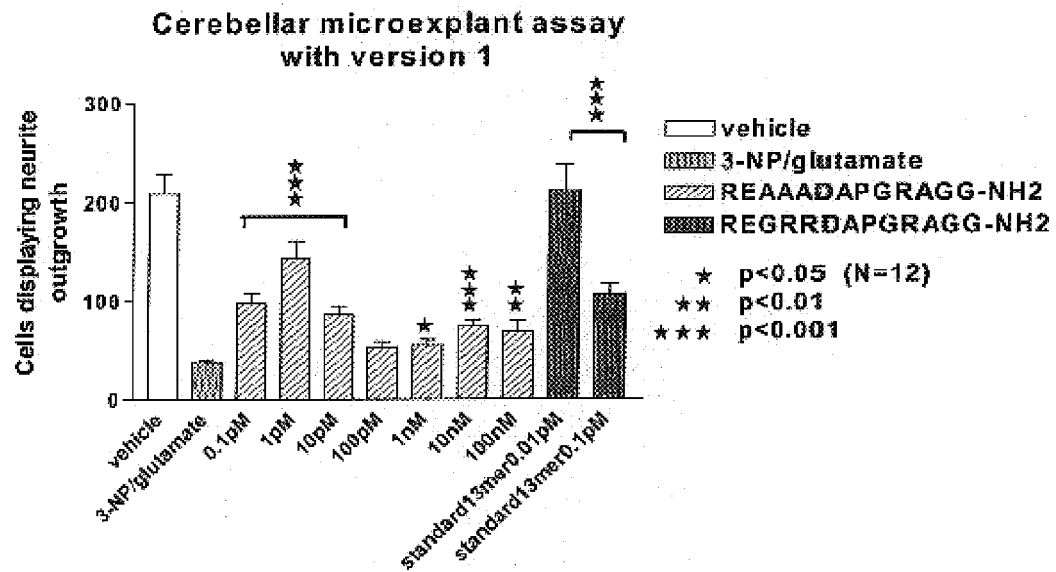

FIG. 42A shows that SEQ ID NO:44 had neuroprotective activity with a maximum effect observed at a concentration of about 1 pM. The bars on the right, labeled "standard13mer," refer to NRP-5 RG (SEQ ID NO:30). The substitution of amino acids 3-5 of NRP-5 RG did not significantly change in the activity profile of the peptide (FIG. 42A).

Figure 42B:
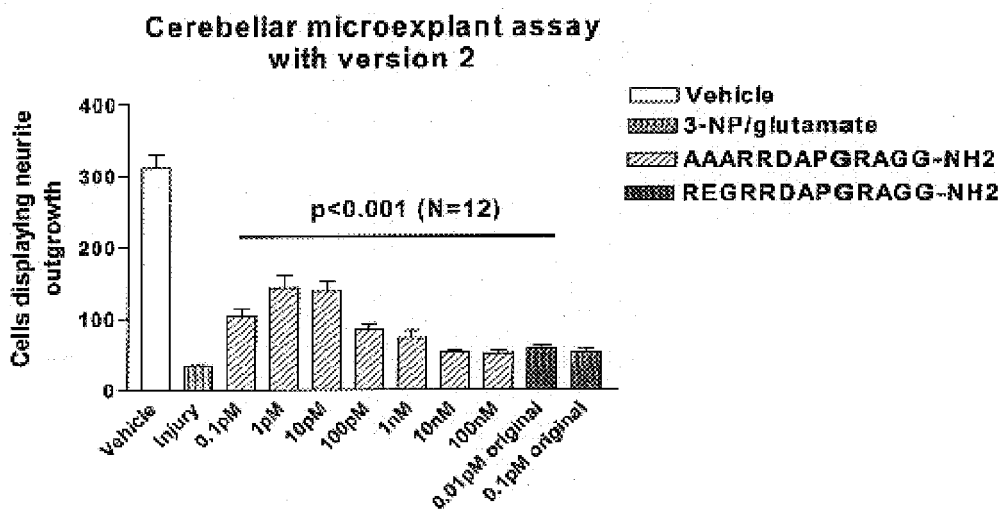

FIG. 42B shows that SEQ ID NO:45 had neuroprotective activity with a maximal effect observed at a concentration of about 1 pM. The bars on the right, labeled "original," refer to NRP-5 RG (SEQ ID NO:30). Substitutions in positions 1-3 producing AAARRDAPGRAGG-NH$_2$ (SEQ ID NO:45) resulted in even higher neuroprotective activity than the original NRP-5 RG. The result may be due to the higher stability profile of the analogue over NRP-5 RG, although other hypotheses may account for the observation.

Figure 42C:
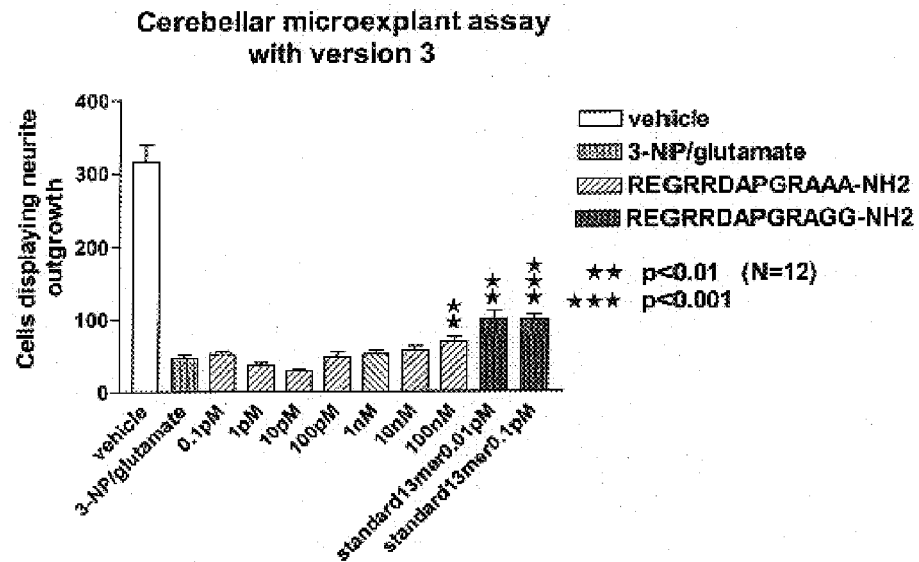

FIG. 42C shows that SEQ ID NO:46 had less effect than NRP-5 RP (SEQ ID NO:30; right bars; "standard13mer") or of SEQ ID NO:44 or SEQ ID NO:45 (FIGS. 42A and 42B, respectively). In fact, the only statistically significant effect was observed at a concentration of 100 nM. The original sequence (SEQ ID NO:30) produced 20% higher neuroprotection with $10^6$ to $10^7$ times higher potency than SEQ ID NO:46.

Figure 42D:
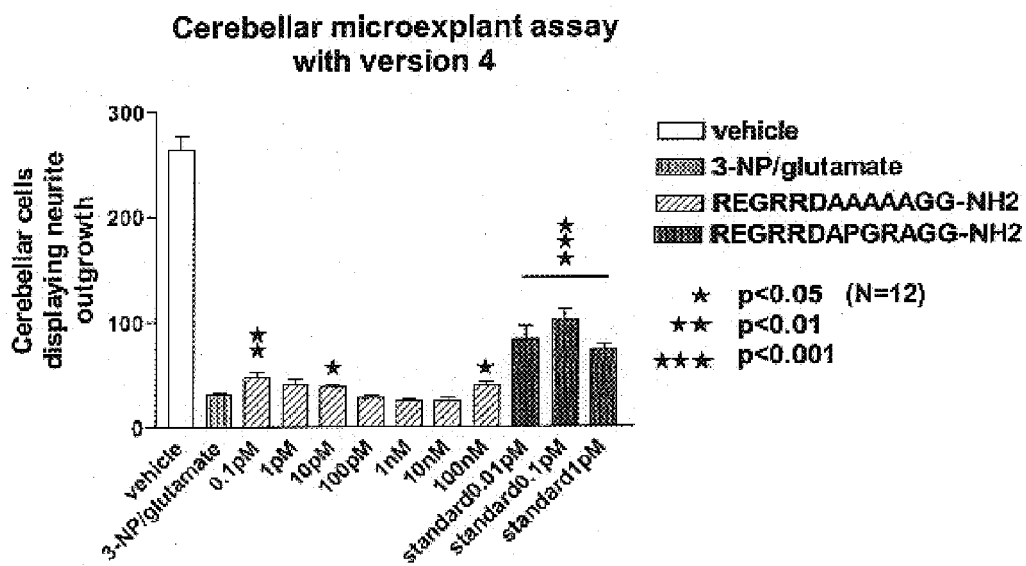

FIG. 42D shows that SEQ ID NO:47 had some neuroprotective effect at certain concentrations (e.g., 0.1 pM, 10 pM and 100 nM), but at other concentrations, had no effect compared to those observed for NRP-5 RG (SEQ ID NO:30; right bars labeled "standard").

We conclude from these studies that both the PGR and the C-terminal GG domains are useful for maintaining the activity of NRP-5 RG (SEQ ID NO:30). We also conclude that the amidated C-terminus of an NRP is not sufficient to produce neuroprotective effects, because the C-terminal amidated NRP, SEQ ID NO:46, produced little if any neuroprotective effect at most concentrations. Further, alteration in the interior of an NRP did affect activity, even though none of the interior amino acids has a C-terminal amide group.

Example 21

Proliferation-Inducing and Chemoattractive Activities of NRP-5 RG

In another set of studies, we determined effects of NRP-5 RG on induction of neural cell proliferation in embryonic cerebellar microexplants as described herein. FIG. 43 shows that NRP-5 RG exhibited proliferation-inducing activity with a maximal activity observed at a concentration of 100 pM. Some effect was observed at concentrations of 1 mP and even at 0.1 pM, but those effects were not statistically significant.

In additional studies, we studied chemoattractive effects of NRP-5 RG in a haptotactic migration assay as described herein. FIG. 44 shows that NRP-5 RG was chemoattractive, and had 42.1% greater effect than cells exposed to control (BSA-containing) medium.

Example 22

NRPs Protected Neural Cells In Response to Oxidative Stress

In this series of experiments, we studied whether NRP-4 Segment PQ ("NRP-4 PQ") was able to protect cerebellar microexplanted cells from oxidative injury. We exposed cells to vehicle, 0.1 mM hydrogen peroxide or different concentrations of NRP-4 PQ in vehicle. FIG. 45 shows neuroprotective effects of NRP-4 PQ after 48 hrs of oxidative stress in response to 0.1 mM hydrogen peroxide. The neuroprotection associated with NRP-4 PQ treatment was even greater than that of control explants receiving no peroxide. Although the mechanism for this potentiation of neurite outgrowth is uncertain, it may relieve the stresses associated with creating or maintaining the microexplants themselves.

These findings are relevant to many conditions in which oxidative stress plays a role. For example, oxidative stress is associated with all both and chronic CNS injuries and diseases. Inhibition of oxidative-stress mediated neurotoxicity through NRP action can be highly beneficial for many CNS injuries or diseases.

Example 23

Neuroprotection Mediated by Phosphorylated NRP-7 SW

We carried out a series of studies to determine whether phosphorylation of the N-terminal amino acid serine altered neuroprotective effects of NRP-7 Segment SW ("NRP-7 SW"). Phosphorylation of NRP-7 SW produces NRP-7$^P$SW. We hypothesized a role for N-terminal serine phosphorylation because of the high likelihood prediction (0.9) that serine is phosphorylated under in vivo conditions (NetPhos 2.0 Server—Technical University of Denmark). Cerebellar microexplants were injured with 0.5 mM 3-NP/glutamate and treated with NRP-7$^P$SW.

FIG. 46 shows results of experiments that demonstrate that NRP-7$^P$SW exhibited neuroprotective effects, with significant effects observed at concentrations as low as 0.1 µM, which exhibited more neuroprotective activity (44.2% neuroprotection) than other concentrations tested. Because the lowest concentration used (0.1 µM) exhibited substantial neuroprotective effects, lower concentrations will also exhibit neuroprotective effects.

Example 24

Enhancement of Proliferation of NSCs After Induction of Differentiation by NRP-9 SD E15 mouse NSC P10 cells were plated on laminin and cultured for 3 days in the presence of NRP-9 SD (SEQ ID NO:34) and BrDU for the last 48 hours of the culture period. For each condition 4 visual fields in two independent wells were counted and the number of proliferating cells were determined.

Results

NRP-9 SD increased the rate of proliferation of differentiating mouse NSC precursor cells (FIG. 47). This biological activity was observed over a wide dose range from 100 fM to 1 nM.

Example 25

Expression of NRPs II

In Situ Hybridisation

Whole brains were extracted from E15 and E17 mice, fixed in 4% paraformaldehyde (PFA) for 3 hrs, cryoprotected in 20% sucrose overnight (o/n), embedded in Tissuetek OCT (Sakura fmetek) and stored at −80° C. The cryoprotected brains were cut into 14 µm thick sections, placed on PLL coated slides, treated with 8 ug/mal Proteinase K for 8 min, post-fixed with 4% PFA for 5 min, and hybridised overnight at 45° C. with DIG-labelled NRP sense and antisense probes (88-mer Probe sequence described in Example 13; sense strand: SEQ ID NO:41 and antisense strand: SEQ ID NO:42; 1:100 dilution). After labelling with anti-DIG antibody and color development of the signal with NBT/BCIP, the sections were double labelled with nestin/GFAP/DIII-tubulin and vimentin 1:100 dilution (abcam, mouse monoclonal [RV202], ab8978-1), and were visualised using fluorescent secondary antibody. The sense controls remained negative.

Results

FIGS. 48A and 48B depict fluorescence micrographs of brains of animals as described above. The co-localization of the mouse frameshift NRP message with the radial glia marker, vimentin, indicated that NRP expression was maintained in the neuroepithelial stem cell—radial glia -astrocytic lineage (FIGS. 48A and 48B). This points to an important function in neural stem cells, as radial glia have been shown to generate neurons in many brain regions during development (Anthony TE, Klein C, Fishell G, Heinz N. 2004. Radial glial cells serve as neuronal progenitors in all regions of the central nervous system. Neuron 41:881-890) and astrocytes of the adult subventricular zone have been demonstrated to be neural stem cells (Doetsch F, Caile I, Lim DA, Garcia-Verdugo JM, Alvarez-Buylla A. 1999. Subventricular zone astrocytes are neural stem cells in the adult mammalian brain. Cell 97:703-706).

We conclude from these studies that NRP mRNA is produced in the brains of mice.

Example 26

Re-Sequenced SEQ ID NO:8 and SEQ ID NO:9

On Aug. 20, 2004, a report of revised sequences corresponding to SEQ ID NO:8 and SEQ ID NO:9 were published (NBCI, NT_026446). Based on the newly identified sequences, we have annotated a nucleotide NRP sequence consisting of 225 nucleotides coding for a peptide having 75 amino acids. According to the previously annotated sequence on chromosome 15 coding for NRP (SEQ ID NO:8), the following has changed within the sequence: position 168 has changed from a G to a C; otherwise exons 1-4 remained unchanged (including the active biologically sequence for NRP). From position 179 onwards the newly annotated exon 5 starts. From position 222 onwards exon 6 starts.

```
5'-
            9               18              27              36
ATG GCT GTT GTG TTA CTT GCA CCA TTT GGG GAC ATC AGC CAG
Met Ala Val Val Leu Leu Ala Pro Phe Gly Asp Ile Ser Gln 45              54              63              72              81
GAA ATC ACA AAG GTT GGG ACA GGG ACT CCA GGG AGG GCT GAG
Glu Ile Thr Lys Val Gly Thr Gly Thr Pro Gly Arg Ala Glu
```

-continued

```
       90              99             108            117           126
GCC   GGG  GGC  CAG   GTG  TCT  CCA   TGC  CTG  GCG   GCG  TCC  TGC  AGT
Ala   Gly  Gly  Gln   Val  Ser  Pro   Cys  Leu  Ala   Ala  Ser  Cys  Ser 135             144            153           162
CAG  GCC   TAT  GGC  GCC   ATC  TTG  GCT  CAC  TGC  AAC  CTC  TGC  CTC
Gln  Ala   Tyr  Gly  Ala   Ile  Leu  Ala  His  Cys  Asn  Leu  Cys  Leu 171             180            189            198           207
CCA  GGT  TCA  AGT  GAT  CTG  CCT  GCC  TCA  GCC  TCC  CAA  AGT  GCT
Pro  Gly  Ser  Ser  Asp  Leu  Pro  Ala  Ser  Ala  Ser  Gln  Ser  Ala 216            225  228  (STOP)
AGG   TTA  CAG  GTT  GAT  TAA
Arg   Leu  Gln  Val  Asp   α
```

SEQ ID NO:48
SEQ ID NO:49

The whole amino acid sequence written in the one letter code:

>humchrom15NRPexon1 2 3 4 5 6

SEQ ID NO:49
MAVVLLAPFGDISQEITKVGTGTPGRAEAGGQVSPCLAASCSQAYGAILA

HCNLCLPGSSDLPASASQSARLQVD

Example 27

Treatment of Stroke

A patient presents with symptoms of stroke. A diagnosis of stroke is made and the physician then administers a NRP compound to the patient intravenously or alternatively, directly into the cerebral ventricle or directly into the affected portion of the patient's brain. The NRP compound is a peptide or protein as described herein and is administered in a pharmaceutically acceptable form, including, if desired, excipients, buffers and stabilizers. Treatment with the NRP decreases the neurodegeneration associated with the stroke and an expected worsening of symptoms at least partially slows, stops or is at least partially reversed.

Example 28

Prophylactic Use of NRPs

A patient is diagnosed with a cardiac vascular insufficiency and coronary artery bypass (CABG) surgery is indicated. CABG surgery is associated with reduced cerebral perfusion, which can lead to hypoxic or ischemic brain injury. To decrease adverse effects of such hypoxia or ischemia, the patient is pre-treated with a NRP compound. The NRP compound is administered to the patient in a pharmaceutically acceptable form, including, if desired, excipients and/or stabilizers. Routes of administration include intravenous, intercerebrally, or via a cerebral ventricle. If desired, multiple routes of administration can be used. Pre-treatment of a patient undergoing CABG surgery decreases the neurodegeneration associated with CABG surgery and the patient experiences reduced post-surgical neurological deficits compared to patients undergoing CABG surgery without pre-treatment with a NRP.

This invention is described with respect to specific embodiments thereof. Those of ordinary skill in the art without undue experimentation may develop other embodiments incorporating the disclosures and teachings of this application. All of these embodiments are considered to be part of this invention. All references cited herein are incorporated fully by reference.

REFERENCES

Akerblom, I E, and Murry, L E (1996). Human cachexia associated protein. U.S. Pat. No. 5,834,192.

Anderson, C V, Wood, D M, Bigler, E D, and Blatter, D D (1996). Lesion volume, injury severity, and thalamic integrity following head injury. *J. Neurotrauma* 13: 35-40.

Anderson, W F (1992) Human gene therapy. *Science* 256: 808-813.

Bach et al., (1995) Insulin like growth factor binding proteins. *Diabetes Reviews* 3: 38-61.

Baldwin, M E, Roufail, S, Halford, M M, Alitalo, K, Stacker, S A and Achen, M G (2001). Multiple forms of mouse vascular endothelial growth factor-D are generated by RNA splicing and proteolysis. *J. Biol Chem* 276: 44307-44314.

Beal, M F, Kowall, N W, Ellison, D W, Mazurek, M F, Swartz, K J, and Martin, J B (1986). Replication of the neurochemical characteristics of Huntington's disease by quinolinic acid. *Nature* 321: 168-171.

Bolz, J, Novak, N, and Staiger, V (1992). Formation of specific afferent connections on organotypic slice cultures from rat visual cortex cocultured with lateral geniculate nucleus. *J. Neurosci.* 12:3054-3070.

Brose, K, and Tessier-Lavigne, M (2000). Slit proteins: key regulators of axon guidance, axonal branching, and cell migration. *Curr. Opin. Neurobiol.* 10: 95-102.

Cote, F, Do, TH, Laflamme, L, Gallo, J-M, and Gallo-Payet, N (1999). Activation of the AT2 receptor of angiotensin II induces neurite outgrowth and cell migration in microexplant cultures of the cerebellum. *J. Biol. Chem.* 274: 31686-31692.

Cunningham, T J, Hodge, L, Speicher, D, Reim, D, Tyler-Polsz, C, Levitt, P, Eagleson, K, Kennedy, S, and Wang, Y (1998). Identification of a survival promoting peptide in medium conditioned by oxidatively stressed cell lined of nervous system origin. *J. Neurosci.* 18: 7047-7060.

De Curtis, I, and Reichardt, LF (1993). Function and spatial distribution in developing chick retina of the laminin receptor α6β1 and its isoforms. *Development* 118: 377-388.

Dodd, J, Morton, S B, Karagogeos, D, Yamamoto, M, and Jessell, TM (1988). Spatial regulation of axonal glycoprotein expression on subsets of embryonic spinal neurons. *Neuron* 1: 105-116.

Dyke, M W, Bianchi-Scarra, G, and Musso, M (2001). Characterization of a triplex DNA-binding protein encoded by an alternative reading frame of loricrin. *Eur. J. Biochem* 268: 225-234.

Fallon, J, Reid, S, Kinyamu, R, Opole, I, Opole, R, Baratta, J, Korc, M, Endo, T L, Duong, A, Nguyen, G, Karkehabadhi, M, Twardzik, D, and Loughlin, S (2000). In vivo induction of massive proliferation, directed migration, and differentiation of neural cells in the adult mammalian brain. *PNAS* 97: 14686-1491.

Ferri, R T, and Levitt, P (1995). Regulation of regional differences in the differentiation of cerebral cortical neurons by EGF family-matrix interactions. *Development* 121: 1151-1160.

Fueshko, S, and Wray S (1994). LHRH cells migrate on peripherin fibers in embryonic olfactory explant cultures: an in vitro model for neurophilic neuronal migration. *Dev. Biol.* 166: 331-348.

Gähwiler, B H (1981). Organotypic monolayer cultures of nervous tissue. *J. Neurosci. Methods* 4: 329-342.

Ganzler, S I, and Redies, C (1995). R-cadherin expression during nucleus formation in chicken forebrain. *J. Neurosci.* 15: 57-72.

Gomez, T M, and Spitzer, N C (1999). In vivo regulation of axon extension and pathfinding by growth-cone calcium transients. *Nature* 397: 350-355.

Gulyás, A I, Hájos, N, and Freund, TF (1996). Interneurons containing calretinin are specialized to control other neurons in the rat hippocampus. *J. Neurosci.* 16: 3397-3411.

Guth, S, Tange, TO, Kellenberger, E, Valcarcel, J. (2001). Dual function for U2AF35 in AG-dependent pre-mRNA splicing. *Mol Cell Biol* 21: 7673-7681.

Hatten, M E, and Heintz, N (1999). Neurogenesis and migration—In Fundamental Neuroscience, (R: Zigmond, ed.), pp 451-479, Academic Press, San Diego.

Hermann, D M, Mies, G, Hata, R, and Hossmann, K A (2000). Microglial and astrocytic reactions prior to onset of thalamic cell death after traumatic lesion of the rat sensorimotor cortex. *Acta Neuropathol (Berl)* 99: 147-153.

Hughes, P E, Alexi, T, Williams, C E, Clark, R G, and Gluckman, P D (1999). Administration of recombinant human Activin-A has powerful neurotrophic effects on select striatal phenotypes in the quinolinic acid lesion model of Huntington's disease. *Neuroscience* 92: 197-209.

Hwang et al., (1980). Hepatic Uptake and degredation of unilamellar sphingomyelin/cholesterol liposomes: a kinetic study. *Proc. of the Natl. Acad. Of Sciences USA* 77: 4030-4034.

Ishii, N, Wadsworth, W G, Stem, B D, Culotti, J G, and Hedgecock, E M (1992). UNC-6, a laminin-related protein, guides cell and pioneer axon migrations in C. elegans. *Neuron* 9: 873-881.

Langer et al., (1981) Biocompatibility of polymeric delivery systems for macromolecules. *J. Biomed. Mater. Res.* 15: 27-277.

Liang, S, and Crutcher, K A (1992). Neuronal migration in vitro. *Dev. Brain Res.* 66: 127-132.

Lu, Q., Sun, E., Klein, R. S. and Flanagan I. G.(2001). Ephrin-β reverse signalling is mediated by a novel PDZ-RGS protein and selectively inhibits G-protein coupled in chemoattraction. *Cell* 105: 69-79.

Nakao, N, and Itakura, T (2000). Fetal tissue transplants in animal models of Huntington's disease: the effects on damaged neuronal circuitry and behavioural deficits. *Prog. Neurobiol.* 61: 313-338.

Obst, K, and Wahle, P (1995). Areal differences of NPY mRNA expressing neurons are established in the late postnatal rat visual cortex in vivo, but not in organotypic cultures. *Eur. J. Neurosci.* 7: 2139-2158.

Pasterkamp, R J, Giger, R J, Baker, R E, Hermens, W T, and Verhaagen J. (2000). Ectopic adenoviral vector-directed expression of Sema3A in organotypic spinal cord explants inhibits growth of primary sensory afferents. *Dev. Biol.* 220: 129-141.

Paxinos, G, Toerk, I, Tecott, L H, and Valentino, K L (1991). *Atlas of the Developing* Brain. Academic Press: San Diego.

Polleux, F, Morrow, T, and Ghosh, A (2000). Semaphorin3A is a chemoattractant for cortical dendrites. *Nature* 404: 567-573.

Rozas, G, Liste, I, Lopez-Martin, E, Guerra, M j, Kokaia, M, and Labandeira-Garcia, J L (1996). Intrathalamic implants of GABA-releasing polymer matrices reduce motor impairments in rats with excitotoxically lesioned striata. *Exp. Neurol.* 142: 323-330.

Sieg, F, Obst, K, Gorba, T, Riederer, B. Pape, H-C, and Wahle, P (1998). Postnatal expression pattern of calcium-binding proteins in organotypic thalamic cultures and in the dorsal thalamus in vivo. *Dev. Brain Res.* 110: 83-95.

Stoppini, L, Buchs, P-A, and Muller, D (1991). A simple method for organotypic cultures of nervous tissue. *J. Neurosci. Methods* 37: 173-182.

Van der Flier, A, Kuikman, I, Kramer, D, Geerts, D, Kreft, M, Takafuta, T, Shapiro, S S and Sonnenberg, A (2002). Different splice variants of filamin-β affect myogenesis, subcellular distribution, and determine binding to integrin β subunits. *J. Cell Biol* 156: 361-376.

Wagener, R, Kobbe, B, Aszodi, A, Aeschlimann, D, and Paulsson M (2001). Characterization of the mouse matrilin-4 gene: A 5' antiparallel overlap with the gene encoding the transcription factor RBP-L. *Genomics* 76: 89-98.

Wagner et al., (1990) Transferrin-polycation conjugates as carriers for DNA uptake into cells. *Proc. Natl. Acad. Sci. USA.* 87: 3410-3414.

Wu et al., (1987) Receptor-mediated in vitro gene transformation by a soluble DNA carrier system. *J. Biol. Chem.* 262: 4429-4432.

Yamamoto M, Hassinger, L, and Crandall, J E (1990). Ultrastructural localization of stage-specific neurite-associated proteins in the developing rat cerebral and cerebellar cortices. *J. Neurocytol.* 19: 619-627.

Zhu, Y, Yu, T, Zhang, X-C, Nagasawa, T, Wu, J Y, Rao, Y (2002). Role of the chemokine SDF-1 as the meningeal attractant for embryonic cerebellar neurons. *Nature Neurosci.* 5: 719-720.

---

We claim:

1. An isolated peptide consisting of a sequence selected from the group consisting of SEQ ID NO:29, SEQ ID NO:30, SEQ ID NO:33, SEQ ID NO:34, SEQ ID NO:43, SEQ ID NO:44, SEQ ID NO:45, and SEQ ID NO:46.

2. The isolated peptide of claim 1, consisting of the sequence of SEQ ID NO:29.

3. The isolated peptide of claim 1, consisting of the sequence of SEQ ID NO:30.

4. The isolated peptide of claim 1, consisting of the sequence of SEQ ID NO:33.

5. The isolated peptide of claim 1, consisting of the sequence of SEQ ID NO:34.

6. The isolated peptide of claim 1, consisting of the sequence of SEQ ID NO:43.

7. The isolated peptide of claim 1, consisting of the sequence of SEQ ID NO:44.

8. The isolated peptide of claim 1, consisting of the sequence of SEQ ID NO:45.

9. The isolated peptide of claim 1, consisting of the sequence of SEQ ID NO:46.

10. A method for promoting neural cell proliferation in a mammal suffering from a neurodegenerative disorder due to hypoxia/ischemia, comprising administering to said mammal a pharmaceutically effective amount of a peptide having the sequence of SEQ ID NO:34.

11. The method of claim 10 where the neural cell is a neuron.

12. The method of claim 10, wherein said hypoxia/ischemia is due to one or more conditions selected from the group consisting of stroke, decreased perfusion caused by cardiac insufficiency/coronary bypass surgery, atherosclerotic thrombosis, embolism, hypertensive haemorrhage, ruptured aneurysm, vascular malformation, transient ischemic attack, intracranial haemorrhage, spontaneous subarachnoid haemorrhage, traumatic brain injury, traumatic intracerebral haemorrhage, cerebral contusion, basal skull fracture and hypertensive encephalopathy.

13. The method of claim 10, wherein said peptide is administered via a route selected from the group consisting of intravenous, intracerebral, lateral cerebroventricular, subcutaneous, intracisternal and parenteral.

14. A method for promoting neural cell migration in a mammal suffering from a neurodegenerative disorder due to hypoxia/ischemia, comprising administering to said mammal a pharmaceutically effective amount of a peptide having a sequence selected from the group consisting of SEQ ID NO:29, SEQ ID NO:30 and SEQ ID NO:34.

15. The method of claim 14 where the neural cell is a neuron.

16. The method of claim 14, wherein said hypoxia/ischemia is due to one or more conditions selected from the group consisting of stroke, decreased perfusion caused by cardiac insufficiency/coronary bypass surgery, atherosclerotic thrombosis, embolism, hypertensive haemorrhage, ruptured aneurysm, vascular malformation, transient ischemic attack, intracranial haemorrhage, spontaneous subarachnoid haemorrhage, traumatic brain injury, traumatic intracerebral haemorrhage, cerebral contusion, basal skull fracture and hypertensive encephalopathy.

17. The method of claim 14, wherein said peptide is administered via a route selected from the group consisting of intravenous, intracerebral, lateral cerebroventricular, subcutaneous, intracisternal and parenteral.

18. A method for promoting neural cell survival in a mammal suffering from a neurodegenerative disorder due to hypoxia/ischemia, comprising administering to said mammal a pharmaceutically effective amount of a peptide having a sequence selected from the group consisting of SEQ ID NO:30, SEQ ID NO:34 and SEQ ID NO:43.

19. The method of claim 18 where the neural cell is a neuron.

20. The method of claim 18, wherein said hypoxia/ischemia is due to one or more conditions selected from the group consisting of stroke, decreased perfusion caused by cardiac insufficiency/coronary bypass surgery, atherosclerotic thrombosis, embolism, hypertensive haemorrhage, ruptured aneurysm, vascular malformation, transient ischemic attack, intracranial haemorrhage, spontaneous subarachnoid haemorrhage, traumatic brain injury, traumatic intracerebral haemorrhage, cerebral contusion, basal skull fracture and hypertensive encephalopathy.

21. The method of claim 18, wherein said peptide is administered via a route selected from the group consisting of intravenous, intracerebral, lateral cerebroventricular, subcutaneous, intracisternal and parenteral.

22. A method for promoting neural cell differentiation in a mammal suffering from a neurodegenerative disorder due to hypoxia/ischemia, comprising administering to said mammal a pharmaceutically effective amount of a peptide having the sequence of SEQ ID NO:33.

23. The method of claim 22 where the neural cell is a neuron.

24. The method of claim 22, wherein said hypoxia/ischemia is due to one or more conditions selected from the group consisting of stroke, decreased perfusion caused by cardiac insufficiency/coronary bypass surgery, atherosclerotic thrombosis, embolism, hypertensive haemorrhage, ruptured aneurysm, vascular malformation, transient ischemic attack, intracranial haemorrhage, spontaneous subarachnoid haemorrhage, traumatic brain injury, traumatic intracerebral haemorrhage, cerebral contusion, basal skull fracture and hypertensive encephalopathy.

25. The method of claim 22, wherein said peptide is administered via a route selected from the group consisting of intravenous, intracerebral, lateral cerebroventricular, subcutaneous, intracisternal and parenteral.

26. A method for promoting neurite growth in a mammal suffering from a neurodegenerative disorder due to hypoxia/ischemia, comprising administering to said mammal a pharmaceutically effective amount of a peptide having a sequence selected from the group consisting of SEQ ID NO:30, SEQ ID NO:34, SEQ ID NO:44, SEQ ID NO: 45 and SEQ ID NO:46.

27. The method of claim 26, wherein said hypoxia/ischemia is due to one or more conditions selected from the group consisting of stroke, decreased perfusion caused by cardiac insufficiency/coronary bypass surgery, atherosclerotic thrombosis, embolism, hypertensive haemorrhage, ruptured aneurysm, vascular malformation, transient ischemic attack, intracranial haemorrhage, spontaneous subarachnoid haemorrhage, traumatic brain injury, traumatic intracerebral haemorrhage, cerebral contusion, basal skull fracture and hypertensive encephalopathy.

28. The method of claim 26, wherein said peptide is administered via a route selected from the group consisting of intravenous, intracerebral, lateral cerebroventricular, subcutaneous, intracisternal and parenteral.

* * * * *